US00RE49311E

(19) United States
(12) Reissued Patent
Van Der Lelie et al.

(10) Patent Number: US RE49,311 E
(45) Date of Reissued Patent: Nov. 29, 2022

(54) ***BACILLUS THURINGIENSIS* RTI545 COMPOSITIONS AND METHODS OF USE FOR BENEFITING PLANT GROWTH AND CONTROLLING PLANT PESTS**

(71) Applicant: FMC Corporation, Philadelphia, PA (US)

(72) Inventors: Daniel Van Der Lelie, Chapel Hill, NC (US); Safiyh Taghavi, Chapel Hill, NC (US); Vincent J. Spadafora, Yardley, PA (US); Nathan Caldwell, Morrisville, PA (US); Anders Obel, Kokkedal (DK); Robert B. Albright, Landsdale, PA (US); Guozhi Wang, New York, NY (US); Jaeheon Lee, Hellerup (DK); Roderick G. McLeod, Lethbridge (CA); Kevin Brost, Calgary (CA); John E. Kibbee, Guelph (CA)

(73) Assignee: FMC Corporation, Philadelphia, PA (US)

(21) Appl. No.: 16/749,275

(22) Filed: Jan. 22, 2020

Related U.S. Patent Documents

Reissue of:
(64) Patent No.: 10,390,535
Issued: Aug. 27, 2019
Appl. No.: 15/726,053
Filed: Oct. 5, 2017

U.S. Applications:
(60) Provisional application No. 62/404,275, filed on Oct. 5, 2016.

(51) Int. Cl.

| | |
|---|---|
| ***A01N 25/00*** | (2006.01) |
| ***A01N 43/56*** | (2006.01) |
| ***A01N 51/00*** | (2006.01) |
| ***A01N 53/00*** | (2006.01) |
| ***A01N 63/00*** | (2020.01) |
| ***A01N 63/23*** | (2020.01) |
| ***C12N 1/20*** | (2006.01) |
| *C12R 1/07* | (2006.01) |

(52) U.S. Cl.
CPC ..... *A01N 63/23* (2020.01); *A01N 53/00* (2013.01); *C12N 1/205* (2021.05); *C12R 2001/075* (2021.05)

(58) Field of Classification Search
None
See application file for complete search history.

(56) References Cited

U.S. PATENT DOCUMENTS

| | | | |
|---|---|---|---|
| 6,210,953 | B1 | 4/2001 | Osman et al. |
| 10,390,535 | B2 | 8/2019 | Van Der Lelie et al. |

FOREIGN PATENT DOCUMENTS

| | | | |
|---|---|---|---|
| CN | 104286041 | | 1/2015 |
| CN | 105838634 | | 5/2019 |
| JP | 2015-523971 | | 4/2017 |
| JP | 2015-518020 | | 2/2018 |
| WO | 2009/126473 | A1 | 10/2009 |
| WO | 2013/178648 | A1 | 12/2013 |
| WO | 2013/178649 | A1 | 12/2013 |
| WO | 2013/178664 | A1 | 12/2013 |
| WO | 2016/108972 | A1 | 7/2016 |
| WO | 2016/115476 | A1 | 7/2016 |

OTHER PUBLICATIONS

Tokio Ichimatsu and five others, "Development of the Biological Control Agent Using Multiple *Bacillus thuringiensis* Strains", Fukuoka Industrial Technology Center Research Report, 2005, No. 15, pp. 35-38, http://www.fitc.pref.fukuoka.jp/kenkyu/report/h15/h15-09.pdf.

Tokio Ichimatsu and five others, "Development of the antibacterial soil improvementmaterial utilized *Bacillus thuringiensis* strains", Fukuoka Industrial Technology Center Research Report, 2005, No. 15, pp. 47-49.

Shinichi Goto and three others, "Control of Bacterial Wilt of Tomato by *Bacillus thuringiensis* and Several Biopesticide", Japanese Journal of General Plant Pathology, 2014, vol. 80, No. 1, p. 67.

Richter M, and Rossell6-M6ra R (2009) Shifting the genomic gold standard for the prokaryotic species definition. Proc Natl Acad Sci USA 106(45):19126-31.

Shanma et al., "Isolation of Phosphate Solubilizing Microorganism {PSMs) From Soil", 2011, Journal of Microbiology and Biotechnology Research 1: 90-95.

Joseph W. Kloepper, et al. "Induced Systemic Resistance and Promotion of Plant Growth by *Bacillus* spp.", 2004, Phytopathology vol. 94, No. 11, 1259-1266.

Richter M, and Rosselló-Móra R (2009) Shifting the genomic gold standard for the prokaryotic species definition. Proc Natl Acad Sci USA 106(45):19126-31.

Mesuere, B., Debyser, G., Aerts, M., Devreese, B., Vandamme, P. and Dawyndt, P. (2015), The Unipept metaproteomics analysis pipeline. Proteomics, 15: 1437-1442. doi:10.1002/pmic.201400361.

Sokol et al., "A More Sensitive Plate Assay for Detection of Protease Production by Pseudomonas aeruginosa", 1979, Journal of Clinical Microbiology. 9: 538-540.

Taghavi, et al., "Genome Survey and Characterization of Endophytic Bacteria Exhibiting a Beneficial Effect on Growth and Development of Poplar Trees", 2009, Applied and Environmental Microbiology 75: 748-757.

Sharma et al., "Isolation of Phosphate Solubilizing Microorganism (PSMs) From Soil", 2011, Journal of Microbiology and Biotechnology Research 1: 90-95.

*Primary Examiner* — Bruce R Campell
(74) *Attorney, Agent, or Firm* — Armstrong Teasdale LLP

(57) ABSTRACT

Compositions are provided that include a new Bacillus thuringiensis strain designated RTI545 for use in benefiting plant growth and controlling plant pests. In particular, the RTI545 strain is useful for controlling plant nematode, insect and fungal pests. The compositions include plant seeds coated with the RTI545 strain. The compositions can be applied alone or in combination with other microbial, biological, or chemical insecticides, fungicides, nematicides, bacteriocides, herbicides, plant extracts, plant growth regulators, or fertilizers. In one example, enhanced growth and insect control are provided by delivering at the time of planting a combination of a chemical insecticide such as bifenthrin and a liquid fertilizer to plants or seeds treated with RTI545.

26 Claims, 6 Drawing Sheets

Specification includes a Sequence Listing.

*BACILLUS THURINGIENSIS* RTI545 COMPOSITIONS AND METHODS OF USE FOR BENEFITING PLANT GROWTH AND CONTROLLING PLANT PESTS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATION

This application claims the benefit of U.S. provisional application No. 62/404,275, filed Oct. 5, 2016, the disclosure of which is hereby incorporated herein by reference in its entirety.

TECHNICAL FIELD

The presently disclosed subject matter relates to compositions comprising an isolated Bacillus thuringiensis bacterial strain for application to plant seeds and roots, and the soil surrounding plants to benefit plant growth and to control plant pests.

BACKGROUND

A number of microorganisms having beneficial effects on plant growth and health are known to be present in the soil, to live in association with plants specifically in the root zone (rhizosphere-associated bacteria), or to reside as endophytes within the plant. Their beneficial plant growth promoting properties include nitrogen fixation, iron chelation, phosphate solubilization, inhibition of non-beneficial microorganisms, resistance to, or exclusion of pests, Induced Systemic Resistance (ISR), Systemic Acquired Resistance (SAR), decomposition of plant material in soil to increase useful soil organic matter, and synthesis of phytohormones such as indole-acetic acid (IAA), acetoin and 2,3-butanediol that stimulate plant growth, development and responses to environmental stresses such as drought. In addition, these microorganisms can interfere with a plant's ethylene stress response by breaking down the precursor molecule, 1-aminocyclopropane-1-carboxylate (ACC), thereby stimulating plant growth and slowing fruit ripening. These beneficial microorganisms can improve soil quality, plant growth, yield, and quality of crops. Various microorganisms exhibit biological activity such as to be useful to control plant diseases. Such biopesticides (living organisms and the compounds naturally produced by these organisms) are generally considered safer and more biodegradable than synthetic fertilizers and pesticides.

For example, beneficial plant associated bacteria, both rhizospheric and endophytic, are known to provide a multitude of benefits to host plants that ranges from resistance to diseases and insects pests and tolerance to environmental stresses including cold, salinity and drought stress. As the plants with inoculated plant growth promoting bacteria acquire more water and nutrients from soils, e.g. due to a better developed root system, the plants grow healthier and are less susceptible to biotic and abiotic stresses. As such the microbial compositions of the present invention can be applied alone or in combination with current crop management inputs such as chemical fertilizers, herbicides, and pesticides to maximize crop productivity. Plant growth promoting effects translate into faster growing plants and increase above ground biomass, a property that can be applied to improve early vigor. One benefit of improved early vigor is that plants are more competitive and outcompete weeds, which directly reduces the cost for weed management by minimizing labor and herbicide application. Plant growth promoting effects also translate into improved root development, including deeper and wider roots with more fine roots that are involved in the uptake of water and nutrients. This property allows for better use of agricultural resources, and a reduction in water used in irrigation needs and/or fertilizer application. Changes in root development and root architecture affect the interactions of the plant with other soil-borne microorganisms, including beneficial fungi and bacteria that help the plant with nutrient uptake including nitrogen fixation and phosphate solubilization. These beneficial microbes also compete against plant pathogens to increase overall plant health and decrease the need for chemical fungicides and pesticides. A more developed root system also allows for improved yields when pests are present.

Fungal phytopathogens, including but not limited to Botrytis spp. (e.g. Botrytis cinerea), Fusarium spp. (e.g. F. oxysporum and F. graminearum), Rhizoctonia spp. (e.g. R. solani), Magnaporthe spp., Mycosphaerella spp., Puccinia spp. (e.g. P. recondita), Phytopthora spp. and Phakopsora spp. (e.g. P. pachyrhizi), are one type of plant pest that can cause severe economic losses in the agricultural and horticultural industries. Chemical agents can be used to control fungal phytopathogens, but the use of chemical agents suffers from disadvantages including high cost, emergence of resistant strains of pests, and potentially undesirable environmental impacts. In addition, such chemical treatments may adversely affect beneficial bacteria, fungi, and arthropods in addition to the plant pest at which the treatments are targeted. A second type of plant pest are bacterial pathogens, including but not limited to Erwinia spp. (such as Erwinia chrysanthemi), Pantoea spp. (such as P. citrea), Xanthomonas (e.g. Xanthomonas campestris), Pseudomonas spp. (such as P. syringae) and Ralstonia spp. (such as R. soleacearum) that cause severe economic losses in the agricultural and horticultural industries. Similar to pathogenic fungi, the use of chemical agents to treat these bacterial pathogens suffers from disadvantages. Viruses and virus-like organisms comprise a third type of plant disease-causing agent that is hard to control, but to which bacterial microorganisms can provide resistance in plants via induced systemic resistance (ISR). Thus, microorganisms that can be applied as biofertilizer and/or biopesticide to control pathogenic fungi, viruses, and bacteria are desirable and in high demand to improve agricultural sustainability. A final type of plant pathogen includes plant pathogenic nematodes and insects, which can cause severe damage and loss of plants and reductions in yield.

Some members of the species Bacillus have been reported as biocontrol strains, and some have been applied in commercial products (Joseph W. Kloepper, et al. 2004, Phytopathology Vol. 94, No. 11, 1259-1266). For example, strains currently being used in commercial biocontrol products include: Bacillus pumilus strain QST2808, used as active ingredient in SONATA and BALLAD-PLUS, produced by BAYER CROP SCIENCE; Bacillus pumilus strain GB34, used as active ingredient in YIELDSHIELD, produced by BAYER CROP SCIENCE; Bacillus subtilis strain QST713, used as the active ingredient of SERENADE, produced by BAYER CROP SCIENCE; Bacillus subtilis strain GBO3, used as the active ingredient in KODIAK and SYSTEM3, produced by HELENA CHEMICAL COMPANY. Various strains of Bacillus thuringiensis and Bacillus firmus have been applied as biocontrol agents against nematodes and insects and these strains serve as the basis of numerous commercially available biocontrol products, including DIPEL comprising a Bacillus thuringiensis subsp. kurstaki strain, produced by VALENT BIOSCIENCES CORPORATION, and NORTICA and PONCHO-VOTIVO comprising a B. firmus strain, produced by BAYER CROP SCIENCE. In addition, Bacillus strains currently being used in commercial biostimulant products include: Bacillus subtilis var. amyloliquefaciens strain FZB42 used as the active ingredient in RHIZOVITAL 42, produced by ABiTEP GmbH, as well as various other Bacillus subtilis species that are included as whole cells including their fermentation extract in biostimulant products, such as FULZYME produced by JHBiotech Inc.

However, it is desirable to develop new compositions and methods for benefiting plant growth and controlling plant pests.

SUMMARY

The presently disclosed subject matter provides microbial compositions and methods for their use in benefiting plant growth and controlling plant pests.

In one embodiment, a composition is provided comprising a biologically pure culture of Bacillus thuringiensis RTI545 deposited as ATCC No. PTA-122161, or a mutant thereof having all the identifying characteristics thereof, for application to a plant for one or both of benefiting plant growth or conferring protection against a plant pest in a susceptible plant.

In one embodiment, a method is provided for one or both of benefiting growth of a plant or conferring protection against a plant pest in a susceptible plant, the method comprising delivering a composition comprising a biologically pure culture of Bacillus thuringiensis RTI545 deposited as ATCC No. PTA-122161, or a mutant thereof having all the identifying characteristics thereof to a plant, plant part, seed of the plant, roots of the plant, soil or growth medium surrounding the plant or the seed of the plant, or soil or growth medium before planting the plant or sowing seed of the plant, in an amount suitable to benefit the plant growth and/or to confer protection against the plant pest in the susceptible plant.

In one embodiment, a method is provided for one or both of benefiting growth of a plant or conferring protection against a plant pest in a susceptible plant, the method comprising: delivering to the plant, plant part, seed of the plant, roots of the plant, soil or growth medium surrounding the plant or the seed of the plant, or soil or growth medium before planting the plant or sowing seed of the plant, a combination of: a composition comprising a biologically pure culture of Bacillus thuringiensis RTI545 deposited as ATCC No. PTA-122161, or a mutant thereof having all the identifying characteristics thereof in an amount suitable to benefit the plant growth and/or to confer protection against the plant pest in the susceptible plant; and one or a combination of an insecticide, a fungicide, nematicide, bacteriocide, biostimulant, herbicide, plant extract, microbial extract, plant growth regulator, or fertilizer, in an amount suitable to benefit the plant growth and/or to confer protection against the plant pest in the susceptible plant. Each of these additional agents can be either a biological agent or a chemical agent.

In one embodiment, a plant seed is provided coated with a composition comprising spores of a biologically pure culture of Bacillus thuringiensis RTI545 deposited as ATCC No. PTA-122161, or a mutant thereof having all the identifying characteristics thereof, present in an amount suitable to benefit plant growth and/or to confer protection against a plant pest in a susceptible plant.

In one embodiment, a method is provided for one or both of benefiting growth of a plant or conferring protection against a plant pest in a susceptible plant, the method comprising planting a seed of the plant, wherein the seed has been coated with a composition comprising a biologically pure culture of Bacillus thuringiensis RTI545 deposited as ATCC PTA-122161, or a mutant thereof having all the identifying characteristics thereof, wherein growth of the plant from the seed is benefited and/or protection against the plant pest is conferred.

In one embodiment, a composition is provided for benefiting plant growth, the composition comprising: a biologically pure culture of Bacillus thuringiensis s RTI545 deposited as ATCC No. PTA-122161, or a mutant thereof having all the identifying characteristics thereof; and a bifenthrin insecticide.

BRIEF DESCRIPTION OF THE FIGURES

Having thus described the presently disclosed subject matter in general terms, reference will now be made to the accompanying Figures described below.

FIG. 1A is a schematic diagram showing on the far left a plant seed (inner circle) coated with a chemical insecticide (dark band surrounding inner circle) with plant insect pests in the plant rhizosphere represented by horizontal marks. The middle portion of the diagram shows the sprouted plant seed with diffused insecticide protecting the roots of the plant seed from the insect pests (protection represented by the "X" marks). The far right of the diagram shows diminished protection of the roots of the plant seed from the insect pests as the roots grow beyond the diffusion zone of the chemical insecticide.

FIG. 1B shows the schematic diagram of FIG. 1A with the addition of Bacillus thuringiensis RTI545 to the coating on the plant seed or to the soil surrounding the plant seed according to one or more embodiments of the present disclosure. The far right of the diagram shows continued protection of the roots of the plant seed from the insect pests even as the roots grow beyond the diffusion zone of the chemical insecticide as a result of the establishment of Bacillus thuringiensis RTI545 in the plant rhizosphere.

Figure 2:
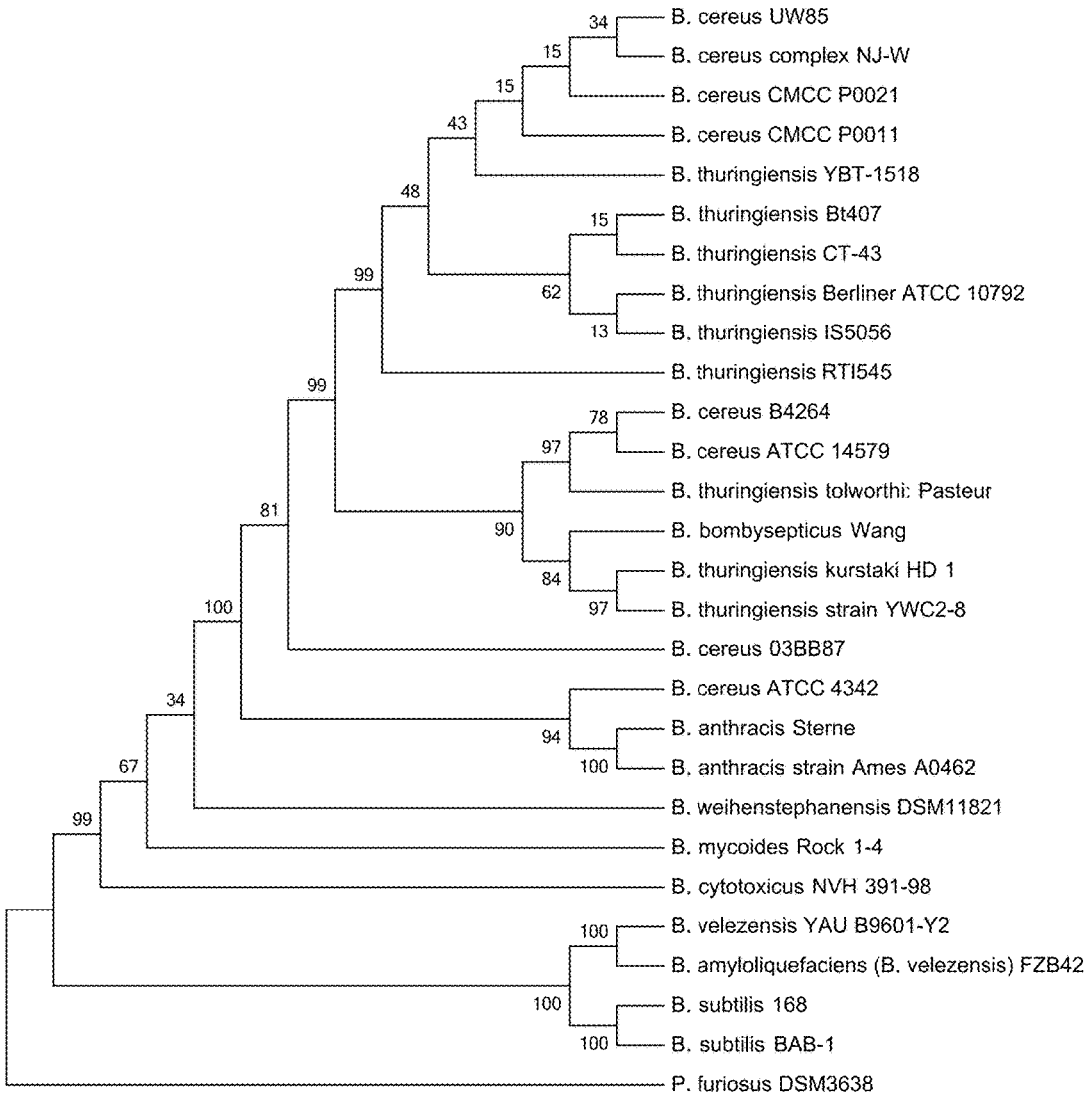

FIG. 2 is a schematic drawing showing the phylogeny of the RTI545 strain using the housekeeping gene rpoB according to one or more embodiments of the present disclosure.

Bootstrap values indicate replicates of 1000. Outgroup sequences are from the hypertheromiphilic archaea Pyrococcus furiosus DSM3638.

Figures 3A, 3B:
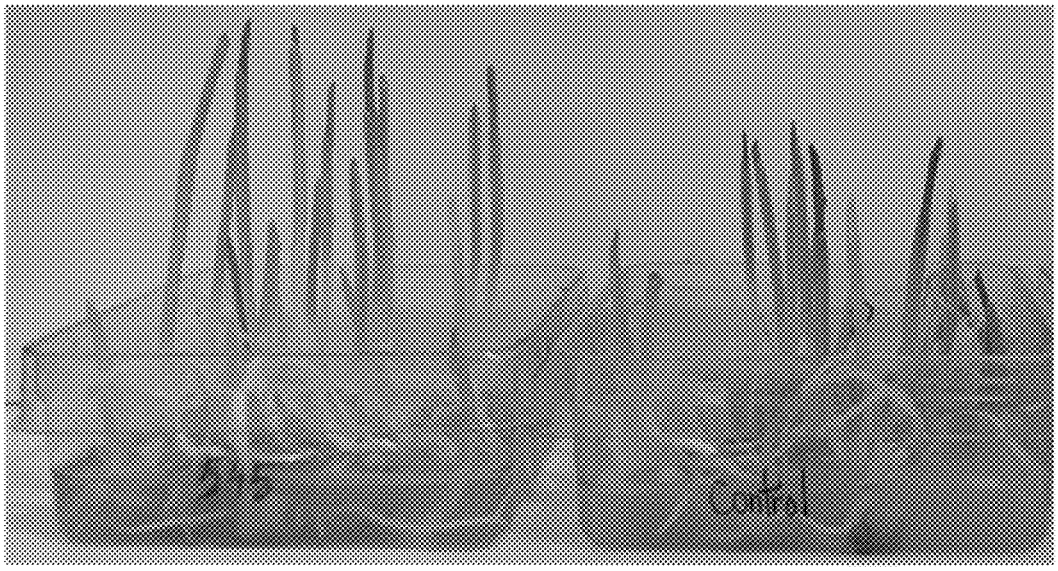

FIG. 3A is an image of corn seedlings taken 12 days from planting of seed treated with vegetative cells of Bacillus thuringiensis strain RTI545 at planting by drench irrigation according to one or more embodiments of the present disclosure.

FIG. 3B is an image of corn seedlings taken 12 days from planting of seed treated similarly to that in FIG. 3A but without the addition of the Bacillus thuringiensis RTI545 cells.

Figure 4:
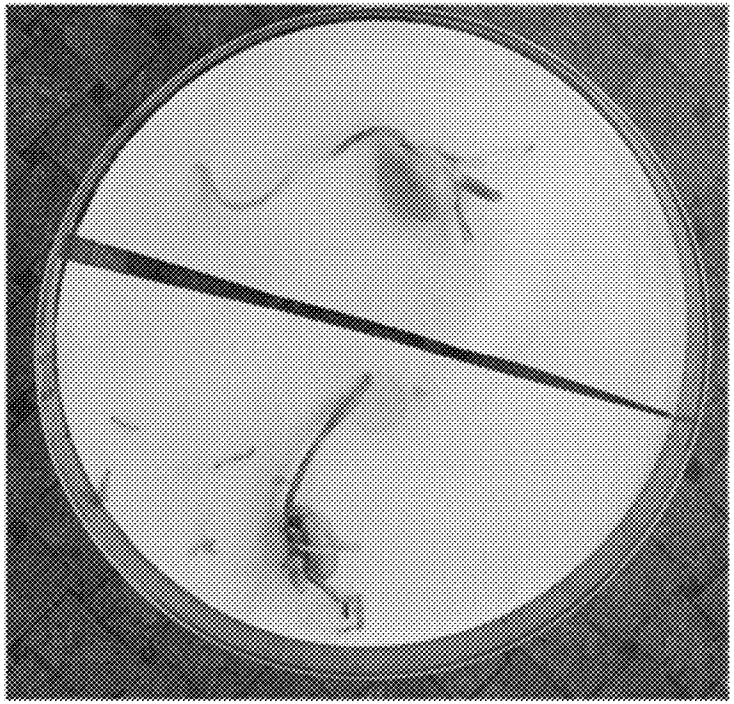

FIG. 4 is an image showing the ability of Bacillus thuringiensis RTI545 cells to repel Southern corn rootworm (SCRW) larvae in a choice feeding assay of corn seedlings according to one or more embodiments of the present disclosure. In the image, the filter paper on the left was treated with Bacillus thuringiensis strain RTI545 cells and the filter paper on the right was treated with water as a control.

Figure 5:
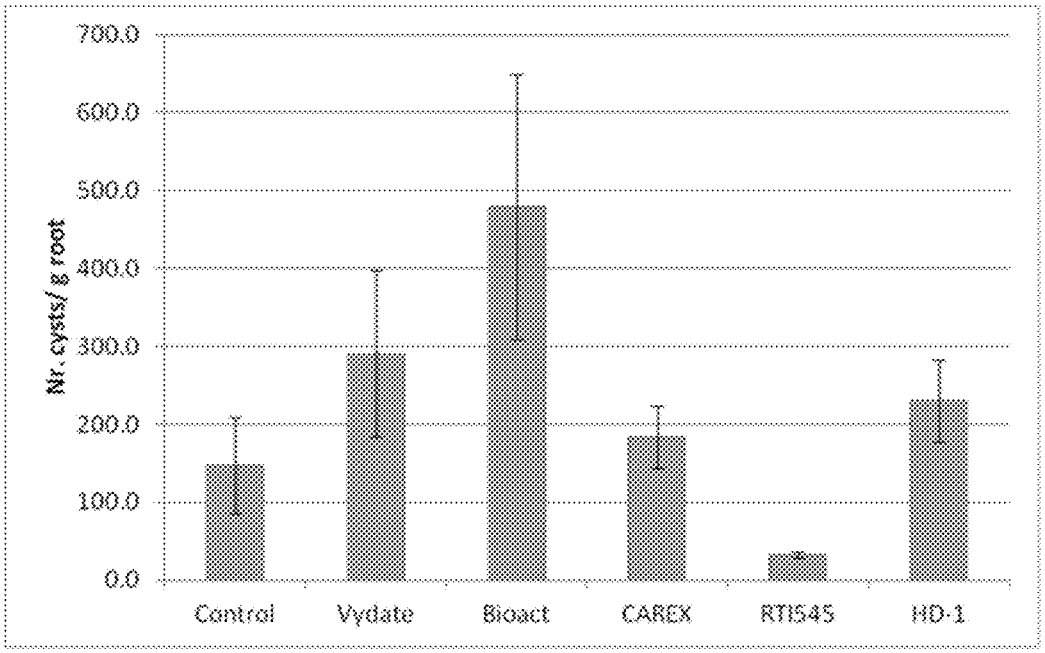

FIG. 5 is a graph showing the number of cysts per gram of root biomass of potato plants potted in soil naturally infected with Globodera sp. nematodes and enhanced with $10^9$ cfu spores per liter soil Bacillus thuringiensis RTI545 cells (RTI545) as compared to control and soil treatments: Vydate (DUPONT; A.I.=Oxamyl [Methoyl N'N'-dimethyl-N-[(methyl carbamoyl)oxyl)oxy]-1-thiooxamimidate), BIO-ACT (BAYER CROPSCIENCES LP; Paecilomyces lilacinus strain 251), CAREX (NUFARM, pyridaben), and HD-1 (Bacillus thuringiensis subsp. kurstaki HD-1) according to one or more embodiments of the present disclosure.

Figure 6A:
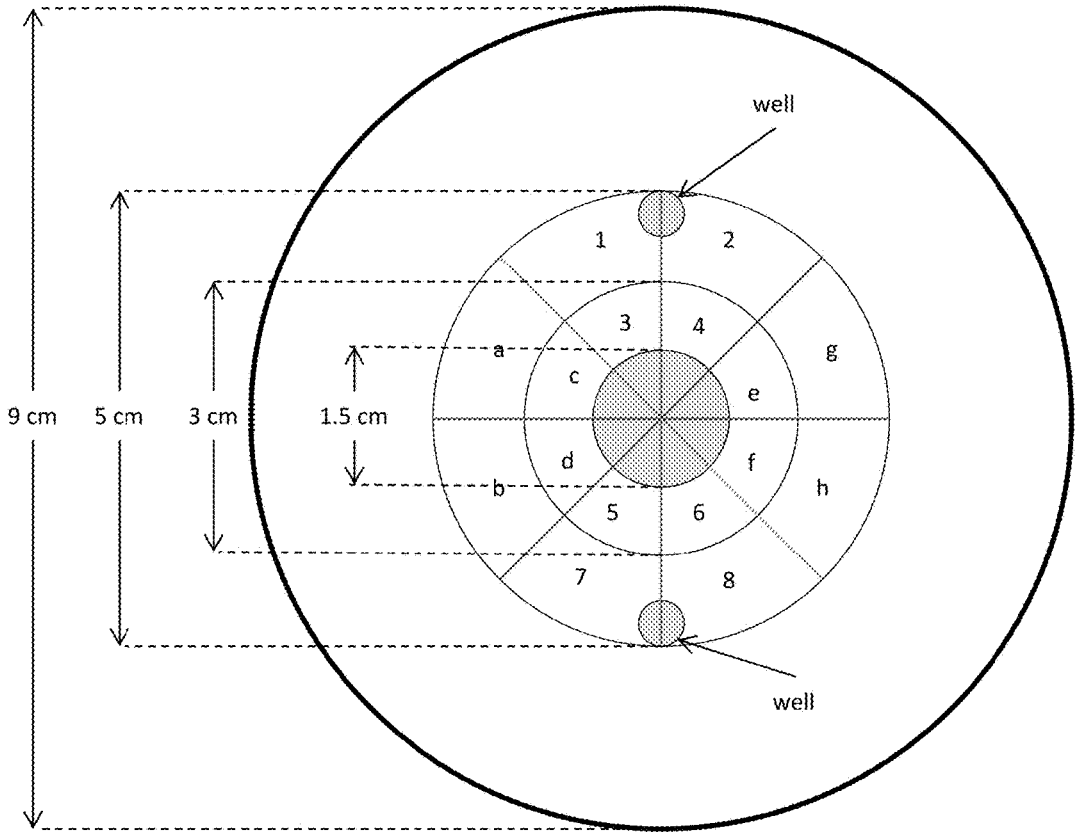
Figure 6B:
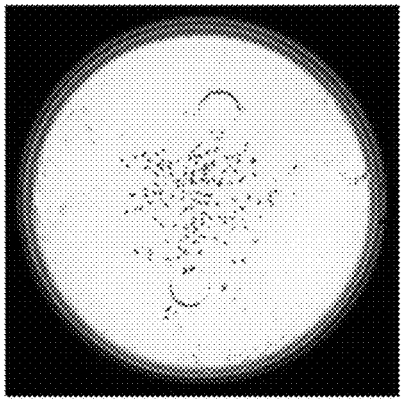
Figure 6C:
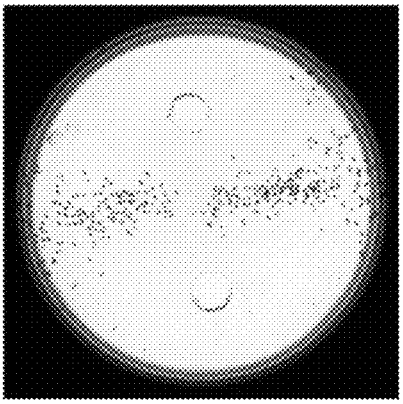

FIG. 6A shows a schematic plan drawing of a chemotaxis test arena for assaying attraction/repellency of test samples to nematodes. FIG. 6B is a photograph of an assay of kanosamine tested at 100 μg/ml, wherein dots representing nematode locations indicate neutral distribution. FIG. 6C is a photograph of an assay of RTI545 supernatent tested at 100% strength, wherein dots representing nematode locations indicate repellant distribution.

DETAILED DESCRIPTION

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range. When a range is recited as being from a list of lower limits to a list of upper limits, ranges are defined as being from any one of the recited lower limits to any one of the recited upper limits.

Tradenames are indicated herein in UPPERCASE.

As used herein for the purposes of this specification and claims, in one embodiment, the phrase "a biologically pure culture of Bacillus thuringiensis RTI545" refers to one or a combination of: spores of a biologically pure fermentation culture of the bacterial strain, vegetative cells of a biologically pure fermentation culture of the bacterial strain, one or more products of a biologically pure fermentation culture of the bacterial strain, a culture solid of a biologically pure fermentation culture of the bacterial strain, a culture supernatant of a biologically pure fermentation culture of the bacterial strain, and a cell-free extract of a biologically pure fermentation culture of the bacterial strain.

In another embodiment, the phrase "a biologically pure culture of Bacillus thuringiensis RTI545" refers to one or a combination of: spores of a biologically pure fermentation culture of the bacterial strain, vegetative cells of a biologically pure fermentation culture of the bacterial strain, one or more products of a biologically pure fermentation culture of the bacterial strain, and a culture solid of a biologically pure fermentation culture of the bacterial strain. In one variant of this embodiment, the phrase may refer to the spores of a biologically pure fermentation culture of the bacterial strain.

In still another embodiment, the phrase "a biologically pure culture of Bacillus thuringiensis RTI545" refers to one or a combination of: a culture supernatant of a biologically pure fermentation culture of the bacterial strain, and a cell-free extract of a biologically pure fermentation culture of the bacterial strain.

Notably, the "a biologically pure culture of Bacillus thuringiensis RTI545" may be in the form of spores, vegetative cells or cell-free extracts of the biologically pure culture.

As used herein for the purposes of this specification and claims, the phrase "a plant pest" refers to any pest that is harmful and/or pathogenic to a plant, including without limitation, a plant pest such as an insect, a parasite, a nematode, a fungus, a bacteria, or a virus.

A new plant-associated bacterium isolated from the soil of fescue grass is provided herein and referred to as "RTI545". The strain was identified as being a Bacillus thuringiensis strain based on sequence analysis, although the strain lacks the genes for crystal proteins often found in B. thuringiensis strains. Unexpectedly, the RTI545 strain demonstrates strong insect repelling activity, but fails to kill the insect larvae in direct contact and choice feeding assays. Compositions and methods are provided herein that include a biologically pure culture of the Bacillus thuringiensis RTI545 strain for delivery to a plant, plant part, plant seed, plant roots, or soil to benefit plant growth and confer protection against plant pests. The growth benefits and conferred protection include improved seedling vigor, improved root development, improved plant growth, improved plant health, increased yield, improved appearance, improved resistance to plant pests, reduced pathogenic infection, or a combination thereof.

Delivery of the composition to the plant or plant part includes delivery to any portion of the plant, including above-ground portions, such as foliar parts, and parts of plants for propagating the plant such as seedlings, transplants, cuttings (e.g. stems, roots, leaves, and the like), rhizomes, spores, setts (e.g. of sugarcane), bulbs, corms, tubers, or portions thereof, or other plant tissue from which a complete plant can be obtained. Delivery to the soil or growth medium surrounding the plant or the seed of the plant, or soil or growth medium before planting the plant or sowing seed of the plant includes in-furrow applications of the composition at the time of planting, includes incorporation or mixing of the composition with the soil or growth medium, application of the composition to the surface of the soil or growth medium such as by soil drench, and the like.

Figure 1:
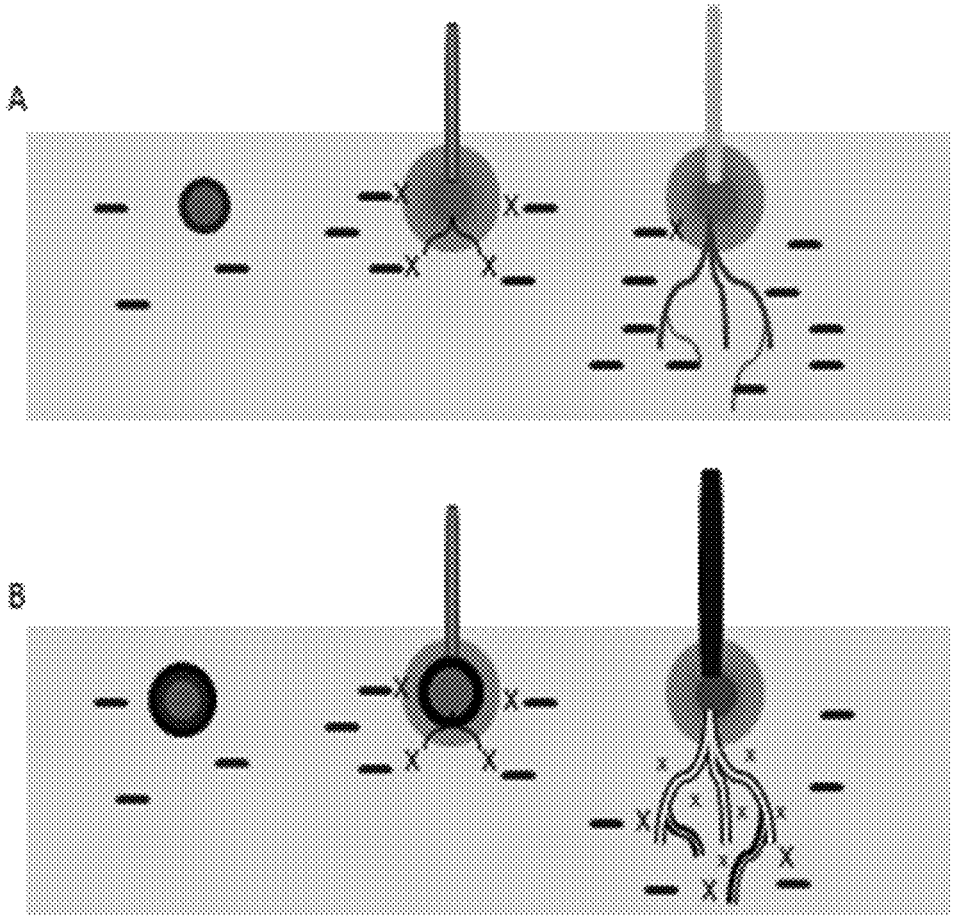

In one embodiment, the Bacillus thuringiensis RTI545 strain is delivered to a plant, plant part, plant seed, plant roots or soil in combination with a chemical insecticide to extend the control of the chemical insecticide through establishment of the RTI545 strain in the plant rhizosphere. A proposed mechanism of this insect control by the RTI545 strain is illustrated in FIG. 1. FIG. 1A shows insect control by coating a seed with a chemical insecticide alone (i.e., without RTI545). A plant seed (inner circle) coated with an insecticide (dark band surrounding inner circle) is shown on the far left of the FIG. 1A diagram, which is surrounded by plant insect pests in the plant rhizosphere represented by horizontal marks. The middle portion of the diagram shows the sprouted plant seed with diffused insecticide protecting the roots of the plant seed from the insect pests (protection represented by the "X" marks). The far right of the diagram shows diminished protection of the roots of the plant seed from the insect pests as the roots grow beyond the diffusion zone of the chemical insecticide. The diagram in FIG. 1B illustrates a proposed mechanism for how addition of Bacillus thuringiensis RTI545 spores to the coating on the plant seed or as an in-furrow application improves insect control over use of the insecticide coating alone. Specifically, the far right side of the FIG. 1B diagram shows continued protection of the roots of the plant seed from the insect pests even as the roots grow beyond the diffusion zone of the chemical insecticide as a result of the establishment of Bacillus thuringiensis RTI545 in the plant rhizosphere. In one example, seeds coated with RTI545 cells or otherwise treated with RTI545 are planted in combination with the chemical insecticide, bifenthrin, and application of a liquid fertilizer to benefit plant growth and control insect pests.

The isolation and characterization of the RTI545 strain is described more specifically in the EXAMPLEs provided herein. EXAMPLE 1 describes comparison of the sequences of the 16S rDNA (SEQ ID NO.: 1) and rpoB (SEQ ID NO.: 2) genes of the RTI545 strain to those of other known bacterial strains in the NCBI and RDP databases using BLAST. This analysis placed strain RTI545 within the Bacillus cereus/thuringiensis/anthracis clade. Further phylogenetic analysis of the RTI545 strain and relevant Bacillus species was performed using Bootstrap consensus trees (1000 replicates) on the rpoB gene. The consensus tree for the rpoB gene is shown in FIG. 2. As can be seen in FIG. 2, the RTI545 strain forms a separate branch in the Bacillus cereus/thuringiensis/anthracis clade indicating that RTI545 is a new strain falling within the Bacillus cereus/thuringiensis/anthracis clade. Additional sequence analysis revealed that the RTI545 strain lacks the genes for crystal proteins often found in B. thuringiensis strains.

In addition, whole genome sequence analysis was performed to compare the RTI545 strain with closely related strains of the Bacillus species using both MUMmer- and BLASTn-based Average Nucleotide Identity (ANI) and UNIPEPT analysis to confirm its phylogenetic classification. The results of the MUMmer and BLASTn based ANI calculations are shown in Table I below. Both the ANI and UNIPEPT (data not shown) analyses revealed a significant degree of sequence similarity between RTI545 and published sequences of strains indicated as both B. cereus and B. thuringiensis. The highest sequence similarity to a recognized type strain is to the recognized type strain B. thuringiensis Berliner ATCC10792. Again the differences in whole genome sequence from those previously published indicate that RTI545 is a new Bacillus thuringiensis strain falling within the Bacillus cereus/thuringiensis/anthracis clade.

Based on the foregoing sequence analyses, the RTI545 strain was identified as a new strain, and is herein referred to as a Bacillus thuringiensis strain.

The strain of RTI545 was deposited on May 12, 2015 under the terms of the Budapest Treaty on the International Recognition of the Deposit of Microorganisms for the Purposes of Patent Procedure at the American Type Culture Collection (ATCC) in Manassas, Va., USA and bears the Patent Accession No. PTA-122161. All restrictions upon availability to the public will be irrevocably removed upon granting of the patent.

Experimental results demonstrating the growth promoting, antimicrobial, and insect and nematode and fungal control activities of the Bacillus thuringiensis RTI545 strain in various plants and under varying conditions including in vitro, greenhouse and field trial studies are provided in FIGS. 3-5 and in EXAMPLES 2-17 herein. Specifically, the Bacillus thuringiensis RTI545 strain is shown to benefit plant growth and confer control against plant pests including rootworms such as Southern corn rootworm (SCRW), wireworms such as wheat wireworms and corn wireworms, white grub complex pests, soil-dwelling maggots such as seed corn maggots and seed maggots, plant bugs such as Western plant bug (WPB), nematodes and fungal pathogens such as Rhizoctonia spp. In some cases, seed treatment with the Bacillus thuringiensis RTI545 strain provided equivalent or superior results as compared to commercially available products based on a combination of biological and chemical active agents or chemical active agents alone.

The antagonistic properties of the Bacillus thuringiensis RTI545 against several major plant pathogens in plate assays are described in EXAMPLE 2 and phenotypic traits such as phytohormone production, acetoin and indole acetic acid (IAA), and nutrient cycling of the strain are described in EXAMPLE 3.

EXAMPLE 4 describes the positive effects of incubation of corn seed with RTI545 cells on seed germination, root development, and early growth. The results are shown in FIG. 3A and FIG. 3B, which are images of the corn seedlings after 12 days grown in the presence (FIG. 3A) and absence (FIG. 3B) of the RTI545 strain. As can be seen in the figures, the presence of the RTI545 strain resulted in a significant growth advantage.

EXAMPLE 5 describes the positive effects of inoculation of corn seed with RTI545 cells on early plant growth and vigor. Surface sterilized germinated corn seeds were inoculated for 2 days in a suspension of $10^8$ CFU/ml of RTI545 at room temperature and, subsequently, the inoculated seeds were planted in pots and incubated in a greenhouse. The wet and dry weight of the corn shoot biomass was measured after 42 days growth. Wet weight and dry weight of the corn shoot biomass increased for the plants inoculated with the Bacillus thuringiensis RTI545 strain compared to the non-inoculated control. As can be discerned from the significant increase in both wet and dry biomass, the presence of the RTI545 strain resulted in a significant growth advantage.

EXAMPLE 6 describes the unexpected insect repelling activity of the RTI545 strain. For antagonism against Western plant bug (WPB), Bacillus thuringiensis RTI545 was evaluated in direct spray, choice feeding, and no-choice feeding assays along with controls including a media blank, chemical active agent (O,S-Dimethyl acetylphosphoramidothioate), and Bacillus thuringiensis subsp. kurstaki HD-1 (HD-1). As expected, no significant mortality (direct spray and no-choice feeding assays) or repellency (choice feeding assay) was observed for the medium blank or HD-1 treatments, while the chemical control killed (direct spray and no-choice feeding assays) and repelled (choice feeding assay) the WPB. Bacillus thuringiensis RTI545 provided no significant mortality to WPB when applied in both direct spray and in no-choice feeding assays; however, unexpectedly, RTI545 displayed a repellent behavior at 124 hours after WPB were placed into choice assay arenas. Specifically, when the WPB were placed into a container containing a treated and a non-treated food source, WPB were observed to be feeding only on the non-treated food source (data not shown).

For antagonism against Southern corn rootworm (SCRW) larvae, Bacillus thuringiensis RTI545 cells were evaluated in a choice feeding assay of corn seedlings and compared to a water control. Additional treatments compared to the water control were i) strain Bacillus thuringiensis subsp. kurstaki HD-1 (HD-1), ii) chemical control CAPTURE LFR (A.I.=17.15% bifenthrin), and iii) 869 medium. Filter paper was cut in half and each section placed in a petri dish, to which either treatment or deionized water was applied to each half of the paper. One germinated corn seed was situated on each moist filter paper half. Ten second-instar larvae were placed at the midline between treated and untreated filter paper. Dishes were sealed and maintained for 6 days. An image of the plate assay with the RTI545 cells after 6 days is shown in FIG. 4, and the data from all of the plate assays are summarized in Table IV. As was observed in the assay above for WPB, the RTI545 unexpectedly repelled, but did not kill the SCRW larvae. As can be seen in FIG. 4 and Table IV, the RTI545 cultures were excellent at repelling the SCRW larvae; 100% of the larvae were present on the water-treated half of the filter paper and none of the larvae on the RTI545 treated paper. In contrast, the larvae were statistically evenly divided between treatment and water control for the HD-1 strain. The chemical control resulted in about 19% of the larvae present on the treated filter paper. Table V shows similar results. The results show that the RTI545 strain was unexpectedly superior to the chemical insecticide at repelling the insects from the corn seed, but did not kill the insects.

Table VI compares the repellent effect on SCRW of kanosamine and B. thuringiensis strains RTI545 and FD30, showing that repellent behavior of RTI545 against insects may be due to production of kanosamine.

EXAMPLE 7 shows the repellent and egg-hatching inhibition of root-knot nematodes exposed to RTI545 supernatent, compared to kanosamine. The results summarized in Tables VII and VIII suggest that the effect of RTI545 against nematodes does not appear to be caused by production of kanosamine.

EXAMPLE 8 describes the positive effect on growth and yield in field and greenhouse trials under insect pressure by treating corn and soybean seed with spores of B. thuringiensis RTI545. The effects on growth, yield, and control of corn pests, wireworm and seed maggot, were measured in field trials in Wisconsin. Additional experiments were performed in the greenhouse to measure the effect on early plant growth in the presence of wireworm.

In a field trial experiment, corn seeds were treated with slurries containing: 1) chemical fungal control treatment comprising MAXIM+APRON XL (referred to as "FC"); 2) FC+ the insecticide bifenthrin 0.125 mg/seed; 3) FC+PONCHO 1250 (clothianidin 1.25 mg/seed) and VOTIVO (Bacillus firmus 1-1582); 4) FC+PONCHO 250 (clothianidin 0.25 mg/seed); 5) FC+PONCHO 500 (clothianidin 0.5 mg/seed) and VOTIVO (Bacillus firmus 1-1582) and; 6) FC+bifenthrin (0.125 mg/seed)+spores of B. thuringiensis RTI545. The treated corn seeds were planted in separate field trials in Wisconsin in soil infested wireworm and seed maggot. The results are shown below in Table IX. Inclusion of the B. thuringiensis RTI545 in combination with the insecticide bifenthrin resulted in significant improvements in percent emergence, plant stand, vigor and control of both wireworm and seed maggot over seeds treated with bifenthrin alone. In addition, the results of the combination of B. thuringiensis RTI545 and bifenthrin were statistically equivalent to the product PONCHO 1250 VOTIVO at controlling wireworm and showed an improvement over this product in controlling seed maggot. These data indicate that corn seed treatment with a combination of B. thuringiensis RTI545 and a chemical insecticide such as bifenthrin significantly improves insect control over inclusion of chemical insecticide alone and is superior to commercially available products for some types of insect control.

In a second field trial, corn seeds were treated with the same slurries as the first trial containing: 1) chemical control MAXIM+APRON XL (referred to as "FC"); 2) FC+Bifenthrin; 3) FC+PONCHO 1250 VOTIVO; 4) FC+PONCHO 250; and 5) FC+Bifenthrin+spores of RTI545. The treated corn seed were planted in separate field trials in Wisconsin with wireworm present but without seed maggot. Damage of corn roots from wireworm feeding were rated 41 days after planting. The results are shown below in Table X and show similar results to the previous trial. Specifically, inclusion of the B. thuringiensis RTI545 in combination with the insecticide bifenthrin resulted in significant improvements in percent emergence, plant stand, vigor and control of wireworm over seeds treated with bifenthrin alone. In addition, the results of the combination of B. thuringiensis RTI545 and bifenthrin were statistically equivalent or superior to the product PONCHO 1250 VOTIVO at controlling wireworm.

The average yield in the corn field trials after seed treatment with a combination of chemical insecticide and spores of RTI545 as compared to PONCHO VOTIVO was also determined. The results are shown below in Table XI. Inclusion of the B. thuringiensis RTI545 in combination with the insecticide bifenthrin resulted in significant improvements in yield as compared to seeds treated with bifenthrin alone. In addition, the combination of RTI545 and bifenthrin outperformed both PONCHO 500 VOTIVO and PONCHO 1250 VOTIVO by increasing yield 13 bushels/acre (from 180.5 to 193.7 and from 185.5 to 193.7 bushels/acre, respectively) representing a 6.8% and 4.2% increase in grain yield, respectively. These data indicate that corn seed treatment with a combination of RTI545 and a chemical insecticide such as bifenthrin significantly improves yield over inclusion of chemical insecticide alone, and reduces the need for in-furrow application of larger quantities of chemical insecticides to control damage by insects.

The effect on growth under insect pressure by treating corn seed with spores of RTI545 was further evaluated. In a set of greenhouse studies, corn seeds were first treated with the seed treatment slurries as described as follows and then planted in soil infested with the pest wireworm (10 wireworms per pot with one seed), along with a control set where the soil did not contain wireworm. The seed treatment slurries were as follows: 1) chemical control MAXIM+APRON XL (referred to as "FC"); 2) FC; 3) FC+Bifenthrin (0125 mg/seed for all treatments treated); 4) FC+Bifenthrin+RTI545 $5.0\times10^6$; 5) FC+Bifenthrin+RTI545 $5.0\times10^6$ heat-treated; 6) FC+Bifenthrin+RTI545 $1.0\times10^6$; 7) FC+RTI545 $5.0\times10^6$; and 8) FC+PONCHO 1250. The treated seeds were evaluated for percent emergence.

The results are shown below in Table XII. Inclusion of the B. thuringiensis RTI545 in combination with the insecticide bifenthrin resulted in 100% emergence, which was an improvement over inclusion of bifenthrin alone and provided results equivalent to the control without wireworm and the FC+PONCHO 1250 chemical treatment. Wireworm feeding prunes roots causing corn plant stunting and RTI545 alone or Bifenthrin with RTI545 reduced plant stunting in surviving plants. RTI545 alone exhibited activity on preventing plant loss but was inferior to insecticide bifenthrin in providing early protection against stunting. However, RTI545 was more effective in preventing plant stunting as the plants grew (data not shown). These data indicate that inclusion of spores of RTI545 in corn seed treatment, alone or in combination with a chemical insecticide such as bifenthrin, significantly improves plant health in the presence of the insect pest wireworm.

Experiments were performed to determine the effect on yield by treating soybean seed with a standard fungicidal combination of chemical active ingredients in addition to spores of B. thuringiensis RTI545, in combination with a chemical insecticide. The experiments were performed as described below. In the experiment, soybean seeds were mixed with a solution containing: 1) chemical control fludioxonil/TPM/mefenoxam ("FC"); 2) FC+insecticide thiamethoxam; and 3) FC+thiamethoxam+spores of B. thuringiensis RTI545. The treated soybean seeds were planted at three sites (N=3) that had wireworm infestation, and the yield was analyzed. The results are shown below in Table XIII. Inclusion of the RTI545 spores in combination with the thiamethoxam resulted in significant improvements in yield as compared to seeds treated with thiamethoxam alone. These data indicate that soybean seed treatment with a combination of RTI545 and a chemical insecticide significantly improves yield over inclusion of insecticide alone, and reduces the need for in-furrow application of larger quantities of chemical insecticides to control damage by insects.

EXAMPLE 9 describes the ability of the Bacillus thuringiensis RTI545 strain to reduce the nematode infestation in soybean and potato. A greenhouse study was performed with soybean plants potted in soil infected with Southern root-knot nematodes (Meloidogyne incognita) from seed treated with and without RTI545 cells. Seed treatment included products PONCHO VOTIVO (BAYER CROPSCIENCE LP; A.I.=40.3% clothianidin, 8.1% Bacillus firmus 1-1582) and AVICTA COMPLETE (SYNGENTA; A.I.=11.7% thiamethoxam, 10.3% abamectin, 2.34% thiabendazole, 0.3% fludioxonil, 0.23% mefenoxam, 0.12% azoxystrobin). The results are shown in Table XIV below. At 63 days after initiation, there was no statistical difference in the number of nematode eggs/pot for the seed treated with RTI545 cells and seed treated with the chemical combination AVICTA COMPLETE. However, the number of nematode eggs/pot for the seed treated with RTI545 cells was less than that for the seed treated with PONCHO VOTIVO. This demonstrates the positive effect on nematode control on soybean provided by Bacillus thuringiensis RTI545, providing equivalent to superior control as compared to commercially available biological plus chemical- and chemical active-based products.

A greenhouse study was performed with potato plants potted in soil naturally infected with Globodera sp. nematodes to determine the effect of treatment of the soil with Bacillus thuringiensis RTI545 cells. Potatoes (nematode sensitive variety "Bintje") were planted in soil infected with Globodera sp. (Control) and enhanced with $10^9$ cfu spores per liter of soil of RTI545. The results are shown in the graph in FIG. 5. Additional soil treatments were included in the study: VYDATE product (DUPONT; A.I.=Oxamyl [Methoyl N'N'-dimethyl-N-[(methyl carbamoyl)oxyl)oxy]-1-thiooxamimidate), BIOACT product (BAYER CROPSCIENCES LP; A.I.=Paecilomyces lilacinus strain 251), CAREX product (NUFARM, pyridaben), and Bacillus thuringiensis spp. kurstaki HD-1). The products were applied at the rates designated on the product labels. As can be seen in FIG. 5, the number of cysts per gram of root biomass for the soil treated with RTI545 cells was significantly reduced compared to all of the treatments including the products containing chemical active ingredients. This demonstrates the positive effect on nematode control for potato provided by Bacillus thuringiensis RTI545, providing superior control as compared to commercially available biological- and chemical active-based products.

EXAMPLE 10 describes experiments performed to investigate the effect on emergence, root disease, and yield in cotton in the presence of Rhizoctonia disease pressure when seeds were treated with the RTI545 strain in addition to chemical active agents for pathogen control.

Specifically, an experiment in cotton was set up as follows: 1) seed was untreated (UTC); 2) seed was treated with a base combination of fludioxonil+mefenoxam+imidacloprid according to manufacturer label (referred to as "B"); 3) seed was treated with base plus $5\times10^5$ cfu/seed of RTI545 (B+RTI545); and 4) seed was treated with base plus VIBRANCE (active ingredient sedaxane; SYNGENTA CROP PROTECTION, INC) according to label instructions (B+VIBRANCE). Field trials were performed in Georgia. The trials were inoculated with Rhizoctonia by mixing the dried inoculum with the seed at the time of planting to a prescribed rate to provide infection when the seed commenced to grow. The average percent cotton emergence is presented in Table XV below.

The results in Table XV show that treating with RTI545 spores in addition to the base resulted in significant improvement in percent emergence over that of the chemical base alone. In addition, treatment with RTI545 performed as well as the base plus commercial product VIBRANCE with chemical active. Thus, seed treatment with RTI545 can provide significant improvement in emergence even under conditions of severe pathogen pressure.

EXAMPLE 11 describes experiments to investigate the effect on growth and yield under insect pressure by wheat seed treated with spores of B. thuringiensis RTI545 and seeds treated with RTI545 plus chemical active agents for pathogen control. More specifically, the effects on growth, yield, and control of wheat pests, wireworm and white grub, were measured in field trials in Wisconsin. Wheat seeds were treated with slurries containing: 1) chemical fungicide base difenoconazole/tebuconazole/TPM/mefenoxan (referred to as "FC"); 2) FC+spores of B. thuringiensis RTI545 (RTI545 $1\times10^6$ cfu/g seed); 3) FC+bifenthrin (20 g/seed); 4) FC+bifenthrin (20 g/seed)+RTI545 $1\times10^6$ cfu/g seed; 5) FC+bifenthrin (50 g/seed); and 6) FC+bifenthrin (50 g/seed)+RTI545 $1\times10^6$ cfu/g seed. The results are shown below in Table XVI. Seed treatment with each of the B. thuringiensis RTI545 spores, and treatment with the RTI545 spores with either the fungicide base alone or in combination with the insecticide, bifenthrin, resulted in significant improvements in percent emergence, vigor, control of wireworm and white grub, and yield. In every case tested, inclusion of the RTI545 spores in the wheat seed treatment resulted in significant improvements in growth, vigor, pest control, and yield.

EXAMPLE 12 shows the impact of RTI545 soybean seed treatment on growth and yield against the Rhizoctonia fungal pathogen. Table XVII shows a comparison of RTI545 added to a base chemical seed treatment compared to the base treatment alone and to the base treatment plus another chemical active ingredient. Addition of RTI545 to the base chemical treatment resulted in significant increases in stand, vigor and yield compared to the chemical base.

EXAMPLE 13 shows the impact of RTI545 corn seed treatment on growth and yield against wireworms and seed maggots. Table XVIII shows that RTI545 provides some protection and enhances insecticidal protection against theses pests when added to chemical insecticides such as chlothinidin, bifenthrin and chlorantraniliprole.

EXAMPLE 14 shows that RTI545 is effective in in-furrow applications against corn wireworm and corn rootworm, resulting in increased yield and reduced root damage, alone and especially in combination with the chemical insecticide bifentrhrin, as shown in Tables XIX and XX.

EXAMPLE 15 shows the impact of RTI545 peanut seed treatment on growth and yield against the Rhizoctonia fungal pathogen. Table XXI shows a comparison of RTI545 added to a base chemical seed treatment compared to the base treatment alone. Addition of RTI545 to the base chemical treatment resulted in significant increases in stand, vigor and yield compared to the chemical base.

EXAMPLE 16 presents greenhouse assays of RTI545 corn seed treatment against lesion nematodes. Table XXII shows a comparison of RTI545 added to a base fungicide chemical seed treatment compared to the base treatment alone and the base treatment plus PONCHO/VOTIVO.

RTI545 plus the base treatment provided superior root length increase over the untreated compared to that provided by the base treatment plus PONCHO/VOTIVO. Table XXIII shows that RTI545+ base treatment provided superior reduction in penetration and fresh top weight compared to the base treatment and the base treatment+PONCHO/VOTIVO. This table also shows results when RT545 is combined with other biological control agents.

Example 17 presents soil drench assays of RTI545 soybean seed treatment against soybean cyst nematodes. Table XXIV shows a reduction of cysts compared to the untreated control.

EXAMPLES 18 and 19 show suspension concentrate formulations of RTI545 (Table XXV) and RTI545 plus bifenthrin (Tables XXVI and XXVII). Table XXVIII shows that the spores in an SC formulation remained stable over two weeks of storage at elevated temperature In one embodiment of the present disclosure, a composition is provided that includes a biologically pure culture of Bacillus thuringiensis RTI545 deposited as ATCC No. PTA-122161, or a mutant thereof having all the identifying characteristics thereof, for application to a plant for one or both of benefiting plant growth or conferring protection against a plant pest in a susceptible plant.

In another embodiment, a method is provided for one or both of benefiting growth of a plant or conferring protection against a plant pest in a susceptible plant, the method including delivering a composition comprising a biologically pure culture of Bacillus thuringiensis RTI545 deposited as ATCC No. PTA-122161, or a mutant thereof having all the identifying characteristics thereof to: a plant, plant part, seed of the plant, roots of the plant, soil or growth medium surrounding the plant or the seed of the plant, or soil or growth medium before planting the plant or sowing seed of the plant, in an amount suitable to benefit the plant growth and/or to confer protection against the plant pest in the susceptible plant.

In the compositions and methods of the present disclosure, the growth benefit of the plant and/or the conferred protection can be exhibited by improved seedling vigor, improved root development, improved plant growth, improved plant health, increased yield, improved appearance, improved resistance to plant pests, reduced pathogenic infection, or a combination thereof.

The compositions and methods of the present invention are beneficial to a wide range of plants including, but not limited to, monocots, dicots, cereals such as corn, sweet corn, popcorn, seed corn, silage corn, field corn, rice, wheat, barley, sorghum, asparagus, berries such as blueberry, blackberry, raspberry, loganberry, huckleberry, cranberry, gooseberry, elderberry, currant, caneberry, bushberry, brassica vegetables such as broccoli, cabbage, cauliflower, brussels sprouts, collards, kale, mustard greens, kohlrabi, cucurbit vegetables such as cucumber, cantaloupe, melon, muskmelon, squash, watermelon, pumpkin, eggplant, bulb vegetables such as onion, garlic, shallots, citrus such as orange, grapefruit, lemon, tangerine, tangelo, pummelo, fruiting vegetables such as pepper, tomato, ground cherry, tomatillo, okra, grape, herbs, spices, leafy vegetables such as lettuce, celery, spinach, parsley, radicchio, legumes or vegetables such as beans including green beans, snap beans, shell beans, soybeans, dry beans, garbanzo beans, lima beans, peas, chick peas, split peas, lentils, oil seed crops such as canola, castor, coconut, cotton, flax, oil palm, olive, peanut, rapeseed, safflower, sesame, sunflower, soybean, pome fruit such as apple, crabapple, pear, quince, mayhaw, root, tuber and corm vegetables such as carrot, potato, sweet potato, cassava, beets, ginger, horseradish, radish, ginseng, turnip, stone fruit such as apricot, cherry, nectarine, peach, plum, prune, strawberry, tree nuts such as almond, pistachio, pecan, walnut, filberts, chestnut, cashew, beechnut, butternut, macadamia, kiwi, banana, (blue) agave, grass, turf grass, ornamental plants, poinsettia, hardwood cuttings such as chestnut, oak, maple, sugarcane, and sugarbeet. In one or more embodiments, the plant can include corn, soybean, potato, cotton, tomato, pepper, cucurbits, sugarcane, peanut or wheat; or soybean, cotton, wheat, corn or potato.

In the compositions and methods of the present invention, the plant damage can be caused by a wide variety of plant pests including, for example, but not limited to, a plant insect pest, such as a Western Plant Bug (WPB) Lygus hesperus, Coleoptera sp., Diabrotica sp., including Western (D. virgifera), Southern (D. undecimpunctata) and Northern (D. barberi) corn rootworm), D. balteata, and D. longicornis, Melanotus spp. (including corn wireworm, Melanotus communis and Melanotus cribulosus), Phyllophaga spp. (including white grubs, wireworms, false wireworms and Phyllophaga rugosa), Limonius spp. (sugarbeet wireworms and Limonius agronus), Agriotes spp. (including wheat wireworms Agriotes mancus, corn wireworms, white grubs and Seed maggots), Lepidoptera sp., Peridroma spp. (including variegated cutworm), Euxoa spp. (including army cutworm), Agrotis spp. (including black cutworm Agrotis ipsilon), Diptera sp., Hylemya spp. (including seedcorn maggot Delia platura Meigen and Hylemya cilicrura), Tetanops spp. (including sugarbeet root maggot), Homoptera sp., Pemphigus sp. (including sugarbeet root aphid, cutworm, and white grub), Aphis spp. (including corn root aphid), seed-corn beetle Agonoderus lecontei, Feltia subgothica, or combinations thereof. Notable insects include Western plant bug, Southern corn rootworm, corn wireworm, seedcorn maggot, seed maggot, wheat wireworm and white grub.

In the compositions and methods of the present invention, the plant pest can be, for example, but not limited to, a plant pathogenic nematode, a reniform nematode, Rotlyenchulus spp., dagger nematode, Xiphinema spp., lance nematode, Hoplolaimus spp., pin (lesion) nematode, Paratylenchus spp., ring nematode, Criconemoides spp., root-knot nematode, Meloidogyne spp., sheath nematode, Hemicycliophora spp., spiral nematode, Helicotylenchus spp., stubbyroot nematode, Trichodorus spp., cyst nematode, Heterodera spp. and Globodera spp., sting nematode, Belonolaimus spp., stunt nematode, and Tylenchorhynchus spp., burrowing nematode, Radopholus spp. or combinations thereof. Notable nematodes include root-knot nematodes (Meloidogyne spp.), lesion nematodes, (Paratylenchus spp.) and cyst nematodes (Heterodera spp. and Globodera spp.).

In the compositions and methods of the present invention, the plant pest can be characterized by, for example, but not limited to, a plant fungal pathogen or a plant bacterial pathogen, such as a rust fungus, a Botrytis spp., an Erwinia spp., a Dickeya spp., an Agrobacterium spp., a Xanthomonas spp., a Xylella spp., a Candidatus spp., a Fusarium spp., a Sclerotinia spp., a Cercospora/Cercosporidium spp., an Uncinula spp., a Podosphaera spp. (Powdery Mildew), a Phomopsis spp., an Alternaria spp., a Pseudomonas spp., a Phytophthora spp., a Phakopsora spp., an Aspergillus spp., a Uromyces spp., such as Uromyces appendiculatus, a Cladosporium spp., a Rhizopus spp., a Penicillium spp., a Rhizoctonia spp., Macrophomina phaseolina, a, a Mycosphaerella spp., a Magnaporthe spp., such as Magnaporthe oryzae or Magnaporthe grisea, a Monilinia spp., a Colletotrichum spp., a Diaporthe spp., a Corynespora spp., a Gymnosporangium spp., a Schizothyrium spp., a Gloeodes spp., a Botryosphaeria spp., a Neofabraea spp., a Wilsonomyces spp., a Sphaerotheca spp., a Erysiphe spp., a Stagonospora spp., a Pythium spp., a Venturia spp., a Ustilago spp., a Claviceps spp., a Tilletia spp., a Phoma spp., Cocliobolus sativus, Gaeumanomyces gaminis, a Rhynchosporium spp., a Biopolaris spp., and a Helminthosporium spp., or combinations thereof.

Notable fungal pathogens include Aspergillus flavus, Botrytis spp. such as Botrytis cinerea, Fusarium spp., such as Fusarium colmorum, Fusarium oxysporum or Fusarium virguliforme, Phytophthora spp. such as Phytophthora capsici, Rhizoctonia spp. such as Rhizoctonia solani, Magnaporthe spp., such as Magnaporthe grisea and Magnaporthe oryzae, and Pythium spp. such as Pythium aphanidermatum and Pythium sylvatium, Monilinia spp. such as Monilinia fructicola, Colletotrichum spp., such as Colletotrichum gloeosporioides (sexual stage Glomerella cingulata) i.e. anthracnose, Sclerotinia spp., such as Sclerotinia sclerotiorum and Sclerotinia homeocarpa; more notably Rhizoctonia spp. Notable bacterial pathogens include Erwinia spp. such as Erwinia amylovora.

In the compositions and methods of the present disclosure, the compositions including the RTI545 strain can be in the form of a liquid, a suspension concentrate, an oil dispersion, a dust, a dry wettable powder, a spreadable granule, or a dry wettable granule. In embodiments, the Bacillus thuringiensis RTI545 can be present in the composition at a concentration of from about $1.0\times10^{8}$ CFU/ml to about $1.0\times10^{12}$ CFU/ml. In embodiments, the Bacillus thuringiensis RTI545 can be present in an amount of from about $1.0\times10^{8}$ CFU/g to about $1.0\times10^{12}$ CFU/g. The Bacillus thuringiensis RTI545 can be in the form of spores or vegetative cells.

In the compositions and methods of the present disclosure, the composition including the RTI545 strain can include one or a combination of adjuvants including for example a carrier, a binder, a surfactant, a dispersant, or a yeast extract. The carrier, binder, surfactant, dispersant, and/or yeast extract are included to improve the properties of the composition for use in benefiting plant growth and or conferring protection against plant pests, the properties including one or more of improved handling properties, improved wettability, improved flowability, improved adhesion to seed, improved stability of the RTI545 strain, and improved activity of the RTI545 strain after delivery or application to the plant seed, roots, or soil. The yeast extract can be delivered at a rate for benefiting plant growth ranging from about 0.01% to 0.2% w/w.

The compositions including the RTI545 strain can be in the form of a planting matrix. The planting matrix can be in the form of a potting soil mixture.

In the compositions and methods of the present disclosure, the composition can further include one or a combination of an additional agricultural agent, such as an insecticide, fungicide, nematicide, bacteriocide, biostimulant, herbicide, plant extract, microbial extract, plant growth regulator, fertilizer or crop nutrient product present in an amount suitable to benefit the plant growth and/or to confer protection against the plant pest in the susceptible plant. In one embodiment, the composition including the biologically pure culture of Bacillus thuringiensis RTI545 and the one or a combination of the insecticide, fungicide, nematicide, bacteriocide, biostimulant, herbicide, plant extract, microbial extract, plant growth regulator, fertilizer or crop nutrient product, are formulated together. Any of the additional agricultural agents may be a biological agent or a chemical agent. In other embodiments the composition comprising the RTI545 strain is formulated separately from the additional agricultural agent, which may also be formulated, and then mixed with the additional agricultural agent, such as in a tank mix.

The fertilizer can be a liquid fertilizer. The term "liquid fertilizer" refers to a fertilizer in a fluid or liquid form containing various ratios of nitrogen, phosphorous and potassium (for example, but not limited to, 5 to 15%, such as 10%, of nitrogen, 20 to 50%, such as 34%, of phosphorous and 0 to 15%, such as 0%, of potassium) and optionally secondary nutrients and/or micronutrients, commonly known as starter fertilizers that are high in phosphorus and promote rapid and vigorous root growth.

As used herein, the term "biostimulant" refers to a substance or microorganism applied to plants with the aim of enhancing nutrient uptake, nutrition efficiency, and/or abiotic stress tolerance to improve crop vigor, yields and/or crop quality traits such as nutritional content, appearance and shelf-life, regardless of its nutrient content. Biostimulants operate through different mechanisms than fertilizers and do not have direct action against pest or diseases.

In one embodiment, the composition including the biologically pure culture of Bacillus thuringiensis RTI545 further comprises the chemical insecticide bifenthrin.

Of note are mixtures of the Bacillus thuringiensis RTI545 strain with other biocontrol strains including other Bacillus thuringiensis strains such as Bacillus thuringiensis subsp. aizawai or Bacillus thuringiensis subsp. kurstaki, Bacillus subtilis strains such as CH201 or QST713 or MBI600 or RTI477, Bacillus licheniformis strains such as CH200 or RTI184, Bacillus velezensis strains such as RTI301, Bacillus subtilis var. amyloliquefaciens FZB24, or Bacillus amyloliquefaciens D747, or combinations thereof.

Mixtures of microbial strains, including RTI545, can be used to enhance activity against specific target pests, but can also be used to enhance the spectrum of utility. As an example, combining a strain with strong activity against soil insects with other strains that have strong activity against nematodes, fungi, or strong plant growth benefits can be combined. Furthermore, such mixtures of strains can also be combined with synthetic (chemical) pesticides for added benefits.

In one embodiment, the composition including the biologically pure culture of Bacillus thuringiensis RTI545 further comprises a strain previously identified as Bacillus amyloliquefaciens RTI301 deposited as ATCC No. PTA-121165 (See US2016/0186273). This strain has recently been reclassified as a Bacillus velezensis strain. In the remainder of this specification, the strain deposited as ATCC No. PTA-121165 will be referred to as "RTI301" or "Bacillus velezensis RTI301". In one embodiment, the combination of the RTI545 and the RTI301 strains extends the benefit to plant growth and protection against plant pests by widening and increasing the temperature range in which one or both of the strains provide maximum protection against plant pests, including plant fungal pathogens.

In other embodiments, the composition including the biologically pure culture of Bacillus thuringiensis RTI545 further comprises a biologically pure culture of a Bacillus licheniformis CH200 deposited as DSM 17236, or a mutant thereof having all the identifying characteristics thereof; a biologically pure culture of a Bacillus subtilis CH201 deposited as DSM 17231, or a mutant thereof having all the identifying characteristics thereof; a biologically pure culture of a Bacillus subtilis RTI477 deposited as ATCC No. PTA-121167, or a mutant thereof having all the identifying characteristics thereof; a biologically pure culture of a Bacillus amyloliquefaciens D747 strain deposited as FERM BP-8234; a Bacillus licheniformis RTI184 deposited as ATCC No. PTA-121722, or a mutant thereof having all the identifying characteristics thereof or any combination thereof, including combinations also comprising RTI301.

In one embodiment, the composition including the biologically pure culture of Bacillus thuringiensis RTI545 further comprises the chemical insecticide, bifenthrin, and the composition is delivered in combination with a liquid fertilizer to: a plant, plant part, seed of the plant, roots of the plant, soil or growth medium surrounding the plant or the seed of the plant, or soil or growth medium before planting the plant or sowing seed of the plant. Examples of using the insecticide, bifenthrin, in combination with a liquid fertilizer to benefit plant growth are described, for example, in WO 2016/108972 A1, which is herein incorporated by reference in its entirety.

In another embodiment, a method is provided for one or both of benefiting growth of a plant or conferring protection against a plant pest in a susceptible plant, the method comprising: delivering to a plant, plant part, seed of the plant, roots of the plant, soil or growth medium surrounding the plant or the seed of the plant, or soil or growth medium before planting the plant or sowing seed of the plant, a combination of: a composition comprising a biologically pure culture of Bacillus thuringiensis RTI545 deposited as ATCC No. PTA-122161, or a mutant thereof having all the identifying characteristics thereof in an amount suitable to benefit the plant growth and/or to confer protection against the plant pest in the susceptible plant; and one or a combination of additional agricultural agents such as an insecticide, fungicide, nematicide, bacteriocide, herbicide, plant extract, plant growth regulator, or fertilizer as described herein in an amount suitable to benefit the plant growth and/or to confer protection against the plant pest in the susceptible plant. Any of the additional agricultural agents may be a biological agent or a chemical agent. In this embodiment, the composition including the biologically pure culture of Bacillus thuringiensis RTI545 and the one or a combination of additional agricultural agent(s) as described herein, are delivered separately to the susceptible plant, rather than from a single formulation.

In one embodiment, the composition including the biologically pure culture of Bacillus thuringiensis RTI545 is delivered in combination with a liquid fertilizer to: plant, plant part, seed of the plant, roots of the plant, soil or growth medium surrounding the plant or the seed of the plant, or soil or growth medium before planting the plant or sowing seed of the plant.

In one embodiment, the composition including the biologically pure culture of Bacillus thuringiensis RTI545 is delivered in combination with the chemical insecticide, bifenthrin, and with the liquid fertilizer to: plant, plant part, seed of the plant, roots of the plant, soil or growth medium surrounding the plant or the seed of the plant, or soil or growth medium before planting the plant or sowing seed of the plant.

In one embodiment, a plant seed is provided that is coated with a composition comprising an additional biological agricultural agent, such as: spores of a biologically pure culture of Bacillus velezensis RTI301 deposited as ATCC No. PTA-121165, or a mutant thereof having all the identifying characteristics thereof, present in an amount suitable to benefit plant growth and/or to confer protection against a plant pest in a susceptible plant. The composition can include an amount of Bacillus velezensis spores from about $1.0\times10^2$ CFU/seed to about $1.0\times10^9$ CFU/seed.

The coated seed compositions of the present invention are beneficial to a wide range of plant seeds including, but not limited to, the seed of monocots, dicots, cereals such as corn, sweet corn, popcorn, seed corn, silage corn, field corn, rice, wheat, barley, sorghum, asparagus, berries such as blueberry, blackberry, raspberry, loganberry, huckleberry, cranberry, gooseberry, elderberry, currant, caneberry, bushberry, brassica vegetables such as broccoli, cabbage, cauliflower, brussels sprouts, collards, kale, mustard greens, kohlrabi, cucurbit vegetables such as cucumber, cantaloupe, melon, muskmelon, squash, watermelon, pumpkin, eggplant, bulb vegetables such as onion, garlic, shallots, citrus such as orange, grapefruit, lemon, tangerine, tangelo, pummelo, fruiting vegetables such as pepper, tomato, ground cherry, tomatillo, okra, grape, herbs, spices, leafy vegetables such as lettuce, celery, spinach, parsley, radicchio, legumes or vegetables such as beans including green beans, snap beans, shell beans, soybeans, dry beans, garbanzo beans, lima beans, peas, chick peas, split peas, lentils, oil seed crops such as canola, castor, coconut, cotton, flax, oil palm, olive, peanut, rapeseed, safflower, sesame, sunflower, soybean, pome fruit such as apple, crabapple, pear, quince, mayhaw, root, tuber and corm vegetables such as carrot, potato, sweet potato, cassava, beets, ginger, horseradish, radish, ginseng, turnip, stone fruit such as apricot, cherry, nectarine, peach, plum, prune, strawberry, tree nuts such as almond, pistachio, pecan, walnut, filberts, chestnut, cashew, beechnut, butternut, macadamia, kiwi, banana, (blue) agave, grass, turf grass, ornamental plants, poinsettia, hardwood cuttings such as chestnuts, oak, maple, sugarcane, and sugarbeet. In one or more embodiments, the plant seed can include corn, soybean, potato, cotton, tomato, pepper, cucurbits, sugarcane, peanut or wheat; or soybean, cotton, wheat, corn or potato.

In one embodiment of the plant seed coated with the composition, the composition further comprises one or a combination of additional agricultural agent(s) as described herin present in an amount suitable to benefit plant growth and/or to confer protection against the plant pest in the susceptible plant.

In one embodiment, a method is provided for one or both of benefiting growth of a plant or conferring protection against a plant pest in a susceptible plant, the method comprising: planting a seed of the plant, wherein the seed has been coated with a composition comprising a biologically pure culture of Bacillus thuringiensis RTI545 deposited as ATCC PTA-122161, or a mutant thereof having all the identifying characteristics thereof, wherein growth of the plant from the seed is benefited and/or protection against the plant pest is conferred.

In one embodiment, the method further includes delivering a liquid fertilizer to the coated seed of the plant, soil or growth medium surrounding the coated seed of the plant, or soil or growth medium before planting the coated seed of the plant.

In one embodiment of the method, the plant seed is coated with the composition further comprising an additional biological agricultural agent, such as Bacillus velezensis RTI301 deposited as ATCC No. PTA-121165. In one embodiment, the combination of the RTI545 and the RTI301 strains extends the benefit to plant growth and protection against plant pests by widening and increasing the temperature range in which one or both of the strains provide maximum protection against plant pests, including plant fungal pathogens.

In one embodiment, the plant seed is coated with the composition further comprising a chemical insecticide, and the method further includes delivering a liquid fertilizer to the coated seed of the plant, soil or growth medium surrounding the coated seed of the plant, or soil or growth medium before planting the coated seed of the plant. In one embodiment, the chemical insecticide is bifenthrin.

In embodiments herein comprising coated seeds, the term "seed" refers not only to true seeds but also other plant parts for propagating the plant such as seedlings, transplants, cuttings (e.g. stems, roots, leaves, and the like), spores, setts (e.g. of sugarcane), bulbs, corms, rhizomes, tubers, or portions thereof, or other plant tissue from which a complete plant can be obtained.

In the compositions and methods of the present disclosure, the composition can include a fungicide. The fungicide can include an extract from Lupinus albus. In one or more embodiments, the fungicide can include a BLAD polypeptide. The BLAD polypeptide can be a fragment of the naturally occurring seed storage protein from sweet lupine (Lupinus albus) that acts on susceptible fungal pathogens by causing damage to the fungal cell wall and disrupting the inner cell membrane. The compositions can include about 20% of the BLAD polypeptide.

In addition, in one or more embodiments, suitable insecticides, herbicides, fungicides, and nematicides of the compositions and methods of the present invention can include the following:

Insecticides: A0) various insecticides, including agrigata, al-phosphide, amblyseius, aphelinus, aphidius, aphidoletes, artimisinin, autographa californica NPV, azocyclotin, Bacillus subtilis, Bacillus thuringiensis subsp. aizawai, Bacillus thuringiensis subsp. kurstaki, Bacillus thuringiensis, Beauveria, Beauveria bassiana, betacyfluthrin, biologicals, bisultap, brofluthrinate, bromophos-e, bromopropylate, Bt-Corn-GM, Bt-Soya-GM, capsaicin, cartap, celastrus-extract, chlorantraniliprole, chlorbenzuron, chlorethoxyfos, chlorfluazuron, chlorpyrifos-e, cnidiadin, cryolite, cyanophos, cyantraniliprole, cyclaniliprole, cyhalothrin, cyhexatin, cypermethrin, dacnusa, DCIP, dichloropropene, dicofol, diglyphus, diglyphus+dacnusa, dimethacarb, dithioether, dodecyl-acetate, emamectin, encarsia, EPN, eretmocerus, ethylene-dibromide, eucalyptol, fatty-acids, fatty-acids/salts, fenazaquin, fenobucarb (BPMC), fenpyroximate, flubrocythrinate, flufenzine, flupyradifurone, formetanate, formothion, furathiocarb, gamma-cyhalothrin, garlic-juice, granulosis-virus, harmonia, heliothis armigera NPV, inactive bacterium, indol-3-ylbutyric acid, iodomethane, iron, isocarbofos, isofenphos, isofenphos-m, isoprocarb, isothioate, kaolin, lindane, liuyangmycin, matrine, mephosfolan, metaldehyde, metarhizium-anisopliae, methamidophos, metolcarb (MTMC), mineral-oil, mirex, m-isothiocyanate, monosultap, myrothecium verrucaria, naled, neochrysocharis formosa, nicotine, nicotinoids, oil, oleic-acid, omethoate, orius, oxymatrine, paecilomyces, paraffin-oil, parathion-e, pasteuria, petroleum-oil, pheromones, phosphorus-acid, photorhabdus, phoxim, phytoseiulus, pirimiphos-e, plant-oil, plutella xylostella GV, polyhedrosis-virus, polyphenol-extracts, potassium-oleate, profenofos, prosuler, prothiofos, pyraclofos, pyrethrins, pyridaphenthion, pyrimidifen, pyriproxifen, quillay-extract, quinomethionate, rape-oil, rotenone, saponin, saponozit, sodium-compounds, sodium-fluosilicate, starch, steinernema, streptomyces, sulfluramid, sulphur, tebupirimfos, temephos, tetradifon, tetraniliprole, thiofanox, thiometon, transgenics (e.g., Cry3Bb1), triazamate, trichoderma, trichogramma, triflumuron, verticillium, vertrine, isomeric insecticides (e.g., kappa-bifenthrin, kappa-tefluthrin), dichoromezotiaz, broflanilide, pyrazifluumid; A1) the class of carbamates, including aldicarb, alanycarb, benfuracarb, carbaryl, carbofuran, carbosulfan, methiocarb, methomyl, oxamyl, pirimicarb, propoxur and thiodicarb; A2) the class of organophosphates, including acephate, azinphos-ethyl, azinphos-methyl, chlorfenvinphos, chlorpyrifos, chlorpyrifos-methyl, demeton-S-methyl, diazinon, dichlorvos/DDVP, dicrotophos, dimethoate, disulfoton, ethion, fenitrothion, fenthion, isoxathion, malathion, methamidaphos, methidathion, mevinphos, monocrotophos, oxymethoate, oxydemeton-methyl, parathion, parathion-methyl, phenthoate, phorate, phosalone, phosmet, phosphamidon, pirimiphos-methyl, quinalphos, terbufos, tetrachlorvinphos, triazophos and trichlorfon; A3) the class of cyclodiene organochlorine compounds such as endosulfan; A4) the class of fiproles, including ethiprole, fipronil, pyrafluprole and pyriprole; A5) the class of neonicotinoids, including acetamiprid, clothianidin, dinotefuran, imidacloprid, nitenpyram, thiacloprid and thiamethoxam; A6) the class of spinosyns such as spinosad and spinetoram; A7) chloride channel activators from the class of mectins, including abamectin, emamectin benzoate, ivermectin, lepimectin and milbemectin; A8) juvenile hormone mimics such as hydroprene, kinoprene, methoprene, fenoxycarb and pyriproxyfen; A9) selective homopteran feeding blockers such as pymetrozine, flonicamid and pyrifluquinazon; A10) mite growth inhibitors such as clofentezine, hexythiazox and etoxazole; A11) inhibitors of mitochondrial ATP synthase such as diafenthiuron, fenbutatin oxide and propargite; uncouplers of oxidative phosphorylation such as chlorfenapyr; A12) nicotinic acetylcholine receptor channel blockers such as bensultap, cartap hydrochloride, thiocyclam and thiosultap sodium; A13) inhibitors of the chitin biosynthesis type 0 from the benzoylurea class, including bistrifluron, diflubenzuron, flufenoxuron, hexaflumuron, lufenuron, novaluron and teflubenzuron; A14) inhibitors of the chitin biosynthesis type 1 such as buprofezin; A15) molting disruptors such as cyromazine; A16) ecdyson receptor agonists such as methoxyfenozide, tebufenozide, halofenozide and chromafenozide; A17) octopamin receptor agonists such as amitraz; A18) mitochondrial complex electron transport inhibitors pyridaben, tebufenpyrad, tolfenpyrad, flufenerim, cyenopyrafen, cyflumetofen, hydramethylnon, acequinocyl or fluacrypyrim; A19) voltage-dependent sodium channel blockers such as indoxacarb and metaflumizone; A20) inhibitors of the lipid synthesis such as spirodiclofen, spiromesifen and spirotetramat; A21) ryanodine receptor-modulators from the class of diamides, including flubendiamide, the phthalamide compounds (R)-3-

Chlor-N1-{2-methyl-4-[1,2,2,2-tetrafluor-1-(trifluormethyl)ethyl]phenyl}-N2-(1-methyl-2-methylsulfonylethyl) phthalamid and (S)-3-Chlor-N1-{2-methyl-4-[1,2,2,2-tetrafluor-1-(trifluormethyl)ethyl]phenyl}-N2-(1-methyl-2-methylsulfonylethyl)phthalamid, chlorantraniliprole, cyclaniliprole and cyantraniliprole; A22) compounds of unknown or uncertain mode of action such as azadirachtin, amidoflumet, bifenazate, fluensulfone, piperonyl butoxide, pyridalyl, sulfoxaflor; or A23) sodium channel modulators from the class of pyrethroids, including acrinathrin, allethrin, bifenthrin, cyfluthrin, lambda-cyhalothrin, cypermethrin, alpha-cypermethrin, beta-cypermethrin, zeta-cypermethrin, deltamethrin, esfenvalerate, etofenprox, fenpropathrin, fenvalerate, flucythrinate, tau-fluvalinate, permethrin, silafluofen, tefluthrin and tralomethrin.

Of note are mixtures of the Bacillus thuringiensis RTI545 strain with other biocontrol strains including Bacillus subtilis strains such as CH201, Bacillus licheniformis strains such as CH200, other Bacillus thuringiensis strains such as Bacillus thuringiensis subsp. aizawai, Bacillus thuringiensis subsp. kurstaki, or combinations thereof for insect control.

In the compositions and methods of the present disclosure, the composition can include a chemical insecticide. The chemical insecticide can include a pyrethroid such as bifenthrin, tefluthrin, zeta-cypermethrin, cyfluthrin; an organophosphate such as chlorethoxyphos, chlorpyrifos, tebupirimphos, fiproles such as fipronil; neonicotinoids such as imidacloprid, thiamethoxam, clothianidin; diamides such as chlorantraniliprole, cyantraniliprole, cyclaniliprole; or mixtures thereof.

Preferred are mixtures of the Bacillus thuringiensis RTI545 strain with chemical insect control agents comprising chlorantraniliprole, chlorethoxyfos, chlorpyrifos-e, cyantraniliprole, cyclaniliprole, cypermethrin, dichloropropene, flupyradifurone, gamma-cyhalothrin, profenofos, tebupirimfos, tefluthrin, kappa-bifenthrin, kappa-tefluthrin, carbofuran, carbosulfan, oxamyl, thiodicarb, chlorpyrifos, chlorpyrifos-e, chlorpyrifos-methyl, diazinon, phorate, terbufos, fipronil, acetamiprid, clothianidin, imidacloprid, thiacloprid, thiamethoxam, abamectin, flonicamid, flubendiamide, bifenthrin, lambda-cyhalothrin, cypermethrin, zeta-cypermethrin, deltamethrin, or any mixtures thereof.

More preferred are mixtures of the Bacillus thuringiensis RTI545 strain with clothianidin, thiamethoxam, imidacloprid, tefluthrin, fipronil, chlorpyrifos-e, tebupirimfos, bifenthrin, cypermethrin, zeta-cypermethrin, gamma-cyhalothrin, oxamyl, chlorantraniliprole, cyantraniliprole, cyclaniliprole, or mixtures thereof.

In one or more embodiments, the insecticide can comprise bifenthrin and the composition can be formulated as a liquid. In one or more embodiments, the insecticide can comprise bifenthrin and clothianidin. In one or more embodiments, the insecticide can comprise bifenthrin and clothianidin and the composition can be formulated as a liquid. In one or more embodiments, the insecticide can comprise bifenthrin or zeta-cypermethrin. In one or more embodiments, the composition can be formulated as a liquid and the insecticide can comprise bifenthrin or zeta-cypermethrin.

In one embodiment, the chemical insecticide includes bifenthrin. In one embodiment, the chemical insecticide includes bifenthrin and the composition further includes a hydrated aluminum-magnesium silicate, and at least one dispersant selected from the group consisting of a sucrose ester, a lignosulfonate, an alkylpolyglycoside, a naphthalenesulfonic acid formaldehyde condensate and a phosphate ester. The bifenthrin insecticide can be present at a concentration ranging from 0.1 g/ml to 0.2 g/ml. The bifenthrin insecticide can be present at a concentration of 0.17 g/ml. The rate of application of the bifenthrin insecticide can be in the range of from about 0.1 gram of bifenthrin per hectare (g ai/ha) to about 1000 g ai/ha, more preferably in a range of from about 1 g ai/ha to about 100 g ai/ha.

The bifenthrin can be preferably present in a concentration of from 1.0% by weight to 35% by weight, more particularly, from 15% by weight to 25% by weight based upon the total weight of all components in the composition. The bifenthrin insecticide composition can be formulated in a manner suitable for mixture as a liquid with a fertilizer.

Fungicides: B0) benzovindiflupyr, anitiperonosporics (such as ametoctradin, amisulbrom, benthiavalicarb, cyazofamid, cymoxanil, dimethomorph, ethaboxam, famoxadone, fenamidone, flumetover, flumorph, fluopicolide, iprovalicarb, mandipropamid, valifenalate, benalaxyl, benalaxyl-M, furalaxyl, metalaxyl, and metalaxyl-M), ametoctradin, amisulbrom, copper salts (e.g., copper hydroxide, copper oxychloride, copper sulfate, copper persulfate), boscalid, thiflumazide, flutianil, furalaxyl, thiabendazole, benodanil, mepronil, isofetamid, fenfuram, bixafen, fluxapyroxad, penflufen, sedaxane, coumoxystrobin, enoxastrobin, flufenoxystrobin, pyraoxystrobin, pyrametostrobin, triclopyricarb, fenaminstrobin, metominostrobin, pyribencarb, meptyldinocap, fentin acetate, fentin chloride, fentin hydroxide, oxytetracycline, chlozolinate, chloroneb, tecnazene, etridiazole, iodocarb, prothiocarb, various Bacillus strains (e.g., strains identified as CH200, CH201, RTI184, RTI301, QST713, FZB24, MBI600, D747), extract from Melaleuca alternifolia, extract from Lupinus albus doce, BLAD polypeptide, pyrisoxazole, oxpoconazole, etaconazole, fenpyrazamine, fenpicoxamide, mefentrifluconazole, naftifine, terbinafine, validamycin, pyrimorph, valifenalate, fthalide, probenazole, isotianil, laminarin, extract from Reynoutria sachalinensis, phosphorous acid and salts, teclofthalam, triazoxide, pyriofenone, organic oils, potassium bicarbonate, chlorothalonil, fluoroimide; B1) azoles, including bitertanol, bromuconazole, cyproconazole, difenoconazole, diniconazole, enilconazole, epoxiconazole, fluquinconazole, fenbuconazole, flusilazole, flutriafol, hexaconazole, imibenconazole, ipconazole, metconazole, myclobutanil, penconazole, propiconazole, prothioconazole, simeconazole, triadimefon, triadimenol, tebuconazole, tetraconazole, triticonazole, prochloraz, pefurazoate, imazalil, triflumizole, cyazofamid, benomyl, carbendazim, thiabendazole, fuberidazole, ethaboxam, etridiazole and hymexazole, azaconazole, diniconazole-M, oxpoconazol, paclobutrazol, uniconazol, 1-(4-chloro-phenyl)-2-([1,2,4]triazol-1-yl)-cycloheptanol and imazalilsulfphate; B2) strobilurins, including azoxystrobin, dimoxystrobin, enestroburin, fluoxastrobin, kresoxim-methyl, methominostrobin, orysastrobin, picoxystrobin, pyraclostrobin, trifloxystrobin, enestroburin, methyl (2-chloro-5-[1-(3-methylbenzyloxyimino)ethyl]benzyl)carbamate, methyl (2-chloro-5-[1-(6-methylpyridin-2-ylmethoxyimino)ethyl]benzyl)carbamate and methyl 2-(ortho-(2,5-dimethylphenyloxymethylene)-phenyl)-3-methoxyacrylate, 2-(2-(6-(3-chloro-2-methyl-phenoxy)-5-fluoro-pyrimidin-4-yloxy)-phenyl)-2-methoxyimino-N-methyl-acetamide and 3-methoxy-2-(2-(N-(4-methoxy-phenyl)-cyclopropanecarboximidoylsulfanylmethyl)-phenyl)-acrylic acid methyl ester; B3) carboxamides, including carboxin, benalaxyl, benalaxyl-M, fenhexamid, flutolanil, furametpyr, mepronil, metalaxyl, mefenoxam, ofurace, oxadixyl, oxycarboxin, penthiopyrad, isopyrazam, thifluzamide, tiadinil, 3,4-dichloro-N-(2-cyanophenyl)isothiazole-5-carboxamide, dimethomorph, flumorph, flumetover, fluopicolide (picobenzamid), zoxamide, carpropamid, diclocymet, mandipropamid, N-(2-(4-[3-(4-chlorophenyl)prop-2-ynyloxy]-3-methoxyphenyl)ethyl)-2-methanesulfonyl-amino-3-methylbutyramide, N-(2-(4-[3-(4-chloro-phenyl)prop-2-ynyloxy]-3-methoxy-phenyl) ethyl)-2-ethanesulfonylamino-3-methylbutyramide, methyl 3-(4-chlorophenyl)-3-(2-isopropoxycarbonylamino-3-methyl-butyrylamino)propionate, N-(4'-bromobiphenyl-2-yl)-4-difluoromethyl-2-methylthiazole-5-carboxamide, N-(4'-trifluoromethyl-biphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3',4'-dichloro-4-fluorobiphenyl-2-yl)-3-difluoromethyl-1-methylpyrazole-4-carboxamide, N-(3',4'-dichloro-5-fluorobiphenyl-2-yl)-3-difluoromethyl-1-methylpyrazole-4-carboxamide, N-(2-cyano-phenyl)-3,4-dichloroisothiazole-5-carboxamide, 2-amino-4-methylthiazole-5-carboxanilide, 2-chloro-N-(1,1,3-trimethyl-indan-4-yl)-nicotinamide, N-(2-(1,3-dimethylbutyl)-phenyl)-1,3-dimethyl-5-fluoro-1H-pyrazole-4-carboxamide, N-(4'-chloro-3',5-difluorobiphenyl-2-yl)-3-difluoromethyl-1-methyl-1H-pyrazole-4-carboxamide, N-(4'-chloro-3',5-difluoro-biphenyl-2-yl)-3-trifluoromethyl-1-methyl-1H-pyrazole-4-carboxamide, N-(3',4'-dichloro-5-fluorobiphenyl-2-yl)-3-trifluoromethyl-1-methyl-1H-pyrazole-4-carboxamide, N-(3',5-difluoro-4'-methyl-biphenyl-2-yl)-3-difluoromethyl-1-methyl-1H-pyrazole-4-carboxamide, N-(3',5-difluoro-4'-methyl-biphenyl-2-yl)-3-trifluoromethyl-1-methyl-1H-pyrazole-4-carboxamide, N-(cis-2-bicyclopropyl-2-yl-phenyl)-3-difluoromethyl-1-methyl-1H-pyrazole-4-carboxamide, N-(trans-2-bicyclopropyl-2-yl-phenyl)-3-difluoro-methyl-1-methyl-1H-pyrazole-4-carboxamide, fluopyram, N-(3-ethyl-3,5-5-trimethyl-cyclohexyl)-3-formylamino-2-hydroxy-benzamide, oxytetracyclin, silthiofam, N-(6-methoxy-pyridin-3-yl) cyclopropanecarboxamide, 2-iodo-N-phenyl-benzamide, N-(2-bicyclopropyl-2-yl-phenyl)-3-difluormethyl-1-methylpyrazol-4-ylcarboxamide, N-(3',4',5'-trifluorobiphenyl-2-yl)-1,3-di methyl pyrazol-4-ylcarboxamide, N-(3',4',5'-trifluorobiphenyl-2-yl)-1,3-dimethyl-5-fluoropyrazol-4-yl-carboxamide, N-(3',4',5'-trifluorobiphenyl-2-yl)-5-chloro-1,3-dimethyl-pyrazol-4-ylcarboxamide, N-(3',4',5'-trifluorobiphenyl-2-yl)-3-fluoromethyl-1-methylpyrazol-4-ylcarboxamide, N-(3',4',5'-trifluorobiphenyl-2-yl)-3-(chlorofluoromethyl)-1-methylpyrazol-4-ylcarboxamide, N-(3',4',5'-trifluorobiphenyl-2-yl)-3-difluoromethyl-1-methylpyrazol-4-ylcarboxamide, N-(3',4',5'-trifluorobiphenyl-2-yl)-3-difluoromethyl-5-fluoro-1-methylpyrazol-4-ylcarboxamide, N-(3',4',5'-trifluorobiphenyl-2-yl)-5-chloro-3-difluoromethyl-1-methylpyrazol-4-ylcarboxamide, N-(3',4',5'-trifluorobiphenyl-2-yl)-3-(chlorodifluoromethyl)-1-methylpyrazol-4-ylcarboxamide, N-(3',4',5'-trifluorobiphenyl-2-yl)-1-methyl-3-trifluoromethylpyrazol-4-ylcarboxamide, N-(3',4',5'-trifluorobiphenyl-2-yl)-5-fluoro-1-methyl-3-trifluoromethylpyrazol-4-ylcarboxamide, N-(3',4',5'-trifluorobiphenyl-2-yl)-5-chloro-1-methyl-3-trifluoromethylpyrazol-4-ylcarboxamide, N-(2',4',5'-trifluorobiphenyl-2-yl)-1,3-dimethylpyrazol-4-ylcarboxamide, N-(2',4',5'-trifluorobiphenyl-2-yl)-1,3-dimethyl-5-fluoropyrazol-4-ylcarboxamide, N-(2',4',5'-trifluorobiphenyl-2-yl)-5-chloro-1,3-dimethylpyrazol-4-ylcarboxamide, N-(2',4',5'-trifluorobiphenyl-2-yl)-3-fluoromethyl-1-methylpyrazol-4-ylcarboxamide, N-(2',4',5'-trifluorobiphenyl-2-yl)-3-(chlorofluoromethyl)-1-methylpyrazol-4-ylcarboxamide, N-(2',4',5'-trifluorobiphenyl-2-yl)-3-difluoromethyl-1-methylpyrazol-4-ylcarboxamide, N-(2',4',5'-trifluorobiphenyl-2-yl)-3-difluoromethyl-5-fluoro-1-methylpyrazol-4-ylcarboxamide, N-(2',4',5'-trifluorobiphenyl-2-yl)-5-chloro-3-difluoromethyl-1-methylpyrazol-4-ylcarboxamide, N-(2',4',5'-trifluorobiphenyl-2-yl)-3-(chlorodifluoromethyl)-1-methylpyrazol-4-ylcarboxamide, N-(2',4',5'-trifluorobiphenyl-2-yl)-1-methyl-3-trifluoromethylpyrazol-4-ylcarboxamide, N-(2',4',5'-trifluorobiphenyl-2-yl)-5-fluoro-1-methyl-3-trifluoromethyl pyrazol-4-ylcarboxamide, N-(2',4',5'-trifluorobiphenyl-2-yl)-5-chloro-1-methyl-3-trifluoromethylpyrazol-4-ylcarboxamide, N-(3',4'-dichloro-3-fluorobiphenyl-2-yl)-1-methyl-3-trifluoromethyl-1H-pyrazole-4-carboxamide, N-(3',4'-dichloro-3-fluorobiphenyl-2-yl)-1-methyl-3-difluoromethyl-1H-pyrazole-4-carboxamide, N-(3',4'-difluoro-3-fluorobiphenyl-2-yl)-1-methyl-3-trifluoromethyl-1H-pyrazole-4-carboxamide, N-(3',4'-difluoro-3-fluorobiphenyl-2-yl)-1-methyl-5-difluoromethyl-1H-pyrazole-4-carboxamide, N-(3'-chloro-4'-fluoro-3-fluorobiphenyl-2-yl)-1-methyl-3-difluoromethyl-1H-pyrazole-4-carboxamide, N-(3',4'-dichloro-4-fluorobiphenyl-2-yl)-1-methyl-3-trifluoromethyl-1H-pyrazole-4-carboxamide, N-(3',4'-difluoro-4-fluorobiphenyl-2-yl)-1-methyl-S-trifluoromethyl-1H-pyrazole-4-carboxamide, N-(3',4'-dichloro-4-fluorobiphenyl-2-yl)-1-methyl-3-difluoromethyl-1H-pyrazole-4-carboxamide, N-(3',4'-difluoro-4-fluorobiphenyl-2-yl)-1-methyl-3-difluoromethyl-1H-pyrazole-4-carboxamide, N-(3'-chloro-4'-fluoro-4-fluorobiphenyl-2-yl)-1-methyl-5-difluoromethyl-1H-pyrazole-4-carboxamide, N-(3',4'-dichloro-5-fluorobiphenyl-2-yl)-1-methyl-3-trifluoromethyl-1H-pyrazole-4-carboxamide, N-(3',4'-difluoro-5-fluorobiphenyl-2-yl)-1-methyl-3-trifluoromethyl-1H-pyrazole-4-carboxamide, N-(3',4'-dichloro-5-fluorobiphenyl-2-yl)-1-methyl-S-difluoromethyl-1H-pyrazole-carboxamide, N-(3',4'-difluoro-5-fluorobiphenyl-2-yl)-1-methyl-3-difluoromethyl-1H-pyrazole-4-carboxamide, N-(3',4'-dichloro-5-fluorobiphenyl-2-yl)-1,3-dimethyl-1H-pyrazole-4-carboxamide, N-(3'-chloro-4'-fluoro-5-fluorobiphenyl-2-yl)-1-methyl-3-difluoromethyl-1H-pyrazole-4-carboxamide, N-(4'-fluoro-4-fluorobiphenyl-2-yl)-1-methyl-3-trifluoromethyl-1H-pyrazole-4-carboxamide, N-(4'-fluoro-5-fluorobiphenyl-2-yl)-1-methyl-3-trifluoromethyl-1H-pyrazole-4-carboxamide, N-(4'-chloro-5-fluorobiphenyl-2-yl)-1-methyl-3-trifluoromethyl-1H-pyrazole-4-carboxamide, N-(4'-methyl-5-fluorobiphenyl-2-yl)-1-methyl-3-trifluoromethyl-1H-pyrazole-4-carboxamide, N-(4'-fluoro-5-fluorobiphenyl-2-yl)-1,3-dimethyl-1H-pyrazole-4-carboxamide, N-(4'-chloro-5-fluorobiphenyl-2-yl)-1,3-dimethyl-1H-pyrazole-4-carboxamide, N-(4'-methyl-5-fluorobiphenyl-2-yl)-1,3-dimethyl-1H-pyrazole-4-carboxamide, N-(4'-fluoro-6-fluorobiphenyl-2-yl)-1-methyl-3-trifluoromethyl-1H-pyrazole-4-carboxamide, N-(4'-chloro-6-fluorobiphenyl-2-yl)-1-methyl-3-trifluoromethyl-1H-pyrazole-4-carboxamide, N-[2-(1,1,2,3,3,3-hexafluoropropoxy)-phenyl]-3-difluoromethyl-1-methyl-1H-pyrazole-4-carboxamide, N-[4'-(trifluoromethylthio)-biphenyl-2-yl]-3-difluoromethyl-1-methyl-1H-pyrazole-4-carboxamide and N-[4'-(trifluoromethylthio)-biphenyl-2-yl]-1-methyl-3-trifluoromethyl-1-methyl-1H-pyrazole-4-carboxamide, 3-difluoromethyl-N-(7-fluoro-1,1,3-trimethyl-4-indanyl)-1-methyl-4-pyrazolecarboxamide (fluindapyr), 4-difluoromethyl-N-(7-fluoro-1,1,3-trimethyl-4-indanyl)-2-methyl-5-thiazolecarboxamide, 3-difluoromethyl-1-methyl-N-(1,1,3,7-tetra methyl-4-indanyl)-pyrazolecarboxamide, 4-difluoromethyl-2-methyl-N-(1,1,3,7-tetramethyl-4-indanyl)-5-thiazolecarboxamide, 3-difluoromethyl-1-methyl-N-(7-methoxy-1,1,3-trimethyl-4-indanyl)-4-pyrazolecarboxamide, 4-difluoromethyl-2-methyl-N-(7-methoxy-1,1,3-trimethyl-4-indanyl)-5-thiazolecarboxamide, 3-difluoromethyl-1-methyl-N-(7-methylthio-1,1,3-trimethyl-4-indanyl)-4-pyrazolecarboxamide, 4-difluoromethyl-2-methyl-N-(7-methylthio-1,1,3-trimethyl-4-indanyl)-5-thiazolecarboxamide, 3-difluoromethyl-1-methyl-N-(7-trifluoromethoxy-1,1,3-trimethyl-4-indanyl)-4-pyrazolecarboxamide, 4-difluoromethyl-2-methyl-N-(7-trifluoromethoxy-1,1,3-trimethyl-4-indanyl)-5-thiazolecarboxamide, 3-difluoromethyl-N-(7-fluoro-1,1,3-trimethyl-4-indanyl)-4-furazancarboxamide, 4-difluoromethyl-N-(7-fluoro-1,1,3-trimethyl-4-indanyl)-2-methylthio-5-pyrimidinecarboxamide, 3-difluoromethyl-N-(7-chloro-1,1,3-trimethyl-4-indanyl)-1-methyl-4-pyrazolecarboxamide, 3-difluoromethyl-N-(7-chloro-1,1-diethyl-3-methyl-4-indanyl)-1-methyl-4-pyrazolecarboxamide, or 4-difluoromethyl-N-(7-fluoro-1,1,3-trimethyl-4-indanyl)-5-thiadiazolecarboxamide; B4) heterocyclic compounds, including fluazinam, pyrifenox, bupirimate, cyprodinil, fenarimol, ferimzone, mepanipyrim, nuarimol, pyrimethanil, triforine, fenpiclonil, fludioxonil, aldimorph, dodemorph, fenpropimorph, tridemorph, fenpropidin, iprodione, procymidone, vinclozolin, famoxadone, fenamidone, octhilinone, probenazole, 5-chloro-7-(4-methyl-piperidin-1-yl)-6-(2,4,6-trifluorophenyl)-[1,2,4]triazolo[1,5-a]pyrimidine, anilazine, diclomezine, pyroquilon, proquinazid, tricyclazole, 2-butoxy-6-iodo-3-propylchromen-4-one, acibenzolar-S-methyl, captafol, captan, dazomet, folpet, fenoxanil, quinoxyfen, N,N-dimethyl-3-(3-bromo-6-fluoro-2-methylindole-1-sulfonyl)-[1,2,4]triazole-1-sulfonamide, 5-ethyl-6-octyl-[1,2,4]triazolo[1,5-a]pyrimidin-2,7-diamine, 2,3,5,6-tetrachloro-4-methanesulfonyl-pyridine, 3,4,5-trichloro-pyridine-2,6-di-carbonitrile, N-(1-(5-bromo-3-chloro-pyridin-2-yl)-ethyl)-2,4-dichloro-nicotinamide, N-((5-bromo-3-chloro pyridin-2-yl)-methyl)-2,4-dichloro-nicotinamide, diflumetorim, nitrapyrin, dodemorphacetate, fluoroimid, blasticidin-S, chinomethionat, debacarb, difenzoquat, difenzoquat-methylsulphat, oxolinic acid and piperalin; B5) carbamates, including mancozeb, maneb, metam, methasulphocarb, metiram, ferbam, propineb, thiram, zineb, ziram, diethofencarb, iprovalicarb, benthiavalicarb, propamocarb, propamocarb hydrochlorid, 4-fluorophenyl N-(1-(1-(4-cyanophenyl)-ethanesulfonyl)but-2-yl)carbamate, methyl 3-(4-chloro-phenyl)-3-(2-isopropoxycarbonylamino-3-methyl-butyrylamino)propanoate; or B6) other fungicides, including guanidine, dodine, dodine free base, iminoctadine, guazatine, antibiotics: kasugamycin, oxytetracyclin and its salts, streptomycin, polyoxin, validamycin A, nitrophenyl derivatives: binapacryl, dinocap, dinobuton, sulfur-containing heterocyclyl compounds: dithianon, isoprothiolane, organometallic compounds: fentin salts, organophosphorus compounds: edifenphos, iprobenfos, fosetyl, fosetyl-aluminum, phosphorous acid and its salts, pyrazophos, tolclofos-methyl, organochlorine compounds: dichlofluanid, flusulfamide, hexachloro-benzene, phthalide, pencycuron, quintozene, thiophanate, thiophanate-methyl, tolylfluanid, others: cyflufenamid, cymoxanil, dimethirimol, ethirimol, furalaxyl, metrafenone and spiroxamine, guazatine-acetate, iminoctadine-triacetate, iminoctadine-tris(albesilate), kasugamycin hydrochloride hydrate, dichlorophen, pentachlorophenol and its salts, N-(4-chloro-2-nitro-phenyl)-N-ethyl-4-methyl-benzenesulfonamide, dicloran, nitrothal-isopropyl, tecnazen, biphenyl, bronopol, diphenylamine, mildiomycin, oxincopper, prohexadione calcium, N-(cyclopropylmethoxyimino-(6-difluoromethoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluormethyl-4-(3-trimethylsilanyl-propoxy)-phenyl)-N-ethyl-N-methylformamidine and N'-(5-difluormethyl-2-methyl-4-(3-trimethylsilanyl-propoxy)-phenyl)-N-ethyl-N-methyl formamidine.

Of note are mixtures of the Bacillus thuringiensis RTI545 strain with other biocontrol strains including Bacillus subtilis strains such as CH201 or QST713 or MBI600 or RTI477, Bacillus licheniformis strains such as CH200 or RTI184, Bacillus velezensis strains such as RTI301, Bacillus subtilis var. amyloliquefaciens FZB24, or Bacillus amyloliquefaciens D747, or combinations thereof for fungal disease control.

In the compositions and methods of the present disclosure, the composition can include a chemical fungicide.

Preferred are mixtures of the Bacillus thuringiensis RTI545 strain with chemical fungal control agents comprising thiabendazole, fluxapyroxad, penflufen, sedaxane, bitertanol, cyproconazole, difenoconazole, fluquinconazole, flutriafol, ipconazole, myclobutanil, prothioconazole, triadimefon, triadimenol, tebuconazole, triticonazole, prochloraz, imazalil, benomyl, carbendazim, hymexazole, azoxystrobin, fluoxastrobin, pyraclostrobin, trifloxystrobin, carboxin, flutolanil, metalaxyl, mefenoxam, penthiopyrad, fluopyram, silthiofam, fluazinam, pyrimethanil, fludioxonil, iprodione, tricyclazole, captan, dazomet, mancozeb, metam, thiram, guazatine, tolclofos-methyl, pencycuron, thiophanate-methyl, fenpicoxamide, mefentrifluconazole, fluindapyr, or any mixtures thereof.

More preferred are mixtures of the Bacillus thuringiensis RTI545 strain with fludioxonil, prothioconazole, mefenoxam, metalaxyl, tebuconazole, difenoconazole, thiram, carboxin, carbendazim, triticonazole, pencycuron, imazalil, pyraclostrobin, sedaxane, trifloxystrobin, fluquinconazole, fluoxastrobin, azoxystrobin, flutriafol, fluxapyroxad, penthiopyrad, fenpicoxamide, mefentrifluconazole, fluindapyr or mixtures thereof.

Herbicides: C1) acetyl-CoA carboxylase inhibitors (ACC), for example cyclohexenone oxime ethers, such as alloxydim, clethodim, cloproxydim, cycloxydim, sethoxydim, tralkoxydim, butroxydim, clefoxydim or tepraloxydim; phenoxyphenoxypropionic esters, such as clodinafop-propargyl, cyhalofop-butyl, diclofop-methyl, fenoxaprop-ethyl, fenoxaprop-P-ethyl, fenthiapropethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl or quizalofop-tefuryl; or arylaminopropionic acids, such as flamprop-methyl or flamprop-isopropyl; C2 acetolactate synthase inhibitors (ALS), for example imidazolinones, such as imazapyr, imazaquin, imazamethabenz-methyl (imazame), imazamox, imazapic or imazethapyr; pyrimidyl ethers, such as pyrithiobac-acid, pyrithiobac-sodium, bispyribac-sodium. KIH-6127 or pyribenzoxym; sulfonamides, such as florasulam, flumetsulam or metosulam; or sulfonylureas, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, halosulfuron-methyl, imazosulfuron, metsulfuron-methyl, nicosulfuron, primisulfuron-methyl, prosulfuron, pyrazosulfuron-ethyl, rimsulfuron, sulfometuron-methyl, thifensulfuron-methyl, triasulfuron, tribenuron-methyl, triflusulfuron-methyl, tritosulfuron, sulfosulfuron, foramsulfuron or iodosulfuron; C3) amides, for example allidochlor (CDAA), benzoylprop-ethyl, bromobutide, chiorthiamid, diphenamid, etobenzanidibenzchlomet), fluthiamide, fosamin or monalide; C4) auxin herbicides, for example pyridinecarboxylic acids, such as clopyralid or picloram; or 2,4-D or benazolin; C5) auxin transport inhibitors, for example naptalame or diflufenzopyr; C6) carotenoid biosynthesis inhibitors, for example benzofenap, clomazone (dimethazone), diflufenican, fluorochloridone, fluridone, pyrazolynate, pyrazoxyfen, isoxaflutole, isoxachlortole, mesotrione, sulcotrione (chlormesulone), ketospiradox, flurtamone, norflurazon or amitrol; C7) enolpyruvylshikimate-3-phosphate synthase inhibitors (EPSPS), for example glyphosate or sulfosate; C8) glutamine synthetase inhibitors, for example bilanafos (bialaphos) or glufosinate-ammonium; C9) lipid biosynthesis inhibitors, for example anilides, such as anilofos or mefenacet; chloroacetanilides, such as dimethenamid, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchlor, thenylchlor or xylachlor; thioureas, such as butylate, cycloate, di-allate, dimepiperate, EPTC. esprocarb, molinate, pebulate, prosulfocarb, thiobencarb (benthiocarb), tri-allate or vemolate; or benfuresate or perfluidone; C10) mitosis inhibitors, for example carbamates, such as asulam, carbetamid, chlorpropham, orbencarb, pronamid (propyzamid), propham or tiocarbazil; dinitroanilines, such as benefin, butralin, dinitramin, ethalfluralin, fluchloralin, oryzalin, pendimethalin, prodiamine or trifluralin; pyridines, such as dithiopyr or thiazopyr; or butamifos, chlorthal-dimethyl (DCPA) or maleic hydrazide; C11) protoporphyrinogen IX oxidase inhibitors, for example diphenyl ethers, such as acifluorfen, acifluorfen-sodium, aclonifen, bifenox, chlomitrofen (CNP), ethoxyfen, fluorodifen, fluoroglycofen-ethyl, fomesafen, furyloxyfen, lactofen, nitrofen, nitrofluorfen or oxyfluorfen; oxadiazoles, such as oxadiargyl or oxadiazon; cyclic imides, such as azafenidin, butafenacil, carfentrazone-ethyl, cinidon-ethyl, flumiclorac-pentyl, flumioxazin, flumipropyn, flupropacil, fluthiacet-methyl, sulfentrazone or thidiazimin; or pyrazoles, such as ET-751.JV 485 or nipyraclofen; C12) photosynthesis inhibitors, for example propanil, pyridate or pyridafol; benzothiadiazinones, such as bentazone; dinitrophenols, for example bromofenoxim, dinoseb, dinoseb-acetate, dinoterb or DNOC; dipyridylenes, such as cyperquat-chloride, difenzoquat-methylsulfate, diquat or paraquat-dichloride; ureas, such as chlorbromuron, chlorotoluron, difenoxuron, dimefuron, diuron, ethidimuron, fenuron, fluometuron, isoproturon, isouron, linuron, methabenzthiazuron, methazole, metobenzuron, metoxuron, monolinuron, neburon, siduron or tebuthiuron; phenols, such as bromoxynil or ioxynil; chloridazon; triazines, such as ametryn, atrazine, cyanazine, desmein, dimethamethryn, hexazinone, prometon, prometryn, propazine, simazine, simetryn, terbumeton, terbutryn, terbutylazine or trietazine; triazinones, such as metamitron or metribuzin; uracils, such as bromacil, lenacil or terbacil; or biscarbamates, such as desmedipham or phenmedipham; C13) synergists, for example oxiranes, such as tridiphane; C14) CIS cell wall synthesis inhibitors, for example isoxaben or dichlobenil; C15) various other herbicides, for example dichloropropionic acids, such as dalapon; dihydrobenzofurans, such as ethofumesate; phenylacetic acids, such as chlorfenac (fenac); or aziprotryn, barban, bensulide, benzthiazuron, benzofluor, buminafos, buthidazole, buturon, cafenstrole, chlorbufam, chlorfenprop-methyl, chloroxuron, cinmethylin, cumyluron, cycluron, cyprazine, cyprazole, dibenzyluron, dipropetryn, dymron, eglinazin-ethyl, endothall, ethiozin, flucabazone, fluorbentranil, flupoxam, isocarbamid, isopropalin, karbutilate, mefluidide, monuron, napropamide, napropamide-M, napropanilide, nitralin, oxaciclomefone, phenisopham, piperophos, procyazine, profluralin, pyributicarb, secbumeton, sulfallate (CDEC), terbucarb, triaziflam, triazofenamid or trimeturon; or their environmentally compatible salts.

Nematicides or bionematicides: benomyl, cloethocarb, aldoxycarb, tirpate, diamidafos, fenamiphos, cadusafos, dichlofenthion, ethoprophos, fensulfothion, fosthiazate, heterophos, isamidofof, isazofos, phosphocarb, thionazin, imicyafos, mecarphon, acetoprole, benclothiaz, oxamyl, chloropicrin, dazomet, fluensulfone, 1,3-dichloropropene (telone), dimethyl disulfide, metam sodium, metam potassium, metam salt (all MITC generators), methyl bromide, biological soil amendments (e.g., mustard seeds, mustard seed extracts), steam fumigation of soil, allyl isothiocyanate (AITC), dimethyl sulfate, furfural (aldehyde), fluazaindolizine (DPX-Q8U80), fluopyram, or tioxazafen.

Preferred are mixtures of the Bacillus thuringiensis RTI545 strain with chemical nematode control agents comprising benomyl, fenamiphos, cadusafos, ethoprophos, fosthiazate, chloropicrin, dazomet, fluensulfone, oxamyl, 1,3-dichloropropene (telone), metam sodium, metam potassium, metam salt (all MITC generators), methyl bromide, allyl isothiocyanate (AITC), fluazaindolizine (DPX-Q8U80), tioxazafen, fluopyram, or any mixtures thereof.

More preferred are mixtures of the Bacillus thuringiensis RTI545 strain with cadusafos, ethoprophos, fosthiazate, fluensulfone, oxamyl, fluazaindolizine (DPX-Q8U80), tioxazafen, or any mixtures thereof. In the compositions and methods of the present disclosure, the composition can include the nematicide cadusafos.

Suitable plant growth regulators of the present invention include the following: Plant Growth Regulators: D1) Anti-auxins, such as clofibric acid, 2,3,5-tri-iodobenzoic acid; D2) Auxins such as 4-CPA, 2,4-D, 2,4-DB, 2,4-DEP, dichlorprop, fenoprop, IAA, IBA, naphthaleneacetamide, α-naphthaleneacetic acids, 1-naphthol, naphthoxyacetic acids, potassium naphthenate, sodium naphthenate, 2,4,5-T; D3) cytokinins, such as 2iP, benzyladenine, 4-hydroxyphenethyl alcohol, kinetin, zeatin; D4) defoliants, such as calcium cyanamide, dimethipin, endothal, ethephon, merphos, metoxuron, pentachlorophenol, thidiazuron, tribufos; D5) ethylene inhibitors, such as aviglycine, 1-methylcyclopropene; D6) ethylene releasers, such as ACC, etacelasil, ethephon, glyoxime; D7) gametocides, such as fenridazon, maleic hydrazide; D8) gibberellins, such as gibberellins, gibberellic acid; D9) growth inhibitors, such as abscisic acid, ancymidol, butralin, carbaryl, chlorphonium, chlorpropham, dikegulac, flumetralin, fluoridamid, fosamine, glyphosine, isopyrimol, jasmonic acid, maleic hydrazide, mepiquat, piproctanyl, prohydrojasmon, propham, tiaojiean, 2,3,5-tri-iodobenzoic acid; D10) morphactins, such as chlorfluren, chlorflurenol, dichlorflurenol, flurenol; D11) growth retardants, such as chlormequat, daminozide, flurprimidol, mefluidide, paclobutrazol, tetcyclacis, uniconazole; D12) growth stimulators, such as brassinolide, brassinolide-ethyl, DCPTA, forchlorfenuron, hymexazol, prosuler, triacontanol; D13) unclassified plant growth regulators, such as bachmedesh, benzofluor, buminafos, carvone, choline chloride, ciobutide, clofencet, cyanamide, cyclanilide, cycloheximide, cyprosulfamide, epocholeone, ethychlozate, ethylene, fuphenthiourea, furalane, heptopargil, holosulf, inabenfide, karetazan, lead arsenate, methasulfocarb, prohexadione, pydanon, sintofen, triapenthenol, trinexapac.

Chemical formulations of the present invention can be in any appropriate conventional form, for example an emulsion concentrate (EC), a suspension concentrate (SC), a suspo-emulsion (SE), a capsule suspension (CS), a water dispersible granule (WG), an emulsifiable granule (EG), a water in oil emulsion (EO), an oil in water emulsion (EW), a micro-emulsion (ME), an oil dispersion (OD), an oil miscible flowable (OF), an oil miscible liquid (OL), a soluble concentrate (SL), an expandable foam (EF) suspension, an ultra-low volume suspension (SU), an ultra-low volume liquid (UL), a dispersible concentrate (DC), a wettable powder (WP), granules (G) of various sizes that, in embodiments, may be deposited at the time of planting, or any technically feasible formulation in combination with agriculturally acceptable adjuvants.

In embodiments, the composition may comprise: 0.5-99 weight % of a biologically pure culture of Bacillus thuringiensis RTI545 deposited as ATCC No. PTA-122161, or a mutant thereof having all the identifying characteristics thereof, of at not less than about $1\times10^{11}$ CFU/g, and an agriculturally acceptable adjuvant. In at least one embodiment, the active ingredient comprising the Bacillus species is present in total concentrations ranging between 0.5% to about 95 weight % of the agricultural composition, such as wherein the Bacillus species is present in an amount independently selected from a lower limit of 1, 2, 3, 4 or 5, 7, 8, or 10 weight % to an upper limit of 10, 15, 20, 25, 40, 50, 60, 70, 80 or 90 weight % of the total composition. In another embodiment, agriculturally acceptable adjuvants constitute about 1% to about 99.5%, such as from a lower limit of 1, 2, 3, 4 or 5 weight % to an upper limit of 10, 15, 20, 25, 40, 50, 60, 70, 80, 90, or 95 weight % of the total composition.

In embodiments, the adjuvant may be selected from the group consisting of liquid carriers, solid carriers, surface acting agents (surfactants), viscosity modifiers, thickeners, rheology additives, structuring agents, preservatives, biocides or biostatic agents, antifreezes, crystallization inhibitors, suspending agents, dyes, anti-oxidants, foaming agents, light absorbers, mixing auxiliaries, antifoams, complexing agents, neutralizing or pH-modifying substances and buffers, corrosion inhibitors, fragrances, wetting agents, take-up enhancers, micronutrients, plasticizers, glidants, lubricants, and dispersants.

Carriers can be liquid or solid. Adjuvants that may be used in such formulations include surface active agents, viscosity modifiers such as thickeners, preservatives, biocides or biostatic agents, antifreezes, crystallization inhibitors, suspending agents, dyes, anti-oxidants, foaming agents, light absorbers, mixing auxiliaries, antifoams, complexing agents, neutralizing or pH-modifying substances and buffers, corrosion inhibitors, fragrances, wetting agents, take-up enhancers, micronutrients, plasticizers, glidants, lubricants, dispersants, and also liquid and solid fertilizers.

In embodiments, the compositions of this invention may be formulated as a suspension concentrate (SC), wettable powder (WP) or wettable granule (WG). Other formulations types include water dispersible powders for slurry treatment (WS), oil dispersions (OD), granules for broadcast applications (GR), capsule suspensions (CS), emulsifiable concentrates (EC), emulsions in water (EW), soluble concentrates (SL), mixed formulations of a CS and an SC (ZC), mixed formulations of an SC and an EW as suspo-emulsions (SE), an expandable foam (EF) suspension, or mixed formulations of a CS and an EW (ZW). In some embodiments the compositions may be formulated as dusts, or powders, or granules that can be applied to the plant, plant part, seed, or soil as a dry formulation (e.g. a dry seed coating on peanuts or a dust, powder or granules of various sizes for incorporation into soil).

Liquid carriers include solvents and co-solvents including water, petroleum ether, vegetable oils, acid anhydrides, amyl acetate, butylene carbonate, cyclohexane, cyclohexanol, diacetone alcohol, 1,2-dichloropropane, diethanolamine, diethylene glycol, diethylene glycol abietate, diethylene glycol butyl ether, diethylene glycol ethyl ether, diethylene glycol methyl ether, 1,4-dioxane, dipropylene glycol, dipropylene glycol methyl ether, dipropylene glycol dibenzoate, diproxitol, alkylpyrrolidone, 2-ethylhexanol, ethylene carbonate, 1,1,1-trichloroethane, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isobornyl acetate, isooctane, isophorone, isopropyl myristate, lactic acid, laurylamine, mesityl oxide, methoxypropanol, methyl laurate, methyl octanoate, methyl oleate, methylene chloride, n-hexane, n-octylamine, octadecanoic acid, octylamine acetate, oleic acid, oleylamine, polyethylene glycol (PEG), propionic acid, propyl lactate, propylene carbonate, propylene glycol, propylene glycol methyl ether, triethyl phosphate, triethylene glycol, xylenesulfonic acid, paraffin, mineral oil, trichloroethylene, perchloroethylene, alcohols of higher molecular weight, such as amyl alcohol, tetrahydrofurfuryl alcohol, hexanol, octanol, liquid amides such as N,N-dimethyloctanamide, N,N-dimethyldecanamide, N-methyl-N-(2-propylheptyl)-acetamide, N-methyl-N-(2-propylheptyl)-formamide, N-methyl-2-pyrrolidone and the like. Preferably, liquid carriers are such that the biological active agents remain essentially unchanged in the composition until after it is applied to the locus of control. Water is generally the carrier of choice for diluting the concentrated formulations.

Suitable solid carriers include, for example, carbohydrates including mono or di carbohydrates such as sucrose, oligo or poly-saccharides such as maltodextrin or pectin, talc, titanium dioxide, pyrophyllite clay, attapulgite clay, kieselguhr, silica (silicon dioxide), limestone, bentonite, calcium montmorillonite water soluble salts such as sodium, potassium, magnesium, calcium or ammonium salts of acetate, carbonate, chloride, citrate, phosphate, or sulfate such as calcium carbonate, cottonseed husks, wheat flour, soybean flour, pumice, wood flour, ground walnut shells, lignin and similar substances, yeast extracts, fish meal, or mixtures thereof. Notable solid carriers include maltodextrin, silica, calcium carbonate, or any mixtures thereof.

Surface active agents including surfactants, dispersants and emulsifiers, viscosity enhancing agents, solvents and other adjuvants independently may constitute between about 0.1% to about 25% of the final formulation by weight.

The compositions may contain a surface-active substance (surfactants, dispersants and emulsifiers) from a very large variety of substances known in the art that are also commercially available. Surface-active substances (described herein generally as surfactants) may be anionic, cationic, non-ionic or polymeric and they can be used as surfactants, dispersants, emulsifiers, wetting agents or suspending agents or for other purposes.

Surfactants belong to different classes such as cationic surfactants, anionic surfactants, non-ionic surfactants, ionic surfactants, and amphoteric surfactants. According to the invention, the surfactant can be any surfactant or combination of two or more surfactants useful to disperse the biological active ingredients in the formulation or tank mix for application. The amounts of the surfactant in the compositions of this invention may range from about 1 to about 15%, or about 1 to about 10%, preferably about 3 to about 8%, and more preferably about 5 to about 7% w/w.

Examples of some preferred surfactants include cationic, non-ionic, anionic and/or amphoteric surfactants.

Non-ionic surfactants suitable for this invention include ethoxylated linear alcohols, ethoxylated alkyl phenol, alkyl EO/PO copolymer, polyalkylene glycol monobutyl ether ethoxylated fatty acids/oils, sorbitan laurate, polysorbate, sorbitan oleate, ethoxylated fatty acid alcohols, or alkyl phenols, alkanolamides or alkyloamides (such as diethanolamide, lauric acid monoisopropanolamide, and ethoxylated myristamide), xyethylene fatty acid esters, polyoxyethylene fatty alcohol ethers (such as alkylaryl polyglycol ethers), alkylphenol/alkylene oxide addition products, such as nonylphenol ethoxylate; alcohol/alkylene oxide addition products, such as tridecylalcohol ethoxylate.

Anionic surfactants include alkyl-, alkylaryl- and arylsulfonates or salts thereof (such as sodium, potassium or calcium salts of lauryl sarcosinate, alkylbenzenesulfonate, dodecylbenzenesulfonate, alkylnaphthalenesulfonates such as dibutylnaphthalenesulfonate, or $C_{14-16}$ olefin sulfonates), alkyl-, alkylaryl- and arylsulfates or salts thereof (such as sodium, potassium or calcium salts of tridedeth sulfate, lauryl sulfate, decyl sulfate, and diethanolammonium lauryl sulfate) protein hydrolysates, derivatives of polycarboxylic acid (such as ammonium lauryl ether carboxylate), olefin sulfonates (such as sodium alpha olefin sulfonate), sarcosinates (such as ammonium cyclohexyl palmitoyl taurinate), succinates (such as disodium N-octadecyl sulfosuccinamate), phosphorus derivatives (such as phosphoric acid esters and their equivalent salts).

Cationic surfactants include alkylbenzyltrimethylammonium chloride, ammonium lauryl sulfate and lauramine oxide.

In some embodiments, surfactants may be used as foaming agents allowing the formulation to be foamable for applying to the seed or in-furrow at the time of planting. The foamable composition can be optionally diluted with water and mixed with a pressurized gas such as air in a foaming chamber comprising a foaming medium such as a plurality of glass beads.

Suitable foaming agents may be nonionic surfactants including alkanolamides or alkyloamides (such as cocamide diethanolamide, lauric acid monoisopropanolamide, and ethoxylated myristamide), xyethylene fatty acid esters, polyoxyethylene fatty alcohol ethers (such as alkylaryl polyglycol ethers) and fluorocarbons (such as ethoxylated polyfluorinated alcohol); anionic surfactants including alkyl-, alkylaryl- and arylsulfonates (such as sodium lauryl sarcosinate and such as sodium alkylbenzenesulfonate), alkyl-, alkylaryl- and arylsulfates, protein hydrolysates, derivatives of polycarboxylic acid (such as ammonium lauryl ether carboxylate), olefin sulfonates (such as sodium alpha olefin sulfonate), sarcosinates (such as ammonium cyclohexyl palinitoyl taurinate), succinates (such as disodium N-octadecyl sulfosuccinamate), phosphorus derivatives (such as phosphoric acid esters and their equivalent salts); cationic surfactants including alkylbenzyltrimethylammonium chloride; and amphoteric surfactants including betaine. Particularly preferred foaming agents include sodium dodecylbenzene sulfonate (ex. Bio-Soft® D-40), sodium $C_{14-16}$ olefin sulfonate (ex. Bioterge® AS-40), lauramine oxide (ex. Ammonyx® DO, Ammonyx® LO), ammonium lauryl sulfate (ex. Steol®), sodium (Cedepal® TD-407) and alkyl sulfates (ex Polystep® B-25). The total concentration of foaming agents in the formulation will be dependent on the foaming agents used and may comprise between about 0.1% and about 50% of the concentrated foamable formulation, preferably between about 0.3% and about 30% more preferably between about 5% and 25% and even more preferably between about 17% and about 23%.

Notable embodiments include those wherein the volume of the foam generated by the formulation is reduced by 25% (or less) after about 45 minutes or greater. Other surface active substances include soaps, such as sodium stearate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters.

Also suitable are silicone surfactants, especially polyalkyl-oxide-modified heptamethyltriloxanes which are commercially available e.g. as Silwet L-77®, and also perfluorinated surfactants.

Of these, some even more specific types of preferred surfactants include non-ionic linear or branched alcohol ethoxylate surfactants, anionic phosphoric acid ester surfactants (sometimes referred to as "phosphate ester" surfactants), and cationic ethoxylated tallow amine surfactants.

Notable surfactants (dispersants) comprise at least one alkyl alkylpolyglycoside, preferably comprising $C_8$-$C_{14}$ alkyl groups. The Agnique® products of BASF Corporation (Cognis) are representative. In one embodiment, the alkyl d-glycopyranoside surfactant includes a mixture of $C_8$-$C_{10}$ alkyl d-glucopyranosides, such as Agnique® PG8105-G. In another embodiment, the alkyl d-glucopyranoside surfactant includes a mixture of $C_9$-$C_{11}$ alkyl d-glucopyranosides. A preferred product is Agnique® PG9116 which is a mixture of $C_9$-$C_{11}$ alkyl d-glucopyranosides, having a degree of polymerization of about 1.6 and a hydrophilic-lipophilic balance (HLB) of about 13.1.

Phosphate ester surfactants (dispersants) may comprise phosphate esters of alcohols, ethoxylated alcohols or ethoxylated phenol. They can be in the free acid form or neutralized as the sodium, potassium or ammonium salts. The Dextrol® products of Ashland Corporation are representative, such as Dextrol® OC-180. The phosphate ester is preferably selected from a nonyl phenol phosphate ester and a tridecyl alcohol ethoxylated phosphate potassium salt.

In another aspect, the composition may contain a thickener, viscosity modifier, rheology additive or structuring agent that stabilize formulations such as suspension concentrates or oil dispersions against settling or sedimentation. Suitable thickeners are rice, starch, gum arabic, gum tragacanth, guar flour, British gum, starch ethers and starch esters, gum resins, galactomannans, magnesium aluminum silicate, xanthan gum, carrageenan, cellulose derivatives, methyl cellulose, carboxymethylcellulose, alginates and combinations thereof. Other known commercial products may include Lattice NTC 50, Lattice NTC 60, methocel, clay, and veegum silica.

In another embodiment, the compositions of this invention may contain an antifreeze agent such as glycerine, ethylene glycol, propylene glycol, urea, calcium chloride, sodium nitrate, magnesium chloride and ammonium sulfate.

Suitable preservatives include but are not limited to $C_{12}$ to $C_{15}$ alkyl benzoates, alkyl p-hydroxybenzoates, aloe vera extract, ascorbic acid, benzalkonium chloride, benzoic acid, benzoic acid esters of $C_9$ to $C_{15}$ alcohols, butylated hydroxytoluene, butylated hydroxyanisole, tert-butylhydroquinone, castor oil, cetyl alcohols, chlorocresol, citric acid, cocoa butter, coconut oil, diazolidinyl urea, diisopropyl adipate, dimethyl polysiloxane, DMDM hydantoin, ethanol, ethylenediaminetetraacetic acid, fatty acids, fatty alcohols, hexadecyl alcohol, hydroxybenzoate esters, iodopropynyl butylcarbamate, isononyl iso-nonanoate, jojoba oil, lanolin oil, mineral oil, oleic acid, olive oil, parabens, polyethers, polyoxypropylene butyl ether, polyoxypropylene cetyl ether, potassium sorbate, propyl gallate, silicone oils, sodium propionate, sodium benzoate, sodium bisulfite, sorbic acid, stearic fatty acid, sulfur dioxide, vitamin E, vitamin E acetate and derivatives, esters, salts and mixtures thereof. Preferred preservatives include sodium o-phenylphenate, 5-chloro-2-methyl-4-isothiazolin-3-one, 2-methyl-4-isothiazolin-3-one, and 1,2-benisothiazolin-3-one.

Antifoam agents such as Xiameter AFE-100, Dow Corning AFs, Dow Corning 1520, 1530, or 1540 may also be used in the presently claimed formulations.

In embodiments, the composition may be a liquid suspension concentrate comprising water and at least one surface active agent, and one or more additional adjuvants. In embodiments, the one or more adjuvants may be selected from thickeners, viscosity modifiers, structuring agents or rheology additives, solvents, preservatives, antifreeze agents, and antifoam agents. Normally, the suspension concentrate is further diluted with water before delivery of the composition. In embodiments, the liquid composition may be a suspension concentrate comprising from 0.5 to 20 weight % of a biologically pure culture of Bacillus thuringiensis RTI545, or a mutant thereof having all the identifying characteristics thereof; 1 to 5 weight % of one or more surface active agent; and at least one thickener, solvent, preservative, antifreeze agent, or antifoam agent each independently comprising up to about 1 weight % of the composition.

In other embodiments, the composition may be a liquid oil dispersion comprising the solid active ingredients dispersed in oil such as a vegetable oil and at least one surface active agent, and one or more additional adjuvants. In embodiments, the one or more adjuvants may be selected from thickeners, viscosity modifiers, structuring agents or rheology additives, solvents, preservatives, antifreeze agents, antifoam agents and the like. Normally, the oil dispersion is further diluted with water before delivery of the composition. In embodiments, the liquid composition may be a an oil dispersion comprising from 0.5 to 20 weight % of a biologically pure culture of Bacillus thuringiensis RTI545, or a mutant thereof having all the identifying characteristics thereof; 1 to 10 weight % of one or more surface active agent; and at least one thickener, viscosity modifier, structuring agent, rheology additive, solvent, preservative, antifreeze agent, or antifoam agent each independently comprising up to about 5 weight % of the composition.

In embodiments, the composition can be in the form of a dust, powder, granule, a dry wettable powder, a spreadable granule, or a dry wettable granule and the biologically pure culture of Bacillus thuringiensis RTI545, or a mutant thereof having all the identifying characteristics thereof can be present in an amount of from about $1.0\times10^{8}$ CFU/g to about $5\times10^{13}$ CFU/g. In embodiments, the composition may comprise a solid carrier selected from the group consisting of mono- or di-saccharides, oligo- or poly-saccharides, talc, titanium dioxide, pyrophyllite clay, attapulgite clay, kieselguhr, silica, limestone, bentonite, calcium montmorillonite, sodium, potassium, magnesium, calcium or ammonium salts of acetate, carbonate, chloride, citrate, phosphate, or sulfate, cottonseed husks, wheat flour, soybean flour, pumice, wood flour, ground nut (such as peanut or walnut) shells, lignin, yeast extracts, fish meal, or mixtures thereof.

In an embodiment, the composition comprises: 5-40% of a biologically pure culture of not less than about $1\times10^{11}$ CFU/g; and maltodextrin, silica, calcium carbonate, or any mixtures thereof. In embodiments, the composition comprises 5-15% of maltodextrin.

In embodiments, the composition may comprise by weight %: 5-40% of a biologically pure culture of not less than about $1\times10^{11}$ CFU/g Bacillus thuringiensis RTI545, or a mutant thereof having all the identifying characteristics thereof; 5-15% maltodextrin; 35-45% calcium carbonate; and 5-15% silica. In embodiments, the composition may be a wettable powder formulation.

In an embodiment, the composition may be a wettable powder formulation comprising by weight %: about 40% of a biologically pure culture of not less than about $1\times10^{11}$ CFU/g Bacillus thuringiensis RTI545, or a mutant thereof having all the identifying characteristics thereof; 10% maltodextrin; 40% calcium carbonate; and 10% silica.

In embodiments, the composition is useful in either plant seed treatment or in-furrow applications for conferring protection against or controlling plant fungal pathogenic infection. For seed treatment, a solution or suspension of the composition can be applied to seed using standard seed treatment procedures. The composition may be applied to untreated seeds or seeds that have been treated with at least one additional crop protection agent as described herein. Alternatively, the composition may also be mixed with an additional crop protection agent for seed treatment or in-furrow applications. In some embodiments, the composition may be applied to the foliage of the plant to be protected, optionally mixed with an additional crop protection agent.

In some embodiments of compositions and methods, the composition further includes one or a combination of additional agricultural agent(s) such as an insecticide, fungicide, nematicide, bacteriocide, herbicide, plant extract, plant growth regulator, or fertilizer as described herein present in an amount suitable to benefit plant growth and/or to confer protection of the plant against a plant pest. The additional agricultural agent may be a microbial agent, a biological agent, or a chemical agent.

In some embodiments of compositions and methods, the composition can be formulated for compatibility with a liquid fertilizer.

The formulation compatible with a liquid fertilizer can include a hydrated aluminum-magnesium silicate and at least one dispersant. The term "in a formulation compatible with a liquid fertilizer" as used throughout the specification and claims is intended to mean that the formulation is capable of dissolution or dispersion or emulsion in an aqueous solution to allow for mixing with a fertilizer for delivery to plants in a liquid formulation.

In notable embodiments, the formulation compatible with a liquid fertilizer can include bifenthrin, such as a composition comprising bifenthrin; a hydrated aluminum-magnesium silicate; and at least one dispersant selected from a sucrose ester, a lignosulfonate, an alkylpolyglycoside, a naphthalenesulfonic acid formaldehyde condensate and a phosphate ester. The bifenthrin can be preferably present in a concentration of from 1.0% by weight to 35% by weight, more particularly, from 15% by weight to 25% by weight based upon the total weight of all components in the composition. The bifenthrin insecticide composition can be present in the liquid formulation at a concentration ranging from 0.1 g/ml to 0.2 g/ml. The bifenthrin insecticide may be present in the liquid formulation at a concentration of 0.17 g/ml. The dispersant or dispersants can preferably be present in a total concentration of from about 0.02% by weight to about 20% by weight based upon the total weight of all components in the composition. In some embodiments, the hydrated aluminum-magnesium silicate may be selected from the group consisting of montmorillonite and attapulgite. In some embodiments, the phosphate ester may be selected from a nonyl phenol phosphate ester and a tridecyl alcohol ethoxylated phosphate potassium salt.

The dispersant or dispersants can preferably be present in a total concentration of from about 0.02% by weight to about 20% by weight based upon the total weight of all components in the composition.

In some embodiments, the hydrated aluminum-magnesium silicate can be selected from the group consisting of montmorillonite and attapulgite.

In some embodiments, the phosphate ester can be selected from a nonyl phenol phosphate ester and a tridecyl alcohol ethoxylated phosphate potassium salt.

Other embodiments can further include at least one of an anti-freeze agent, an anti-foam agent and a biocide.

In another aspect, the compositions may be prepared by a process following the steps of combining the biological active ingredients in effective amounts with carriers and adjuvants as described herein. The formulated compositions can be prepared e.g. by mixing the biological active agents with the formulation components in order to obtain compositions in the form of finely divided solids, granules or dispersions. The active ingredients can also be formulated with other components, such as finely divided solids, mineral oils, oils of vegetable or animal origin, modified oils of vegetable or animal origin, organic solvents, water, surface-active substances or combinations thereof.

In some embodiments, the components of the formulation can be dry mixed, or solid and liquid components may be blended together in a homogenizer or other suitable mixing vessel. Simple mixing of the ingredients by homogenization may be preferable to any form of grinding. In other embodiments, the mixture may further undergo a milling process, such as dry milling or wet milling, until suitable particle sizes ranging from about 1 to about 250 microns are obtained. The composition may have particle sizes of less than 250, less than 100 or preferably less than 50 microns. In a preferred embodiment, the mixture is homogenized or milled until 90% of the particle size (D90) is less than about 50 microns.

One embodiment is directed to a composition comprising: i) the Bacillus thuringiensis RTI545 deposited as ATCC No. PTA-122161, or a mutant thereof having all the identifying characteristics thereof; and ii) at least one formulation component selected from the group consisting of adjuvants for an SC formulation; adjuvants for a WP formulation; and adjuvants for a WG formulation.

In another embodiment, the composition is in the form of an SC, such as one comprising water and at least one surfactant, and one or more additional adjuvants selected from thickeners, solvents, preservatives, antifreeze agents, pH-modifiers, and antifoam agents.

In an embodiment, the SC comprises from 1 to 20 weight % of Bacillus thuringiensis RTI545 deposited as ATCC No. PTA-122161, or a mutant thereof having all the identifying characteristics thereof; 1 to 5 weight % of one or more surfactants; and optionally at least one thickener, solvent, preservative, antifreeze agent, or antifoam agent; and water. The optional thickener, solvent, preservative, antifreeze agent, or antifoam agent may each independently comprise up to about 1 weight % of the SC formulation. The SC comprises water in a complementary amount to all the other components to bring the total composition to 100 weight % (qs).

The composition may be in solid form, for example a dust, powder, granule, WP or WG formulation. These formulations comprise at least one solid carrier as described above. In embodiments, WP or WG formulations may comprise from about 1 to about 50 weight %, such as from 1 to 10, 5 to 10, or 5 to 50, or 7 to 50, or 10 to 50 weight %, of Bacillus thuringiensis RTI545 deposited as ATCC No. PTA-122161, or a mutant thereof having all the identifying characteristics thereof; and at least one solid carrier selected from the group consisting of maltodextrin, calcium carbonate and silica. Wettable granule formulations are similar to wettable powder formulations, except that the powder is formed into larger granules, for example by diluting the powder in water optionally with additional dispersant, and forming granules by agglomeration, spray drying or extrusion.

In an embodiment, the composition may comprise from 2 to 20 weight % of Bacillus thuringiensis RTI545 deposited as ATCC No. PTA-122161, or a mutant thereof having all the identifying characteristics thereof; from about 80 to about 90 weight % of maltodextrin, and about 0.5 to about 2 weight % of silica.

In another embodiment, the composition may comprise from 5 to 60 (such as 40%) Bacillus thuringiensis RTI545 deposited as ATCC No. PTA-122161, or a mutant thereof having all the identifying characteristics thereof; from about 30 to about 50 (such as 40%) weight % of maltodextrin, about 10 to 20 (such as 16%) weight % of calcium carbonate and about 0.5 to about 5 (such as 4%) weight % of silica.

In another embodiment, the composition comprises a wettable powder or wettable granule formulation comprising by weight %:

5-50% (such as 40%) of Bacillus thuringiensis RTI545 deposited as ATCC No. PTA-122161, or a mutant thereof having all the identifying characteristics thereof;

5-15% (such as 10%) maltodextrin;

35-45% (such as 40%) calcium carbonate; and 5-15% (such as 10%) silica.

The composition may be useful in either plant seed treatment or in-furrow applications. For seed treatment, a solution, slurry, paste, gel or moistened solid of the composition can be applied to seed using standard seed treatment procedures. The composition may be applied to untreated seeds or seeds that have been treated with at least one additional crop protection agent as described herein. Alternatively, the composition may also be mixed with an additional crop protection agent for seed treatment or in-furrow applications.

In furrow applications can include treating the soil in the furrow, preferentially in proximity to the crop seeds at the time of planting, and incorporating the formulation into the soil. In furrow applications can include liquid or solid formulations. In some embodiments, the in-furrow applications comprise applying the composition in a foam.

In embodiments, the formulated compositions can be in the form of concentrates that are diluted prior to use, although ready-to-use formulations can also be made. Whereas commercial products will preferably be formulated as concentrates, the end user will normally employ dilute formulations for application to the soil or plant. The dilutions can be made, for example, with water, liquid fertilizers, micronutrients, biological organisms, oil or solvents.

In embodiments, the formulated compositions may additionally include an additive comprising an oil of vegetable or animal origin, a mineral oil, alkyl esters of such oils or mixtures of such oils and oil derivatives. The amount of oil additive in the composition according to the invention is generally from 0.01 to 10%, based on the spray mixture. For example, the oil additive can be added to the spray tank in the desired concentration after the spray mixture has been prepared. In embodiments, oil additives may comprise mineral oils or an oil of vegetable origin, for example soybean oil, rapeseed oil, olive oil or sunflower oil, emulsified vegetable oil, alkyl esters of oils of vegetable origin, for example the methyl derivatives, or an oil of animal origin, such as fish oil or beef tallow.

EXAMPLES

The following Examples have been included to provide guidance to one of ordinary skill in the art for practicing representative embodiments of the presently disclosed subject matter. In light of the present invention and the general level of skill in the art, those of skill can appreciate that the following Examples are intended to be exemplary only and that numerous changes, modifications, and alterations can be employed without departing from the scope of the presently disclosed subject matter.

Example 1

Identification of Bacterial Isolate Bacillus thuringiensis RTI545 Through Sequence Analysis A plant associated bacterial strain, designated herein as RTI545, was isolated from the rhizosphere soil surrounding tall fescue grass in North Carolina. The genome of the strain RTI545 was sequenced, and the sequences of the 16S rRNA (SEQ ID NO.: 1) and rpoB (SEQ ID NO.: 2) genes of the RTI545 strain were compared to those of other known bacterial strains in the NCBI and RDP databases using BLAST; this placed strain RTI545 within the Bacillus cereus/thuringiensis/anthracis clade. Further phylogenetic analysis of the RTI545 strain and relevant Bacillus species was performed using Bootstrap consensus trees (1000 replicates) on the rpoB gene. The consensus tree for the rpoB gene is shown in FIG. 2. As can be seen in FIG. 2, the RTI545 strain forms a separate branch in the Bacillus cereus/thuringiensis/anthracis clade. The differences in sequence for the rpoB gene at the DNA level indicate that RTI545 is a new strain falling within the Bacillus cereus/thuringiensis/anthracis clade. Additional sequence analysis revealed that the RTI545 strain lacks the genes for crystal proteins (cry genes) often found in B. thuringiensis strains.

In addition, whole genome sequence analysis was performed to compare the RTI545 strain with closely related strains of the Bacillus species using both MUMmer- and BLASTn-based Average Nucleotide Identity (ANI) calculations (Richter M, & Rosselló-Móra R (2009) Shifting the genomic gold standard for the prokaryotic species definition. Proc Natl Acad Sci USA 106(45):19126-31) and UNIPEPT analysis (Mesuere, B., Debyser, G., Aerts, M., Devreese, B., Vandamme, P. and Dawyndt, P. (2015), The Unipept metaproteomics analysis pipeline. Proteomics, 15: 1437-1442. doi:10.1002/pmic.201400361) to confirm its phylogenetic classification. The results of the MUMmer and BLASTn based ANI calculations are shown in Table I below. Both the ANI and UNIPEPT (data not shown) analyses revealed a significant degree of sequence similarity between RTI545 and published sequences of strains indicated as both B. thuringiensis and B. cereus. The highest sequence similarity to a recognized type strain was to the recognized type strain B. thuringiensis Berliner ATCC10792. Again, the differences in whole genome sequence from those previously published indicate that RTI545 is a new Bacillus thuringiensis strain falling within the Bacillus cereus/thuringiensis/anthracis clade.

TABLE I

Sequence analysis (both MUMmer and BLASTn based ANI calculations) comparing strain RTI545 with relevant Bacillus species strains.

| | B. thuringiensis RTI545 | |
|---|---|---|
| Strain | ANI (BLAST) | ANI (MUMmer) |
| B. cereus UW85 | 98.48 | 98.91 |
| B. cereus CMCC P0011 | 97.59 | 98.11 |
| B. cereus CMCC P0021 | 97.59 | 98.11 |
| B. thuringiensis Berliner ATCC 10792* | 97.51 | 98.17 |
| B. thuringiensis Bt407 | 97.32 | 98.26 |
| B. thuringiensis subsp. chinensis CT-43 | 97.21 | 98.17 |
| B. thuringiensis YBT-1518 | 97.18 | 98.11 |
| B. cereus ATCC 14579* | 95.92 | 96.78 |
| B. cereus B4264 | 95.84 | 96.70 |
| B. thuringiensis subsp. tolworthi: Pasteur | 95.99 | 96.66 |
| B. bombysepticus Wang | 95.86 | 96.52 |
| B. thuringiensis subsp. kurstaki HD 1 | 95.57 | 96.37 |
| B. cereus ATCC 4342 | 91.01 | 92.02 |
| B. cereus 03BB87 | 91.01 | 92.04 |
| B. anthracis Ames A0462 | 90.67 | 91.71 |
| B. anthracis Sterne | 90.65 | 91.71 |
| B. weihenstephanensis DSM11821 | 88.64 | 90.04 |
| B. mycoides Rock 1-4 | 81.51 | 86.11 |
| B. cytotoxicus NVH 391-98 | 80.01 | 85.31 |
| B. subtilis BAB-1 | 66.74 | 83.22 |
| B. subtilis 168 | 66.70 | 85.58 |
| B. amyloliquefaciens (B. velezensis) FZB42 | 66.22 | 85.34 |
| B. velezensis YAU B9601-Y2 | 66.21 | 85.15 |
| Enterobacter 638 | 63.92 | 82.06 |
| P. furiosus DSM3638 | 62.16 | 0.00 |

Note:
*indicates recognized type strains for both Bacillus thuringiensis and Bacillus cereus.

The strain of RTI545 was deposited on 12 May 2015 under the terms of the Budapest Treaty on the International Recognition of the Deposit of Microorganisms for the Purposes of Patent Procedure at the American Type Culture Collection (ATCC) in Manassas, Va., USA and bears the Patent Accession No. PTA-122161.

```
RTI545 genomic 165 rDNA 1
                                                    (SEQ ID NO: 1)
AGAAAGGAGGTGATCCAGCCGCACCTTCCGATACGGCTACCTTGTTACGA

CTTCACCCCAATCATCTGTCCCACCTTAGGCGGCTGGCTCCAAAAAGGTT

ACCCCACCGACTTCGGGTGTTACAAACTCTCGTGGTGTGACGGGCGGTGT

GTACAAGGCCCGGGAACGTATTCACCGCGGCATGCTGATCCGCGATTACT

AGCGATTCCAGCTTCATGTAGGCGAGTTGCAGCCTACAATCCGAACTGAG

AACGGTTTTATGAGATTAGCTCCACCTCGCGGTCTTGCAGCTCTTTGTAC

CGTCCATTGTAGCACGTGTGTAGCCCAGGTCATAAGGGGCATGATGATTT

GACGTCATCCCCACCTTCCTCCGGTTTGTCACCGGCAGTCACCTTAGAGT

GCCCAACTTAATGATGGCAACTAAGATCAAGGGTTGCGCTCGTTGCGGGA

CTTAACCCAACATCTCACGACACGAGCTGACGACAACCATGCACCACCTG

TCACTCTGCTCCCGAAGGAGAAGCCCTATCTCTAGGGTTTTCAGAGGATG
```

-continued

TCAAGACCTGGTAAGGTTCTTCGCGTTGCTTCGAATTAAACCACATGCTC

CACCGCTTGTGCGGGCCCCCGTCAATTCCTTTGAGTTTCAGCCTTGCGGC

CGTACTCCCCAGGCGGAGTGCTTAATGCGTTAACTTCAGCACTAAAGGGC

GGAAACCCTCTAACACTTAGCACTCATCGTTTACGGCGTGGACTACCAGG

GTATCTAATCCTGTTTGCTCCCCACGCTTTCGCGCCTCAGTGTCAGTTAC

AGACCAGAAAGTCGCCTTCGCCACTGGTGTTCCTCCATATCTCTACGCAT

TTCACCGCTACACATGGAATTCCACTTTCCTCTTCTGCACTCAAGTCTCC

CAGTTTCCAATGACCCTCCACGGTTGAGCCGTGGGCTTTCACATCAGACT

TAAGAAACCACCTGCGCGCGCTTTACGCCCAATAATTCCGGATAACGCTT

GCCACCTACGTATTACCGCGGCTGCTGGCACGTAGTTAGCCGTGGCTTTC

TGGTTAGGTACCGTCAAGGTGCCAGCTTATTCAACTAGCACTTGTTCTTC

CCTAACAACAGAGTTTTACGACCCGAAAGCCTTCATCACTCACGCGGCGT

TGCTCCGTCAGACTTTCGTCCATTGCGGAAGATTCCCTACTGCTGCCTCC

CGTAGGAGTCTGGGCCGTGTCTCAGTCCCAGTGTGGCCGATCACCCTCTC

AGGTCGGCTACGCATCGTTGCCTTGGTGAGCCGTTACCTCACCAACTAGC

TAATGCGACGCGGGTCCATCCATAAGTGACAGCCGAAGCCGCCTTTCAAT

TTCGAACCATGCAGTTCAAAATGTTATCCGGTATTAGCCCCGGTTTCCCG

GAGTTATCCCAGTCTTATGGGCAGGTTACCCACGTGTTACTCACCCGTCC

GCCGCTAACTTCTTGAGAGCAAGCTCTCAATCCATTCGCTCGACTTGCAT

GTATTAGGCACGCCGCCAGCGTTCATCCTGAGCCAGGATCAAAC

RTI545 rpoB gene (SEQ ID NO: 2)

TTGACAGGTCAACTAGTTCAATACGGACGCCACCGCCAACGAAGAAGTTA

TGCCCGTATTAGTGAAGTATTAGAGTTACCAAATCTTATCGAAATTCAAA

CCTCTTCTTATCAGTGGTTTCTTGATGAGGGTTTGCGAGAAATGTTCCAA

GACATTTCTCCGATTGAAGACTTTACGGGAAATCTATCGCTTGAATTTAT

CGACTACAGCTTAGGTGAACCTAAATACTCTGTAGACGAATGCAAAGAGC

GTGATGTGACGTATGCAGCACCACTTCGTGTAAAAGTGCGTCTAATCAAC

AAGGAAACTGGTGAAGTAAAAGAACAAGATGTGTTCATGGGAGATTTCCC

ACTCATGACAGAGACTGGAACATTCGTAATTAACGGTGCAGAACGTGTTA

TCGTTTCCCAGTTAGTTCGCTCTCCAAGCGTATACTATAGTGGCAAAGTG

GATAAAAACGGAAAACGTGGTTTTACTGCTACTGTAATTCCAAACCGCGG

AGCTTGGTTAGAGTATGAGACAGATGCTAAGGATGTTGTATATGTGCGTA

TTGACCGTACGCGTAAACTTCCTGTAACTGTTTTGTTACGCGCATTAGGG

TTTGGCTCTGATCAAGAAATCACCGAGCTTTTAGGTGATAACGAATACTT

AAGCAACACATTAGAAAAAGACAACACAGATAGTACAGAAAAAGCATTGC

TTGAAATTTATGAGCGTCTACGTCCTGGTGAACCACCAACAGTAGAAAAT

GCTAAGAGCTTACTTGTGTCTCGTTTCTTCGATCCAAAGCGCTACGATTT

AGCAAATGTAGGTCGCTATAAGATCAACAAGAAGTTACACATTAAAAACA

GATTGTTTAATCAACGTTTAGCTGAAACATTAGTGGATCCAGAAACTGGT

-continued

GAAATTTTAGCGGCAGAAGGAACAATCTTAGATCGTCGTACACTTGATCG

CATTTTACCTTACTTAGAGAAAAACATTGGATTCAAAACAGCGAAACCAA

TGGGTGGAGTGGTAGAAGGCGATGTTGAGCTGCAATCTATTAAGATTTAT

GCTCCTGAGTCGGAAGGCGAACGTGTAATTAATGTAATTGGTAATGCAAA

TATTACTCGTGATGTGAAACACATCACACCAGGTGATATCCTTGCTTCTA

TCAGTTACTTCTTCAACCTACTATACAAAGTAGGGGATACAGATGATATT

GACCATTTAGGAAACCGTCGTCTGCGTTCTGTTGGAGAACTATTACAAAA

TCAATTCCGTATCGGTCTTTCTCGTATGGAACGTGTTGTTCGTGAGAGAA

TGTCGATCCAAGATACAAATGCAATTACACCACAGGCGCTAATTAATATT

CGTCCTGTTATTGCATCTATTAAAGAGTTCTTCGGAAGTTCTCAGTTATC

TCAGTTCATGGACCAAACAAATCCATTAGCAGAGTTAACTCACAAACGAA

GACTATCTGCATTAGGACCTGGTGGTTTAACGCGTGAGCGCGCAGGCTTT

GAAGTACGTGACGTTCATTACTCCCACTACGGTCGTATGTGTCCGATTGA

AACACCAGAGGGACCAAACATCGGTTTGATTAACTCATTATCTTCGTTCG

CGAAAGTAAATGAGTTTGGTTTCATTGAAACACCATATCGTCGTGTTGAC

CCAGAAACTGGTCTTGTAACAGGGCATGTTGATTATTTAACAGCAGATGA

AGAAGATAACTATGTTGTAGCCCAAGCGAATATGAAATTATCTGATGAAG

GTGAATTCCTAAGTGAAGATATCGTAGCTCGTTTCCGTGGTGAAAACATT

GTCACAAATAGAGAACGCATCGACTACATGGATGTATCTCCAAAACAAGT

AGTGTCGGCAGCGACAGCTTGTATTCCGTTCTTAGAAAACGATGACTCTA

ACCGCGCACTTATGGGAGCGAACATGCAACGTCAGGCGGTTCCGTTAATG

AATCCGGAATCTCCGATTGTAGGTACAGGTATGGAGTACGTATCAGCAAA

AGACTCAGGTGCTGCAGTAATCTGTAAACATCCTGGTGTTGTTGAGCGCG

TAGAAGCACGTGAAGTTTGGGTACGTCGCTATGTAGAAGTTGACGGTCAA

ACAGTAAAAGGCGACTTAGATCGCTACAAAATGCAAAAATTCATTCGTTC

TAACCAAGGAACTTGTTACAACCAACGTCCAATCGTAAGTGTTGGAAATG

AAGTTGTAAAAGGTGAAATCCTTGCGGATGGTCCTTCTATGGAATTAGGT

GAACTAGCACTTGGACGTAACGTGCTTGTTGGCTTCATGACTTGGGACGG

TTATAACTACGAGGATGCGATCATCATGAGTGAGCGCCTTGTAAAAGATG

ATGTGTACACTTCTATTCATATTGAAGAATATGAATCAGAAGCTCGTGAT

ACGAAGCTTGGACCAGAAGAAATTACACGTGACATTCCAAATGTTGGGGA

AGACGCATTACGTAACCTTGACGAGCGCGGTATCATTCGCGTTGGTGCTG

AAGTAAAAGATGGAGATTTACTTGTTGGTAAAGTAACACCTAAAGGTGTA

ACAGAATTAACAGCTGAAGAACGTCTATTACATGCTATCTTTGGAGAAAA

AGCGCGTGAAGTACGTGATACATCACTACGTGTACCACACGGTGGTGGCG

GTATTATCTTAGACGTAAAAGTATTCAACCGTGAAGATGGCGATGAATTG

CCACCAGGCGTGAATCAACTTGTACGTGCATATATCGTTCAAAAACGTAA

AATTTCTGAAGGTGACAAGATGGCCGGACGTCACGGTAACAAAGGTGTTA

TTTCTCGTATTTTACCAGAAGAAGATATGCCTTACTTACCAGACGGTACG

CCAATCGATATCATGTTAAACCCATTAGGGGTACCATCTCGTATGAATAT

CGGTCAGGTATTAGAGCTTCATCTTGGTATGGCAGCAAGATACCTGGGCA

-continued

TTCACATTGCAACACCAGTATTCGATGGTGCTCGTGAGGAAGATGTTTGG

GGCACAATTGAAGAAGCTGGTATGGCAAATGACGCGAAAACAATCCTGTA

TGACGGACGTACTGGTGAACCATTCGATAACCGCGTATCTGTTGGTGTCA

TGTATATGATCAAACTTGCGCACATGGTTGACGATAAACTTCATGCTCGT

TCTACTGGACCATACTCACTTGTAACGCAGCAACCTCTTGGAGGTAAAGC

TCAGTTCGGTGGACAGCGTTTCGGTGAGATGGAGGTTTGGGCACTTGAAG

CTTACGGTGCTGCTTATACTCTTCAAGAAATCTTAACAGTGAAGTCTGAT

GATGTTGTTGGACGTGTTAAGACTTATGAAGCAATTGTTAAAGGCGAAAA

TGTTCCAGAACCAGGCGTTCCTGAATCATTCAAAGTATTGATTAAAGAGC

TGCAAAGTTTAGGTATGGACGTTAAAATGATGTCTAGCGACGATACAGAA

ATTGAAATGCGTGATACAGAAGATGACGATGATCATCAATCAGCAGATAA

ATTGAATGTCGAAGTTGAGACAACTAAGGAATAA

Example 2

Anti-Microbial Properties of Bacillus Thuringiensis RTI545 Isolate

The antagonistic ability of strain RTI545 against major plant pathogens was measured in plate assays. A plate assay for evaluation of antagonism against plant fungal pathogens was performed by growing the bacterial isolate and pathogenic fungi side by side on 869 agar plates at a distance of 3-4 cm. Plates were incubated at room temperature and checked regularly for up to two weeks for growth behaviors such as growth inhibition, niche occupation, or no effect. In the case of screening for antagonistic properties against bacterial pathogens, the pathogen was first spread as a lawn on 869 agar plates. Subsequently, 20 μl aliquots of a culture of RTI545 were spotted on the plate. Plates were incubated at room temperature and checked regularly for up to two weeks for an inhibition zone in the lawn around the positions were RTI545 had been applied. A summary of the antagonism activity is shown in Table II below.

TABLE II

Antagonistic properties of Bacillus thuringiensis RTI545 isolate against major plant pathogens

| | Anti-Microbial Assays | RTI545 |
|---|---|---|
| Fungal Pathogens | Alternaria solani | + |
| | Aspergillus flavus | ++ |
| | Botrytis cinerea | ++ |
| | Cercospora sojina | + |
| | Fusarium colmorum | +– |
| | Fusarium graminearum | ++ |
| | Fusarium oxysporum | ++ |
| | Fusarium oxysporum f. sp. Cubense | + |
| | Fusarium virguliforme | ++ |
| | Glomerella cingulata | +++ |
| | Magnaporthe grisea | ++ |
| | Monilina fructicola | +++ |
| | Phytophthora capsici | –/+– |
| | Pythium sylvatium | + |
| | Pythium aphandermatum | + |
| | Rhizoctonia solani | ++ |
| | Sclerotinia homeocarpa | ++ |
| | Sclerotinia sclerotiorum | +++ |
| | Stagonospora nodorum | +++ |

TABLE II-continued

Antagonistic properties of Bacillus thuringiensis RTI545 isolate against major plant pathogens

| | Anti-Microbial Assays | RTI545 |
|---|---|---|
| Bacterial Pathogens | Erwinia amylovora | + |
| | Pseudomonas syringae pv. tomato | – |
| | Xanthomonas euvesicatoria | – |

+++ very strong activity,
++ strong activity,
+ activity,
+– weak activity,
– no activity observed

Example 3

Phenotypic Traits of Bacillus Thuringiensis RTI545 Isolate

In addition to the antagonistic properties, various phenotypic traits were also measured for the Bacillus thuringiensis RTI545 strain and the data are shown below in Table III. The assays were performed according to the procedures described in the text below Table III.

TABLE III

Phenotypic Assays: phytohormone production, acetoin and indole acetic acid (IAA), and nutrient cycling of RTI545 isolate.

| Characteristic Assays | RTI545 |
|---|---|
| Acid Production (Methyl Red) | + |
| Acetoin Production (MR-VP) | +++ |
| Chitinase | – |
| Indole-3-Acetic Acid production | – |
| Protease activity | +++ |
| Phosphate Solubilization | +– |
| Phenotype | Cream, somewhat dry with texture/wrinkles in colony, and the strain exhibits robust growth at 10° C. |

+++ very strong,
++ strong,
+ some,
+– weak,
– none observed

Acid and Acetoin Test. 20 μl of a starter culture in rich 869 media was transferred to 1 ml Methyl Red—Voges Proskauer media (Sigma Aldrich 39484). Cultures were incubated for 2 days at 30° C. 200 rpm. 0.5 ml culture was transferred and 50 μl 0.2 g/l methyl red was added. Red color indicated acid production. The remaining 0.5 ml culture was mixed with 0.3 ml 5% alpha-napthol (Sigma Aldrich N1000) followed by 0.1 ml 40% KOH. Samples were interpreted after 30 minutes of incubation. Development of a red color indicated acetoin production. For both acid and acetoin tests non-inoculated media was used as a negative control (Sokol et al., 1979, Journal of Clinical Microbiology. 9: 538-540).

Indole-3-Acetic Acid. 20 μl of a starter culture in rich 869 media was transferred to 1 ml 1/10 869 Media supplemented with 0.5 g/l tryptophan (Sigma Aldrich T0254). Cultures were incubated for 4-5 days in the dark at 30° C., 200 RPM. Samples were centrifuged and 0.1 ml supernatant was mixed with 0.2 ml Salkowski's Reagent (35% perchloric acid, 10 mM $FeCl_3$). After incubating for 30 minutes in the dark, samples resulting in pink color were recorded positive for IAA synthesis. Dilutions of IAA (Sigma Aldrich 15148) were used as a positive comparison; non inoculated media was used as negative control (Taghavi, et al., 2009, Applied and Environmental Microbiology 75: 748-757).

Phosphate Solubilizing Test.

Bacteria were plated on Pikovskaya (PVK) agar medium consisting of 10 g glucose, 5 g calcium triphosphate, 0.2 g potassium chloride, 0.5 g ammonium sulfate, 0.2 g sodium chloride, 0.1 g magnesium sulfate heptahydrate, 0.5 g yeast extract, 2 mg manganese sulfate, 2 mg iron sulfate and 15 g agar per liter, pH7, autoclaved. Zones of clearing were indicative of phosphate solubilizing bacteria (Sharma et al., 2011, Journal of Microbiology and Biotechnology Research 1: 90-95).

Chitinase Activity.

10% wet weight colloidal chitin was added to modified PVK agar medium (10 g glucose, 0.2 g potassium chloride, 0.5 g ammonium sulfate, 0.2 g sodium chloride, 0.1 g magnesium sulfate heptahydrate, 0.5 g yeast extract, 2 mg manganese sulfate, 2 mg iron sulfate and 15 g agar per liter, pH7, autoclaved). Bacteria were plated on these chitin plates; zones of clearing indicated chitinase activity (N. K. S. Murthy & Bleakley., 2012. "Simplified Method of Preparing Colloidal Chitin Used for Screening of Chitinase Producing Microorganisms". The Internet Journal of Microbiology. 10(2)).

Protease Activity.

Bacteria were plated on 869 agar medium supplemented with 10% milk. Clearing zones indicated the ability to break down proteins suggesting protease activity (Sokol et al., 1979, Journal of Clinical Microbiology. 9: 538-540).

Example 4

Effects of Bacillus thuringiensis Isolate RTI545 on Corn Seed Germination

The effect of vegetative cells of the bacterial isolate RTI545 on corn seed germination was determined as described below.

Assays with vegetative cells of RTI545 were performed using seeds from corn. RTI545 was plated onto 869 media from a frozen stock and grown overnight at 30° C. An isolated colony was taken from the plate and inoculated into a 50 mL conical tube containing 20 mL of 869 broth. The culture was incubated overnight with shaking at 30° C. and 200 RPM. The overnight culture was centrifuged at 10,000 RPM for 10 minutes. Supernatant was discarded and pellet was resuspended in $MgSO_4$ to wash. The mixture was centrifuged again for 10 minutes at 10,000 RPM. The supernatant was discarded and the pellet was resuspended in Modified Hoagland's solution. The mixture was then diluted to provide an initial concentration. From this, dilutions of the RTI545 culture were made to have a final concentration of $2\times10^7$ cfu/ml. For the seed germination experiments on corn, plant growth containers were labeled with RTI545 or control. Ten (10) seeds were placed in a single container. Ten mL of the RTI545 suspension with a concentration of $2\times10^7$ cfu/ml was added to the containers and the seeds were incubated at 21° C. in the dark. Control containers contained seeds and Modified Hoagland's solution without added bacteria. Images of the containers were taken after 10 to 12 days. FIGS. 3A-3B are images of the corn seedlings after 12 days grown in the presence (FIG. 3A) and absence (FIG. 3B) of the RTI545 strain. As can be seen in the figures, the presence of the RTI545 strain resulted in a significant growth advantage.

Example 5

Growth Effects of Bacillus thuringiensis RTI545 Isolate in Corn

The effect of application of the bacterial isolate on early plant growth and vigor in corn was determined. The experiment was performed by inoculating surface sterilized germinated corn seeds for 2 days in a suspension of $10^8$ CFU/ml of the bacterium at room temperature under shaking (a control was also performed without bacteria). Subsequently, the innoculated seeds were planted in 1 gallon pots filled with PROMIX BX which was limed to a pH of 6.5. For each treatment 9 pots were seeded with a single corn seed. Pots were incubated in the greenhouse at 22° C. with light and dark cycle of 14/10 hrs and watered twice a week as needed.

Forty two days after planting, plants were harvested and their fresh and dry weight were measured and compared to data obtained for non-inoculated control plants. The wet and dry weight of the corn shoot biomass was measured after 42 days growth. Wet weight of the corn shoot biomass was equal to 173.7 g for the plants inoculated with the Bacillus thuringiensis RTI545 strain versus a wet weight equal to 147.6 g for the non-inoculated control which is a 17.7% increase in wet weight over the non-inoculated control. Dry weight of the corn shoot biomass was equal to 16.0 g for the plants inoculated with the Bacillus thuringiensis RTI545 strain versus a dry weight equal to 12.4 g for the non-inoculated control which is a 29% increase in dry weight over the non-inoculated control. As can be discerned from the significant increase in both wet and dry biomass, the presence of the RTI545 strain resulted in a significant growth advantage.

Example 6

Activity of Bacillus thuringiensis RTI545 Isolate Against Insects

The ability of the Bacillus thuringiensis RTI545 strain to antagonize Western Plant Bug (WPB), Lygus hesperus, and Southern Corn Rootworm (SCRW), Diabrotica undecimpunctata howardi, was evaluated in in vitro assays.

For the assays Bacillus thuringiensis RTI545 was grown for 7 hours in 5 ml of 869 medium, at 200 rpm, and at 30° C. Subsequently, a small portion of the pre-culture was diluted 100-fold into 869 medium and grown for 17 hours at 150 rpm at 30° C. The entire bacterial culture was used in all bioassays. As a biological control, Bacillus thuringiensis subsp. kurstaki HD-1 was used according to the same protocol.

For antagonism against WPB, Bacillus thuringiensis RTI545 was evaluated in direct spray, choice feeding, and no-choice feeding assays along with the controls: 869 medium blank, chemical control ACEPHATE 97UP (A.I.=97% O,S-Dimethyl acetylphosphoramidothioate), biological control HD-1, and an untreated control. As expected, no significant mortality (direct spray and no-choice feeding assays) or repellency (choice feeding assay) was observed for the 869 medium blank or HD-1 treatments, while the chemical control killed (direct spray and no-choice feeding assays) and repelled (choice feeding assay) the WPB. Bacillus thuringiensis RTI545 provided no significant mortality to WPB when applied in both direct spray and in no-choice feeding assays; however, unexpectedly, RTI545 displayed a repellent behavior at 124 hours after WPB were placed into choice assay arenas. Specifically, when the WPB were placed into a container containing a treated and a non-treated food source, WPB were observed to be feeding only on the untreated food source (data not shown).

For antagonism against SCRW larvae, Bacillus thuringiensis RTI545 cells were evaluated in a choice feeding assay of corn seedlings and compared to a water control. Additional treatments compared to the water control were i) Bacillus thuringiensis subsp. kurstaki HD-1 (HD-1), ii) chemical control CAPTURE LFR (A.I.=17.15% bifenthrin), and iii) 869 medium. Filter paper was cut in half and each section taped down within a 100 mm petri dish, making sure that each of the two halves of filter paper did not touch. A total volume of 0.65 ml of treatment was applied to the treated filter paper half. Deionized water was applied to the untreated side. For the untreated control, both halves of the filter paper were treated with water only. One germinated corn seed was situated on each moist filter paper half. Ten second-instar larvae were placed at the midline between treated and untreated filter paper. There were 3 replicates per treatment. Dishes were sealed with PARAFILM and maintained in a dark environment at room temperature for 6 days prior to assessment. The location and number of dead larvae were recorded. The proportion of larvae on each section of filter paper was square root transformed to normalize distribution and statistically analyzed with ANOVA. Utilization of post-hoc Tukey HSD test was used to determine if differences between untreated and treated filter paper were significant ($\alpha$=0.10).

An image of the plate assay with the RTI545 cells after 6 days is shown in FIG. 4, and the data from all of the plate assays are summarized in Table IV below. As was observed in the assay above for WPB, the RTI545 unexpectedly repelled, but did not kill the SCRW larvae. As can be seen in FIG. 4 and Table IV, the RTI545 cultures were excellent at repelling the SCRW larvae; 100% of the larvae were present on the water-treated half of the filter paper and none of the larvae on the RTI545 treated paper. In contrast, the larvae were statistically evenly divided between treatment and water control for the HD-1 strain. The bifentrin chemical control resulted in about 19% of the larvae present on the CAPTURE LFR-treated filter paper. The results show that the RTI545 strain was unexpectedly superior to a chemical insecticide at repelling the insects from the corn seed, but did not kill the insects.

TABLE IV

Percent of living SCRW larvae located on the treatment and water-treated halves of the filter paper after 6 days in a choice feeding assay on corn.

| Percent Alive on Filter Paper | Treatment | | | | |
|---|---|---|---|---|---|
| | RTI545 | HD-1 | CAPTURE LFR | 896 Medium | Water |
| Treated | 0.00 | 46.66 | 19.44 | 34.81 | 56.66 |
| Water | 100.00 | 53.33 | 80.55 | 65.18 | 43.33 |
| P-Value | <0.001 | 0.671 | <0.001 | 0.012 | 0.350 |

Note:
Statistical analyses were conducted on the square root transformed proportion of larvae on treated and untreated halves of the filter paper.

The choice feeding assay for SCRW larvae using corn seedlings was repeated HD-1 strain and RTI545, Unlike HD-1, RTI545 does not contain genes for production of crystal proteins (represented as "Cry"). Repellency was measured using a choice in vitro plate feeding assay of corn seedlings by SCRW larvae and scored after 72 hours as the percentage of SCRW larvae on the non-treated side of the plate. In the case of no repellency, an equal distribution of 50% on both the treated and non-treated half of the plate would be expected, indicating 0% repellency. The results of this assay are shown in Table V below. In this experiment, the Bacillus thuringiensis RTI545 and Bacillus thuringiensis subsp. kurstaki HD-1 (HD-1), were evaluated in comparison to a water control after 3 days in the assay. Again, the RTI545 cultures were excellent at repelling the SCRW larvae; 96% of the larvae were present on the water-treated half of the filter paper and only 4% on the half containing the RTI545 cells. In contrast, the larvae were again statistically evenly divided between treatment and water control for the HD-1 strain (53% on non-treated side of plate).

TABLE V

Percent of living SCRW larvae located on the non-treated half of filter paper after 3 days in a choice feeding assay on corn.

| Bacterial Strain | Cry | % of larvae on non-treated side |
|---|---|---|
| Bacillus thuringiensis RTI545 | – | 96 |
| Bacillus thuringiensis subsp. kurstaki HD-1 | + | 53 |

The choice feeding assay for SCRW larvae using corn seedlings was also repeated to compare RTI545 to another Bacillus thuringiensis strain FD30 and kanosamine. Based on genome sequence data, the putative kanosamine biosynthesis pathway is found in RTI545 but not in FD30. Repellency was measured using a choice in vitro plate feeding assay of corn seedlings by SCRW larvae and scored after 72 hours as the percentage of SCRW larvae on the non-treated side of the plate. In the case of no repellency, an equal distribution of 50% on both the treated and non-treated half of the plate would be expected, indicating 0% repellency. The results of this assay are shown in Table VI below.

TABLE VI

Mean percent of SCRW larvae located on the untreated and treated portions of the filter paper at 3 days after introduction into the experimental arena.

| | | B. t. strain | | Kanosamine | | | |
|---|---|---|---|---|---|---|---|
| Assay | Untreated | RTI545 | FD30 | 10 μg/ml | 100 μg/ml | 100 μg/ml + FD30 | 869 media |
| Treated | 46.67 | 16.67 | 40.00 | 16.67 | 16.67 | 6.67 | 30.0 |
| Untreated | 53.33 | 83.33 | 60.00 | 83.33 | 83.33 | 93.33 | 70.0 |
| p-value | 0.612 | <0.001 | 0.072 | 0.003 | 0.003 | 0.002 | 0.01 |

As summarized in Table VI, RTI545 provides a repellent effect to SCRW larvae when placed on the midline between treated and non-treated filter papers. FD30 (Bacillus thuringiensis) does not have the same overall effect. SCRW avoidance was observed when kanosamine was combined with the FD30 strain. In two separate bioassays, repellent effects by kanosamine, at all dilution rates between 0.1 μg/ml and 100.0 μg/ml, were observed at 24 h. In one test, kanosamine treated filter paper at 10 and 100 μg/ml provided z 80% avoidance response to SCRW. At 3 d, minimal feeding damage was observed on corn located on the kanosamine treated side. Conversely, FD30 had a non-statistical 20% difference in the number of larvae located on the treated and untreated filter paper at 3 d; noticeable feeding damage to corn was seen on both sides of the FD30 choice assay. In a second test, filter paper treated with 30.0 ug/ml of kanosamine provided complete repellency out to 5 days (data not shown). Based on these results, the ability of RTI545 to repel insect species such as WPB and SCRW may be due to its production of kanosamine.

Example 7

Activity of Bacillus thuringiensis RTI545 Isolate Against Nematodes

The results of Example 6 suggest that repellent activity of TRI545 against insect species may be due to production of compounds such as kanosamine. Similarly, activity of RTI545 against nematodes may also be due to compound(s) produced by the strain. A nematode chemotaxis assay on agar plates was conducted as described below to evaluate response of root knot (RKN) nematode juveniles (J2) to different concentrations of kanosamine and RTI545 supernatant in vitro.

The test arena is shown schematically in FIG. 6. Nine-cm-diameter Petri dishes were filled with 15 ml 0.75% Phytagel (including 0.1% $MgSO_4.7H_2O$). Magnesium Sulfate Heptahydrate $MgSO_4.7H_2O$ was used, instead of water agar, so that nematode tracks could be observed under a microscope. Wells of 0.5 cm diameter which can accommodate approximately 50 μl of solution were made at opposite sides of the dishes at 2 cm from the center. The test samples were applied in the wells and left to diffuse for 1 hour with lids on the dishes, so a gradient around the wells could be established. Then, 75-100 $J_2$ stage root-knot nematodes suspended in 5 μl of sterile distilled water were placed by pipette in the center 1.5 cm-diameter circle of the plate. When the surface tension of the water suspension was lost, the dishes were covered with lids and incubated in the dark on a leveled platform at 25° C. for 1 to 4 hours. After incubation the plates were transferred to 4° C. to stop nematode movement for scoring at 2 h, 3 h and 5 h after setup. Three replicates were done for each test material.

For scoring, the test arena was divided into sixteen zones, designated as 1-8 for attractive zones and a-h for repellent zones as shown in FIG. 6A. Nematodes attracted to the test substance would tend to move to the numbered (attractive) zones, resulting in clustering along the axis parallel to the orientation of the wells. Repelled nematodes would tend to move to the lettered (repellant) zones, resulting in clustering along the axis perpendicular to the orientation of the wells. The chemotaxis factor (Cf) was calculated by dividing the total number of nematodes in the attractant zones by the total number of nematodes in the repellent zones. A Cf greater than 2 meant attraction for the nematodes, while lower than 0.5 indicated repellence, and 0.5 to 2 was considered neutral. The results are shown in Table VII. In this chemotaxis bioassay distilled water was found to be neutral at all evaluation time points (Cf between 0.5 and 2.0). Acetic acid at 1% showed repellency to RKN J2 (Cf<0.5) at 3 h and 5 h from initiation of the test. The Cf for acetic acid at early evaluation time point of 2 h was neutral (data not shown), probably as a result of slow diffusion of the chemical into the Phytagel medium and/or delayed nematode response to the chemical. FIG. 6B is a photograph of an assay of kanosamine tested at 100 μg/ml, wherein dots representing nematode locations indicate neutral distribution. FIG. 6C is a photograph of an assay of RTI545 supernatent tested at 100% strength, wherein dots representing nematode locations indicate repellant distribution.

TABLE VII

The chemotaxis of root knot nematode (Meloidogyne spp.) in the presence of RTI545 supernatant.

| | Cf (chemotaxis factor) | |
|---|---|---|
| Treatment | at 3 h | at 5 h |
| kanosamine 1 μg/ml | 1.0 | 1.0 |
| kanosamine 10 μg/ml | 0.6 | 0.7 |
| kanosamine 100 μg/ml | 0.6 | 0.7 |
| Water | 1.0 | 1.0 |
| Acetic Acid (1%) | 0.45 | 0.4 |
| RTI545 supernatant 1% | 0.5 | 0.4 |
| RTI545 supernatant 10% | 0.2 | 0.1 |
| RTI545 supernatant 25% | 0.1 | 0.1 |
| RTI545 supernatant 50% | 0.003 | 0.03 |
| RTI545 supernatant 100% | 0.003 | 0.01 |
| 869 medium 10% | 0.1 | 0.01 |
| 869 medium 50% | 0.1 | 0.06 |
| 869 medium 100% | 0.03 | 0.02 |

All three tested concentrations of kanosamine (1, 10 and 100 μg/ml) did not show repellent properties in the assay. The Cf factor was consistently higher than 0.5 for all tested kanosamine rates and all tested time points. All tested rates of RTI545 supernatant (1%, 10%, 25%, 50% and 100%) and all rates of 869 medium (10%, 25%, 50% and 100%) act as a repellent (Cf<0.5) starting from 2 h of the initiation of the assay. Such quick response of J2 nematodes suggests that the factor responsible for nematode behavior easily diffuses and establishes a gradient. In the case of the 869 medium there was no clear dose response to tested rates. However, in the case of RTI545 supernatant, clear response to tested rates was observed: higher rates of supernatant resulted with stronger repulsion of nematodes (lower Cf). However, the results for RTI545 repellency are non-conclusive due to strong activity of 869 medium of the assay.

The absence of repellency of kanosamine to nematodes is in contrast to that observed for insect assays. Nematode repellency observed for RTI545 appears to be due to some other factor than kanosamine.

The compounds produced during overnight culture of RTI545 (Bacillus thuringiensis) strain and the pure compound kanosamine were evaluated in vitro to characterize their potential effect on hatching of root knot nematode (RKN) eggs (Meloidogyne incognita/hapla).

Bacterial Supernatants:

To obtain supernatant for the assay, one loop (10 l) of the RTI545 strain was grown for 16 h in 5 ml of 869 medium at 200 rpm at 30° C. The following day, the optical density (OD) of 1:100 dilutions was measured at 600 nm to estimate the volume needed for inoculation of fermentation flasks. The bacterial culture was started in 250 ml fermentation flasks in 25 ml of 869 medium at an initial OD of 0.01. Bacteria were grown overnight (for 16 h) at 200 rpm at 30° C. Two ml of bacterial culture was saved to measure the OD and colony forming units (CFU). The remaining culture was centrifuged (2500 rpm, 15 min) and the supernatant was filter-sterilized through a 0.22 μm filter. The hatching assay was initiated within 4 h from the supernatant collection. The supernatant was kept at 4° C. until the initiation of the bioassay.

Kanosamine (10 mg) was dissolved in 1 ml of deionized water to obtain 10 mg/ml stock solution. To obtain 200 μg/ml concentration, 20 μl of concentrated stock (10 mg/ml) was added to 990 ml of water. Serial dilutions were then made to create concentrations of 20 μg/ml and 2 μg/ml of kanosamine respectively.

A mixed culture of root knot nematodes (Meloidogyne incognita and M. hapla) was used. Nematode eggs were extracted from tomato roots by bleaching and cleaned using an Opti-prep centrifugation step followed by two washes in water. Before setting up the hatching assay, the percentage of early (eggs with a visible embryo) and late eggs (eggs with differentiated juveniles inside; J1 or J2 stages) were established by counting the eggs under a microscope. Only fresh eggs (collected at the day of the initiation of the assay) were used for the bioassay.

The assay was performed in 24-well tissue culture plates. In each well 75 μl of egg solution in 2% methyl cellulose (approximately 100 eggs per well) was mixed with 75 μl of antibiotic solution (300 mg/L streptomycin+300 mg/L penicillin) and 150 l of each treatment. Antibiotics were suspended in sterile distilled water. The final concentration of antibiotics in testing plates was 75 mg/L of penicillin and 75 mg/L of streptomycin. All treatments contained 2% methyl cellulose (RKN eggs were suspended in methyl cellulose prior to exposure to treatment). The addition of methyl cellulose increases the accuracy of adding the same number of inoculum to each treatment. The treatments were set up in 6 replications. Each plate was covered, wrapped in aluminum foil and placed in an incubator set at 25° C. The numbers of hatched juveniles in each well were counted under a stereomicroscope at 7 days and 14 days from initiation of hatching. For each time point and treatment, the percent hatching was calculated according to the formula:

$$\%\ \text{hatching} = \frac{\text{number of J2 in well}}{\text{number of eggs present in the well at the beginning of the assay}} * 100\%$$

Mean percent hatching of root-knot nematode eggs after 7 and 14 days are shown in Table VIII. All treatments were supplemented with antibiotics (75 mg/L of penicillin and 75 mg/L of streptomycin) to prevent contamination. Data are means from 6 replicates± standard deviation of the means.

TABLE VIII

Impact of treatments on nematode egg hatching %

| | Treatments | % Hatching after 7 days | % Hatching after 14 days |
|---|---|---|---|
| 1 | RTI545 - 2.5% (v/v) supernatant | 5.2 ± 1.5 | 9 ± 4 |
| 2 | RTI545 - 12.5% (v/v) supernatant | 6.9 ± 3.3 | 9.5 ± 5.3 |
| 3 | RTI545 - 25% (v/v) supernatant | 5.6 ± 1.8 | 9.6 ± 5.1 |
| 4 | RTI545 - 50% (v/v) supernatant | 5.2 ± 2.5 | 6.4 ± 2.3 |
| 5 | kanosamine - 1 μg/ml | 35.9 ± 5.2 | 40.1 ± 6.8 |
| 6 | kanosamine - 10 μg/ml | 39.4 ± 3 | 42.1 ± 12.1 |
| 7 | kanosamine - 100 μg/ml | 32.4 ± 4.8 | 41.6 ± 6.8 |
| 8 | abamectin 0.1 ppm | 24.4 ± 2.9 | 27.8 ± 5.7 |
| 9 | abamectin 1.0 ppm | 4.9 ± 0.9 | 8.5 ± 1.6 |
| 10 | medium 869 | 22.5 ± 3.5 | 28.3 ± 3.7 |
| 11 | water without antibiotics | 22.2 ± 2.6 | 30.3 ± 3.9 |
| 12 | water | 21.3 ± 1.9 | 30.9 ± 5.4 |

The percentage of early and late eggs collected for the assay was 41% and 59%, respectively. The antibiotics, lower rate of Agrimek® (0.1 ppm) and 869 media blank did not have a significant effect on egg hatching. The chemical standard Agrimek® inhibited egg hatching in vitro. The rate of 1 ppm caused 72% egg hatching inhibition after 14 days. The hatching in any rate RTI545 supernatant and in the high rate of Agrimek® (1 ppm) was significantly lower than in the water control. A dose response was not observed among the tested RTI545 rates (2.5%-50%), as well as all these rates were comparable to the chemical standard Agrimek®. In contrast, the hatching rate of eggs exposed to various concentrations of kanosamine (1, 10 and 100 μg/ml) was higher than in water control.

RTI545 supernatant from overnight culture on 869 medium at all tested rates significantly inhibited egg hatching. Similar results were observed when RTI545 supernatant was collected from 3 days culture grown on the same medium (data not shown). The compounds responsible for egg hatching inhibition are present in cultures that were growth overnight and for 3 days.

Kanosamine had a positive effect on egg hatching. The hatching rate of eggs exposed to kanosamine was up to 80% higher than hatching rate of eggs incubated in water control after seven days. These results are in agreement with biochemical properties of kanosamine. Kanosamine was identified as chitin synthesis inhibitor (Janiak and Milewski, 2001). Nematode egg shell is composed of chitin and egg hatching involves chitin degradation—the opposite process to chitin synthesis.

While not intending to be bound by any theory, the results from the assays suggest that the anti-nematode activity of RTI545 is not due to kanosamine. The different behavior of RTI545 supernatants and 869 media extracts in the repellency and egg hatching assays suggests that RTI545 produces an as-yet unidentified compound that provides anti-nematode performance.

Example 8

Effects on Growth and Yield by Treating Corn and Soybean Seed with Bacillus thuringiensis RTI545

Experiments were performed to determine the effect on growth and yield under insect pressure by treating corn and soybean seed with spores of B. thuringiensis RTI545, in combination with a chemical insecticide.

The effects on one or more of growth, yield, and control of the corn pests wireworm and seed maggot were measured in field trials in Wisconsin. Additional experiments were performed in the greenhouse to measure the effect on early plant growth in the presence of wireworm. The experiments were performed as described below.

Formulations:

A B. thuringiensis RTI545 spore concentrate ($1.0\times10^{10}$ cfu/ml) in water was applied at an amount of $1.0\times10^{6}$ cfu/seed.

MAXIM (SYNGENTA CROP PROTECTION, INC) was applied to seed at 0.0064 mg A1/kernel (A.I.=fludioxonil).

APRON XL (SYNGENTA CROP PROTECTION, INC) was applied to seed according to manufacturer label (A.I.=mefenoxam).

PONCHO 250, PONCHO 500 VOTIVO, and PONCHO 1250 VOTIVO (BAYER CROP SCIENCE) were each applied to seed according to manufacturer label (PONCHO A.I.=clothianidin and VOTIVO A.I.=Bacillus firmus 1-1582).

In the first field trial experiment, corn seeds were treated with slurries containing: 1) chemical control MAXIM+APRON XL (referred to as "FC"); 2) FC+ the insecticide bifenthrin 0.125 mg/seed; 3) FC+PONCHO 1250 (clothianidin 1.25 mg/seed) and VOTIVO (Bacillus firmus 1-1582); 4) FC+PONCHO 250 (clothianidin 0.25 mg/seed); 5) FC+PONCHO 500 (clothianidin 0.5 mg/seed) and VOTIVO (Bacillus firmus 1-1582) and; 6) FC+bifenthrin (0.125 mg/seed)+spores of B. thuringiensis RTI545.

The treated corn seed were planted in separate field trials in Wisconsin in soil infested with the insect pests wireworm and seed maggot. In one trial, manure was added to plots to attract egg laying by Delia spp. adults. Ratings collected and analyzed were % emergence, plant stand, % wireworm damage, % seed maggot damage, plant vigor and yield. Insect feeding damage severity was rated by visual inspection 34 days after planting, and plant vigor was ranked on a scale of 1 to 5, with 1 being very bad and 5 representing an excellent plant vigor rating.

The results are shown below in Table IX. Inclusion of the B. thuringiensis RTI545 in combination with the insecticide bifenthrin resulted in significant improvements in percent emergence, plant stand, vigor and control of both wireworm and seed maggot over seeds treated with bifenthrin alone. In addition, the results of the combination of B. thuringiensis RTI545 and bifenthrin were statistically equivalent to the product PONCHO 1250 VOTIVO at controlling wireworm and showed an improvement over this product in controlling seed maggot. These data indicate that corn seed treatment with a combination of B. thuringiensis RTI545 and a chemical insecticide such as bifenthrin significantly improves insect control over inclusion of chemical insecticide alone and is superior to commercially available products for some types of insect control.

TABLE IX

Control of wireworm and seed maggot in corn field trials after seed treatment with a combination of chemical insecticide and spores of RTI545 as compared to PONCHO VOTIVO.

| | TREATMENT | Emerge % | Stand % | Wireworm % Damage | Seed Maggot % Damage | Vigor 1-5 | | |
|---|---|---|---|---|---|---|---|---|
| 1 | FC* | 70 | 78 | 26 | 14 | 3 | 3 | 3 |
| 2 | FC + Bifenthrin | 81 | 85 | 13 | 11 | 3.8 | 4 | 4 |
| 3 | FC + Poncho 1250 Votivo | 91 | 93 | 6.2 | 5.4 | 4 | 4.3 | 4.5 |
| 4 | FC + PONCHO 250 | 80 | 89 | 14 | 11 | 3.8 | 4 | 4 |
| 5 | FC + Poncho 500 Votivo | 85 | 89 | 14 | 7.4 | 4 | 4 | 4 |
| 6 | FC + Bifenthrin + RTI545 | 92 | 96 | 5.6 | 3.2 | 4.5 | 4.8 | 5 |

*FC is the fungicide check applied to all treatments containing fludioxonil and Mefenoxam to provide disease protection In a second field trial corn seeds were also treated with the same slurries as the first trial containing: 1) chemical control MAXIM+APRON XL (referred to as "FC"); 2) FC+bifenthrin; 3) FC+PONCHO 1250 VOTIVO; 4) FC+PONCHO 250; and 5) FC+bifenthrin+spores of RTI545. The treated corn seed were planted in separate field trial in Wisconsin with wireworm present and no manure added so seed maggot was not a problem. Damage of corn roots from wireworm feeding was rated 41 days after planting.

The results are shown below in Table X and show similar results to Table IX above. Specifically, inclusion of the B. thuringiensis RTI545 in combination with the insecticide bifenthrin resulted in significant improvements in percent emergence, plant stand, vigor and control of wireworm over seeds treated with bifenthrin alone. In addition, the results of the combination of B. thuringiensis RTI545 and bifenthrin were statistically equivalent or superior to the product PONCHO 1250 VOTIVO at controlling wireworm.

TABLE X

Control of wireworm in corn field trials after seed treatment with a combination of chemical insecticide and spores of RTI545 as compared to PONCHO VOTIVO.

| | TREATMENT | Emergence % | Stand % | Wireworrn % Damage (Root) | Vigor 1-5 |
|---|---|---|---|---|---|
| 1 | FC* | 68 | 76 | 32 | 3 |
| 2 | FC + Bifenthgrin | 79 | 85 | 21 | 4 |
| 3 | FC + Poncho 1250 Votivo | 89 | 93 | 11 | 4.3 |

TABLE X-continued

Control of wireworm in corn field trials after seed treatment with a combination of chemical insecticide and spores of RTI545 as compared to PONCHO VOTIVO.

| | TREATMENT | Emergence % | Stand % | Wireworm % Damage (Root) | Vigor 1-5 |
|---|---|---|---|---|---|
| 4 | FC + PONCHO 250 | 79 | 86 | 17 | 4 |
| 5 | FC + Bifenthrin + RTI545 | 91 | 95 | 4 | 4.5 |

*FC is the fungicide check applied to all treatments containing fludioxonil and Mefenoxam to provide disease protection The average yield in the corn field trials after seed treatment with a combination of chemical insecticide and spores of RTI545 as compared to PONCHO VOTIVO was also determined. The results are shown below in Table XI. Inclusion of the B. thuringiensis RTI545 in combination with the insecticide bifenthrin resulted in significant improvements in yield as compared to seeds treated with bifenthrin alone. In addition, the combination of RTI545 and bifenthrin outperformed both PONCHO 500 VOTIVO and PONCHO 1250 VOTIVO by increasing yield 13 bushels/acre (from 180.5 to 193.7 and from 185.5 to 193.7 bushels/acre, respectively) representing a 6.8% and 4.2% increase in grain yield, respectively. These data indicate that corn seed treatment with a combination of RTI545 and a chemical insecticide such as bifenthrin significantly improves yield over inclusion of chemical insecticide alone, and reduces the need for in-furrow application of larger quantities of chemical insecticides to control damage by insects.

TABLE XI

Average yield in corn field trials after seed treatment with a combination of chemical insecticide and spores of B. thuringiensis RTI545 as compared to PONCHO VOTIVO

| | | Bushels/acre | | | Kg/hectare | | |
|---|---|---|---|---|---|---|---|
| | TREATMENT | LB02 | LB01 | Average N = 2 | LB02 | LB01 | Average N = 2 |
| 1 | FC | 130.2 | 149.1 | 139.7 | 8,173 | 9359 | 8,767 |
| 2 | FC + Bifenthrin | 159.8 | 173.9 | 166.9 | 10,031 | 10,916 | 10,476 |
| 3 | FC + PONCHO 250 | 171.4 | 174.2 | 172.8 | 10,759 | 10,935 | 10,847 |
| 4 | FC + PONCHO 500 VOTIVO | 177 | 184 | 180.5 | 11,111 | 11,550 | 11,330 |
| 5 | FC + PONCHO 1250 VOTIVO | 183.4 | 187.5 | 185.5 | 11,512 | 11,769 | 11,644 |
| 6 | FC + Bifenthrin + RTI545 | 191.9 | 195.4 | 193.7 | 12,046 | 12,265 | 12,159 |

The effect on growth under insect pressure by treating corn seed with spores of RTI545 was further evaluated. In a set of greenhouse studies, corn seeds were first treated with the seed treatment slurries as described as follows and then planted in soil infested with the pest wireworm (10 wireworms per pot with one seed), along with a control set where the soil did not contain wireworm. The seed treatment slurries were as follows: 1) chemical control MAXIM+APRON XL (referred to as "FC"); 2) FC; 3) FC+bifenthrin (0125 mg/seed for all treatments treated); 4) FC+bifenthrin+RTI545 $5.0\times10^6$; 5) FC+bifenthrin+RTI545 $5.0\times10^6$ and heat-treated; 6) FC+bifenthrin+RTI545 $1.0\times10^6$; 7) FC+RTI545 $5.0\times10^6$; and 8) FC+PONCHO 1250. The treated seeds were evaluated for percent emergence.

The results are shown below in Table XII. Inclusion of the B. thuringiensis RTI545 in combination with the insecticide bifenthrin resulted in 100% emergence, which was an improvement over inclusion of bifenthrin alone and provided results equivalent to the control without wireworm and the FC+PONCHO 1250 chemical treatment. Wireworm feeding prunes roots causing corn plant stunting and RTI545 alone or bifenthrin with RTI545 reduced plant stunting in surviving plants. RTI545 alone exhibited activity on preventing plant loss but was inferior to insecticide bifenthrin in providing early protection against stunting. However, RTI545 was more effective in preventing plant stunting as the plants grew (data not shown). These data indicate that inclusion of spores of RTI545 in corn seed treatment, alone or in combination with a chemical insecticide such as bifenthrin, significantly improves plant health in the presence of the insect pest wireworm.

TABLE XII

Emergence and growth in corn greenhouse studies in the presense of wireworm after seed treatment with chemical insecticide and RTI545.

| | Treatment | Emergence 1 = 100% | % Plants Surviving with no stunting (based on plants seeded) |
|---|---|---|---|
| 1 | FC no wireworm | 1.00 | 100 |
| 2 | FC | 0.17 | 0 |
| 3 | FC + Bifenthrin | 0.75 | 58 |
| 4 | FC + Bifenthrin + RTI545 $5\times10^6$ | 0.83 | 75 |
| 5 | FC + Bifenthrin + RTI545 $5\times10^6$ heat | 0.83 | 83 |
| 6 | FC + Bifenthrin + RTI545 $1\times10^6$ | 1.00 | 92 |
| 7 | FC + RTI545 $5\times10^6$ | 0.50 | 50 |

TABLE XII-continued

Emergence and growth in corn greenhouse studies in the presense of wireworm after seed treatment with chemical insecticide and RTI545.

| | Treatment | Emergence 1 = 100% | % Plants Surviving with no stunting (based on plants seeded) |
|---|---|---|---|
| 8 | FC + PONCHO 1250 | 1.00 | 100 |
| | Standard Deviation | 0.175389044 | |
| | CV | 23.13 | |

Experiments were performed to determine the effect on yield by treating soybean seed with a standard fungicidal combination of chemical active ingredients in addition to spores of B. thuringiensis RTI545, in combination with a chemical insecticide. The experiments were performed as described below.

Formulations:

A RTI545 spore concentrate ($1.0\times10^{10}$ cfu/ml) in water was applied at an amount of $1.0\times10^{6}$ cfu/seed.

FC is a formulation containing fludioxonil, TPM, and mefenoxam which was applied to seed at 2.5 g/100 g seed (fludioxonil), 10 g/100 g (TPM), and 7.5 g/100 g seed (mefenoxam).

Thiamethoxam was applied to seed at 50 g/100 g seed.

In the experiment, soybean seeds were mixed with a solution containing: 1) chemical control fludioxonil/TPM/mefenoxam ("FC"); 2) FC+insecticide thiamethoxam; and 3) FC+thiamethoxam+spores of B. thuringiensis RTI545. The treated soybean seeds were planted at three sites (N=3) that had wireworm infestation, and the yield was analyzed.

The results are shown below in Table XIII. Inclusion of the RTI545 spores in combination with the thiamethoxam resulted in significant improvements in yield as compared to seeds treated with thiamethoxam alone increasing yield by 1.6 bushels/acre (from 68.2 to 69.8), representing a 2.3% increase in yield. These data indicate that soybean seed treatment with a combination of RTI545 and a chemical insecticide significantly improves yield over inclusion of insecticide alone, and reduces the need for in-furrow application of larger quantities of chemical insecticides to control damage by insects.

TABLE XIII

Average yield in soybean after seed treatment with chemical insecticide and spores of RTI545 in addition to a standard fungicidal seed treatment (FC).

| Treatment | Bu/A (N = 3) | Kg/hectare |
|---|---|---|
| FC | 60.8 | 4089 |
| FC + Thiamethoxam | 68.2 | 4586 |
| FC + Thiamethoxam + RTI545 | 69.8 | 4694 |

One possible explanation for the improved insect control though seed- or in furrow-treatment with spores of RTI545 in combination with a chemical insecticide is illustrated in FIG. 1. Specifically, FIG. 1A is a schematic diagram that shows insect control with a chemical insecticide alone, (i.e. without RTI545). FIG. 1A shows on the far left a plant seed (inner circle) coated with a chemical insecticide (dark band surrounding inner circle), which is surrounded by plant insect pests in the plant rhizosphere represented by horizontal marks. The middle portion of the diagram shows the sprouted plant seed with diffused insecticide protecting the roots of the plant seed from the insect pests (protection represented by the "X" marks). The far right of the diagram shows diminished protection of the roots of the plant seed from the insect pests as the roots grow beyond the diffusion zone of the chemical insecticide. FIG. 1B shows how addition of Bacillus thuringiensis RTI545 spores to the coating on the plant seed (or in furrow application of RTI545 spores around the time of planting) improves insect control over use of the insecticide coating alone. Specifically, the far right side of the FIG. 1B diagram shows continued protection of the roots of the plant seed from the insect pests even as the roots grow beyond the diffusion zone of the chemical insecticide as a result of the establishment of Bacillus thuringiensis RTI545 in the plant rhizosphere.

Example 9

Nematode Control by Bacillus thuringiensis RTI545 Isolate in Infested Soil

The ability of the Bacillus thuringiensis RTI545 strain to reduce the nematode infestation in soybean and potato was determined as described below.

A greenhouse study was performed with soybean plants potted in soil infected with Southern root-knot nematodes to determine the effect of seed treatment with RTI545 spores applied at an amount of $1.0\times10^{6}$ cfu/seed. Soybean plants were potted in soil infected with live eggs of Southern Root-Knot nematodes (Meloidogyne incognita). Seeds treated with each of the products PONCHO VOTIVO (BAYER CROPSCIENCE LP; A.I.=40.3% clothianidin, 8.1% Bacillus firmus 1-1582) and AVICTA COMPLETE (SYNGENTA; A.I.=11.7% thiamethoxam, 10.3% abamectin, 2.34% thiabendazole, 0.3% fludioxonil, 0.23% mefenoxam, 0.12% azoxystrobin), separately, containing chemical active ingredients at the rates designated on the products labels. The data are shown in Table XIV below. At 63 days after initiation, there was no statistical difference in the number of nematode eggs/pot for the seed treatment with RTI545 cells and the chemical combination AVICTA COMPLETE, however, the number of nematode eggs/pot for the seed treated with RTI545 was less than that for the seed treated with PONCHO VOTIVO. There was no statistical difference in the number of juveniles/pot for any of the treatments after 63 days. These data demonstrate the positive effect on nematode control on soybean provided by Bacillus thuringiensis RTI545.

TABLE XIV

Nematode infestation over time in soybeans after seed treatment with RTI545 spores.

| | Southern Root-Knot Nematode | | | | |
|---|---|---|---|---|---|
| | 35 DP-1 | | | 63 DP-1 | |
| | Egg Mass/ Pot | Eggs/ Pot | Juveniles/ Pot | Eggs/ Pot | Juveniles/ Pot |
| No Nematodes | 0 | 0 | 0 | 0 | 0 |
| Control | 57 | 6434 | 2 | 7880 | 463.2 |
| RTI545 | 41 | 6340 | 0 | 2795 | 268.8 |
| PONCHO VOTIVO | 43 | 5540 | 0 | 6720 | 427.2 |
| AVICTA COMPLETE | 7 | 1377 | 0 | 2455.1 | 79.2 |
| CV | 29.83 | 35.75 | 349.6 | 29.41 | 130.09 |

A greenhouse study was performed with potato plants potted in soil naturally infected with Globodera sp. nematodes to determine the effect of treatment of the soil with Bacillus thuringiensis RTI545 cells. In this experiment, the effect of soil enhancement with RTI545 cells on the number of cysts per gram of root biomass was determined at 60 days after initiation of the study. Potatoes (nematode sensitive variety "Bintje") were planted in soil infected with Globodera sp. (Control) and enhanced with $10E^{9}$ cfu spores per liter soil of Bacillus thuringiensis RTI545 (RTI545). The results are shown in the graph in FIG. 5. Additional soil treatments were included in the study: VYDATE product (Vydate; DUPONT; A.I.=Oxamyl [Methoyl N'N'-dimethyl-N-[(methyl carbamoyl)oxyl)oxy]-1-thiooxamimidate), BIOACT product (BAYER CROPSCIENCES LP; A.I.=of Paecilomyces lilacinus strain 251), CAREX product (CAREX, NUFARM, pyridaben), and Bacillus thuringiensis spp. kurstaki HD-1). The products were applied at the rates designated on the product labels. As can be seen in FIG. 5, the number of cysts per gram of root biomass for the soil treated with RTI545 cells was significantly reduced compared to all of the treatments including the products containing chemical active ingredients.

Example 10

Cotton Seed Treatment with Bacillus thuringiensis RTI545 Inoculated with Rhizoctonia Experiments were performed to investigate the effect on emergence, root disease, and yield in cotton in the presence of Rhizoctonia disease pressure when seeds were treated with a the RTI545 strain in addition to chemical active agents for pathogen control.

Specifically, an experiment in cotton was set up as follows: 1) seed was untreated (UTC); 2) seed was treated with a base combination of Fludioxonil+Mefenoxam+Imidacloprid according to manufacturer label (referred to as "B"); 3) seed was treated with base plus $5\times10^{+5}$ cfu/seed of RTI545 (B+RTI545); and 4) seed was treated with base plus VIBRANCE (active ingredient sedaxane; SYNGENTA CROP PROTECTION, INC) according to label instructions (B+VIBRANCE). Field trials were performed in Georgia. The trials were inoculated with Rhizoctonia by mixing the dried inoculum with the seed at the time of planting to a prescribed rate to provide infection when the seed commenced to grow. The average percent cotton emergence is presented in Table XV below.

The results in Table XV show that treating with RTI545 spores in addition to the base resulted in significant improvement in percent emergence over that of the chemical base alone (67% versus 45% for base alone). In addition, treatment with RTI545 performed as well as the base plus commercial product VIBRANCE with chemical active. Thus, seed treatment with RTI545 can provide significant improvement in emergence even under conditions of severe pathogen pressure.

TABLE XV

Cotton emergence in *Rhizoctonia*-inoculated soil from seeds treated with RTI545.

| | Treatment | % Emergence |
|---|---|---|
| 1 | Untreated control | 23 |
| 2 | B | 45 |
| 3 | B + RTI545 ($5 \times 10^5$ CFU/seed) | 67 |
| 4 | B + VIBRANCE | 63 |

Example 11

Effects on Growth and Yield by Treating Wheat Seed with Bacillus thuringiensis RTI545

Experiments were performed to determine the effect on growth and yield under insect pressure by wheat seed treated with spores of B. thuringiensis RTI545 alone, or in combination with one or both of chemical fungicides and a chemical insecticide. More specifically, the effects on growth, yield, and control of wheat pests wireworm and white grub were measured in field trials in Wisconsin. The experiments were performed as described below comparing addition of B. thuringiensis RTI545 spores to a seed and to a seed plus fungicide base, and addition of RTI545 spores in combination with 2 concentrations of the insecticide, bifenthrin, in addition to the fungicide base.

In the field trial experiment, wheat seeds were treated with slurries containing: 1) chemical fungicide base difenoconazole/tebuconazole/TPM/mefenoxan (referred to as "FC"); 2) FC+spores of B. thuringiensis RTI545 (RTI545 $10^6$ cfu/g seed); 3) FC+Bifenthrin (20 g/seed); 4) FC+Bifenthrin (20 g/seed)+RTI545 $10^6$ cfu/g seed; 5) FC+bifenthrin (50 g/seed); and 6) FC+bifenthrin (50 g/seed)+RTI545 $10^6$ cfu/g seed.

The treated wheat seed were planted in field trials in Wisconsin in soil infested with the insect pests wireworm and white grub. Ratings collected and analyzed were % emergence, % wireworm damage, % grub damage, plant vigor and yield. Insect feeding damage severity was rated by visual inspection 35 days after planting, and plant vigor was ranked on a scale of 1 to 5, with 1 being low and 5 representing highly vigorous.

The results are shown below in Table XVI. Seed treatment with each of the B. thuringiensis RTI545 spores, and treatment with the RTI545 spores with either the fungicide base alone or in combination with the insecticide, bifenthrin, resulted in significant improvements in percent emergence, vigor, control of wireworm and grub, and yield. In every case tested, inclusion of the RTI545 spores in the wheat seed treatment resulted in significant improvements in growth, vigor, pest control, and yield.

TABLE XVI

Control of wireworm and grub in wheat field trials after seed treatment with a combination of chemical insecticide and spores of RTI545.

| | | Emerge | Vigor (35 DAP) | % Damage | | Yield | |
|---|---|---|---|---|---|---|---|
| | TREATMENT | (21 DAP) % | 1-5 | Wireworm | Grub | Bu/Acre | Kg/Ha |
| 1 | FC* | 59 | 3.5 | 26 | 7.5 | 70 | 4708 |
| 2 | FC* + RT1545 | 72 | 5 | 10 | 4 | 82 | 5514 |
| 3 | FC + Bifenthrin (20 g) | 64 | 4 | 19 | 6.5 | 77 | 5178 |
| 4 | FC + Bifenthrin (20 g) + RTI545 | 74 | 5 | 8 | 3 | 81 | 5472 |
| 5 | FC + Bifenthrin (50 g) | 70 | 4.8 | 14 | 3.3 | 82 | 5514 |
| 6 | FC + Bifenthrin (50 g) + RTI545 | 76 | 5 | 6 | 1.8 | 86 | 5784 |

*FC is the fungicide check applied to all treatments containing Difenoconazole + TPM + Tebuconazole + Mefenoxam to provide disease protection Example 12

Impact of Bacillus thuringiensis RTI545 Seed Treatment on Growth and Yield of Soybeans Inoculated with Rhizoctonia A field trial was conducted in Quitman, Ga. to test the efficacy of the RTI545 addition to a base fungicide/insecticide chemical treatment to provide Rhizoctonia protection compared to the untreated seed or this base or the positive control compromising the synthetic base plus sedaxane.

Soybean seeds of the soybean variety cv. Pioneer 93Y92 were treated with separate slurries being prepared for the chemical and biological treatments which were simultaneously applied to the seed. Seeds were placed in a jar which was shaken on a modified paint shaker until the product was uniformly coated on the seeds. The base chemical treatment comprised four actives comprising 1) 12.8 g/L of fludioxonil, 2) 38.4 g/L of mefenoxam, 3) 38.4 g/L of thiophanate-methyl (TPM) and 4) 256 g/L of thiamethoxam as a single formulation and applied at 41.4 mL/140,000 seeds. Vibrance (500 g/L of sedaxane) was applied separately as a seed treatment to the positive control treatment. Dry technical of the strain RTI545 was used and diluted in water to achieve an application rate of $5\times10^5$ cfu/seed. Products were slurried with water to at least to 65 mL/140,000 seeds to ensure uniform application. The trial comprised randomized complete block tests (4 replicates) being 1.8 meters by 9 meters plots. Seeds of the soybean variety cv. Treated and untreated seeds were planted in sandy soil using a cone planter at a seeding rate of 13 seeds/meter at a depth of 2.5 cm and row spacing of 90 cm. Inoculum of Rhizoctonia was mixed and planted with the seed. The plots and soybeans plants were treated under generally accepted agronomic conditions for soybean including conventional tillage and with supplemental irrigation as needed. The plants were assessed during the growing period for emergence, vigor (on a 1-5 qualitative scale with 5 being best) and then harvested to assess yield converted to bu/acre and kg/hectare. The results are summarized in the Table XVII below.

TABLE XVII

Impact of RTI545 seed treatment on growth and yield of soybeans inoculated with Rhizoctonia

| | Description | | | | | | | |
|---|---|---|---|---|---|---|---|---|
| | Emergence | | | Vigor | | | Yield | |
| | Rating Unit | | | | | | | |
| | % | | | 1-5 | | | BU/Acre | Kg/Ha |
| | Plant-Eval Interval (DAP) | | | | | | | |
| | 6 | 14 | 18 | 6 | 14 | 18 | 131 | |
| Untreated Seed | 22 | 20 | 16 | 1.8 | 1.8 | 1.3 | 29.8 | 2004 |
| Base Synthetic (Base) | 71 | 57 | 50 | 2.8 | 2.3 | 2.8 | 48.9 | 3289 |
| Base + RTI545 $5\times10^5$ cfu/seed | 86 | 60 | 60 | 3.8 | 4.8 | 4.5 | 49.6 | 3336 |
| Base + Vibrance | 83 | 65 | 62 | 4.0 | 4.3 | 4.3 | 52.8 | 3551 |

The impact of Rhizoctonia is to reduce stand, reduce vigor and lower yields. Inoculation was effective in view of the base treatment being significantly improved over the untreated seed for all plant counts, vigor and yield assessments.

The addition of RTI545 to the chemical base resulted in significant increase in stand at all 3 assessment timings, vigor to increase significantly at 2 assessment timings and numerically higher yield compared to the chemical base. Reduced stand and vigor ratings may be due to plants dying off. The addition of sedaxane to the synthetic base, an active registered for Rhizoctonia control, resulted in increased emergence, vigor and numerically higher yield than the base synthetic. RTI545 addition was similar to the sedaxane treatment for all ratings demonstrating this strain equal effectiveness in reducing damage from Rhizoctonia in this trial.

Example 13

Impact of Bacillus thuringiensis RTI 545 Seed Treatment on Growth and Yield of Corn Planted into a Field Infested with Wireworms and Seed Maggots A field trial was conducted in Wisconsin to test the efficacy of the RTI545 in addition to either a base fungicide (Maxim and Apron XL both applied at 5.2 mL/100 kg) or this base fungicide and clothianidin (0.25 mg/seed) or this base fungicide plus bifenthrin (0.125 mg/seed) or this base fungicide plus chlorantraniliprole (2 rates evaluated for 0.25 and 0.5 mg/seed) or bifenthrin (0.125 mg/seed) combined with chlorantraniliprole (0.25 mg/seed). As a positive control to demonstrate a high level of protection, clothianidin was applied at 1.25 mg/seed combined with the base fungicide with this high rate representing 5-fold the loading of the low rate of clothianidin also evaluated.

Corn seeds (variety cv. Ag Venture G5891) were treated with separate slurries being prepared for the chemical and biological treatments which were simultaneously applied to the seed. Seeds were placed in a jar which was shaken on a modified paint shaker until the product was uniformly coated on the seeds. The base chemical treatment comprised three commercial formulations comprising 1) 40.3% of fludioxonil, 2) 33.3% of mefenoxam, 3) 18.4% of chlorantraniliprole, 4) 600 g/L of clothianidin, and 5) 400 g/L of bifenthrin. Dry technical of the strain RTI545 was used and diluted in water to achieve an application rate $1\times10^6$ cfu/seed. Products were slurried to at least to 600 mL/100 kg to ensure uniform application. Treatment 13 is Base+Clothianidin 1.25 mg/seed as a positive control for a high level of wireworm protection. The trial comprised randomized complete block tests (4 replicates) of 3 meters by 15 meters plots. The corn seeds were planted in Milford silty clay loam soil using a cone planter at a seeding rate of 93,900 seeds/hectare, a depth of 6.25 cm and row spacing of 75 cm. Manure was spread on top of plots after seeding to attract seed maggots to lay eggs in the plots. The plots and corn plants were treated under generally accepted agronomic conditions for corn including minimum tillage with rainfall being average to above average for the area. The plants were assessed during the growing period for emergence, vigor (on a 1-5 qualitative scale with 1=low vigor and 5=high vigor—fullness of plots rated), feeding damage by wireworms and seed maggot (rated by sampling 50 plants and assessing for root damage by wireworm or seed maggot), and then harvested to assess yield. The results are summarized in Table XVIII.

TABLE XVIII

Impact of RTI545 seed treatment on growth and yield of corn planted into a field infested with wireworms and seed maggot

| | Description | | | | | | | | | | | |
|---|---|---|---|---|---|---|---|---|---|---|---|---|
| | % Emergence | | | % Stand | Vigor | | | Wireworm Damage % | | Seed Maggot Damage % | | Yield Bu/A |
| | Plant-Evaluation Interval (Days after Planting) | | | | | | | | | | | |
| | 18 | 28 | 42 | 164 | 19 | 28 | 42 | 28 | 42 | 28 | 42 | 164 |
| 1. MAXIM + APRON XL (Base) | 49 | 60 | 62 | 57 | 3.0 | 3.0 | 3.0 | 17.4 | 33.6 | 23.6 | 22.5 | 149.3 |
| 2. Base + RTI545 1 × $10^6$ cfu/seed | 52 | 65 | 69 | 63 | 3.3 | 3.3 | 3.3 | 11.2 | 23.7 | 18.7 | 21.3 | 170.9 |
| 3. Base + Clothianidin 0.25 mg/seed | 63 | 77 | 82 | 72 | 3.5 | 4.0 | 4.0 | 8.6 | 17 | 12.4 | 12.5 | 210.4 |
| 4. Treatment 3 + RTI545 at 1 × $10^6$ cfu/seed | 76 | 91 | 91 | 80 | 4.5 | 4.5 | 4.8 | 5 | 4.2 | 4.2 | 3.8 | 225.8 |
| 5. Base + Bifenthrin | 68 | 81 | 82 | 72 | 4.0 | 4.0 | 4.0 | 7.3 | 10.8 | 8.3 | 12.5 | 211.1 |
| 6. Treatment 5 + RTI545 at 1 × $10^6$ cfu/seed | 74 | 88 | 90 | 79 | 4.3 | 4.3 | 4.5 | 7.3 | 9.7 | 6.1 | 7.5 | 226 |
| 7. Base + Chlorantraniliprole 0.25 mg/seed | 63 | 76 | 78 | 69 | 3.5 | 4.0 | 4.0 | 10 | 16.2 | 12.4 | 12.5 | 198.6 |
| 8. Treatment 7 + RTI545 at 1 × $10^6$ cfu/seed | 70 | 82 | 83 | 73 | 4.0 | 4.0 | 4.0 | 8.6 | 12.4 | 8.3 | 10 | 213.4 |
| 9. Base + Chlorantraniliprole 0.5 mg/seed | 69 | 82 | 82 | 72 | 4.0 | 4.0 | 4.0 | 8.6 | 10.8 | 8.3 | 11.3 | 209.7 |
| 10. Treatment 9 + RTI545 at 1 × $10^6$ cfu/seed | 80 | 93 | 95 | 83 | 4.8 | 4.8 | 5.0 | 6.1 | 7.3 | 3.2 | 3.8 | 235.6 |
| 11. Base + Chlorantraniliprole 0.25/Bifenthrin | 72 | 84 | 86 | 76 | 4.0 | 4.0 | 4.0 | 10 | 11.2 | 7.3 | 8.8 | 217.3 |
| 12. Treatment 11 + RTI545 at 1 × $10^6$ 6 cfu/seed | 82 | 94 | 95 | 83 | 5.0 | 5.0 | 5.0 | 5 | 7.3 | 3.2 | 2.5 | 237.7 |
| 13. Base + Clothianidin 1.25 mg/seed | 76 | 91 | 93 | 81 | 4.5 | 4.5 | 4.8 | 5 | 4.2 | 6.1 | 3.8 | 229.2 |

The impact of wireworm feeding is to reduce stand, reduce vigor and stunt plants by root pruning, damage roots and reduce yields. Seed maggots can also reduce stand and feed on seed, causing stunting.

The addition of RTI545 to the fungicide base (treatment 2 versus treatment 3) resulted in emergence counts that were significantly higher at 42 and 164 days after planting, reduced the root damage caused by wireworm feeding and significantly increased yield over the fungicide base. Although RTI545 provided insecticide protection, the level of protection was lower than synthetic products evaluated demonstrating the benefit of adding this product to an insecticide to ensure satisfactory performance.

The addition of RTI545 to clothianidin (treatments 3 and 4 respectively) applied at 0.25 mg/seed significantly increased emergence at all 4 assessment timings, significantly increased vigor at all 3 assessment timings, reduced feeding damage caused by seed maggot and wireworm and significantly increased yield. The addition of RTI545 to the low rate of clothianidin resulted in similar performance to the high rate of clothianidin applied at 1.25 mg/seed.

The addition of RTI545 to bifenthrin (01.25 mg/seed for treatments 5 and 6 respectively) significantly increased emergence at 1 assessment timings, significantly increased vigor at 1 assessment timing, significantly reduced feeding damage caused by seed maggot at the last assessment timing and significantly increased yield.

The addition of RTI545 to chlorantraniliprole (0.25 mg/seed for treatments 7 and 8 respectively) significantly increased emergence at 3 assessment timings and significantly increased yield.

The addition of RTI545 to chlorantraniliprole (0.5 mg/seed for treatments 9 and 10 respectively) significantly increased emergence at all 4 assessment timings, significantly increased vigor at all 3 assessment timings, reduced significantly feeding damage caused by seed maggot, reduced numerically wireworm feeding damage and significantly increased yield. The addition of RTI545 to chlorantraniliprole (0.5 mg/seed) resulted in this product performing similarly to the high rate of clothianidin (1.25 mg/seed).

The addition of RTI545 to a chlorantraniliprole and bifenthrin combination (treatments 9 and 10 respectively) significantly increased emergence at all 4 assessment timings, significantly increased vigor at all 3 assessment timings, reduced significantly feeding damage caused by seed maggot and wireworm and significantly increased yield. The addition of RTI545 this combination resulted in this product to perform similarly or improved to the high rate of clothianidin (1.25 mg/seed) with the final yield of this treatment being over 8 bu/acre higher than the high rate of clothianidin.

These results demonstrate the insecticide protection provided by RTI545 enhances protection provided by three unique IRAC classes of synthetic insecticides. These results demonstrate that RTI545 provides protection by itself; however, the combination with an effective insecticide helps ensure a much higher level of benefits being apparent.

Example 14

In-Furrow Applications of Bacillus thuringiensis RTI545 in Corn Field Trials In-furrow treatments of corn with RTI545 were studied in multiple field trials in various locations in North America to evaluate effectiveness against wireworm (Melanotus spp.)

and corn rootworm (Diabrotica spp.). The effects on yield and crop damage of several treatments compared to untreated controls for the individual North America trials were aggregated and summarized as an average for the trial in the following tables as % yield increase and % reduction in damage compared to the untreated controls. Seven trials were evaluated for wireworm. Eighteen trials were evaluated for corn rootworm. Five trials with heavy damage from corn rootworm were averaged separately.

TABLE XIX

Effect on corn yield of treatments with RTI545 on wireworm-infested field plots

| Treatment | Rate | % Yield Increase |
|---|---|---|
| Bifenthrin | 56 g ai/Ha | 5 |
| RTI545 | $3 \times 10^{11}$ CFU/Ha | 1 |
| | $3 \times 10^{12}$ CFU/Ha | 2 |
| Bifenthrin + | 56 g ai/Ha + $3 \times 10^{11}$ CFU/Ha | 6 |
| RTI545 | 56 g ai/Ha + $3 \times 10^{12}$ CFU/Ha | 7 |
| Tefluthrin | 168 g ai/Ha | 5 |

TABLE XX

Effect on corn yield and rootworm damage of treatments with RTI545 on corn rootworm-infested field plots

| | | | | Heavy CRW Pressure | |
|---|---|---|---|---|---|
| | Rate | % Yield Increase | % Damage reduction | % Yield Increase | % Damage reduction |
| Bifenthrin | 112 g ai/Ha | 4 | 42 | 11 | 45 |
| RTI545 | $1.24 \times 10^{12}$ CFU/Ha | 3 | 28 | 11 | 35 |
| | $6.18 \times 10^{12}$ CFU/Ha | 4 | 37 | 11 | 44 |
| Bifenthrin + RTI545 | 112 g ai/Ha + $1.24 \times 10^{12}$ CFU/Ha | 4 | 49 | 9 | 51 |
| | 112 g ai/Ha + $6.18 \times 10^{12}$ CFU/Ha | 6 | 55 | 22 | 62 |
| Tefluthrin | 168 g ai/Ha | 3 | 46 | 16 | 52 |

Yield data from 7 wireworm trials indicate treatments containing RTI545 show a slight advantage over bifenthrin alone and commercial standard tefluthrin at its highest rate. Data from 18 trials for corn rootworm indicate yields from treatments containing RTI545 show yields equal to or slightly higher than bifenthrin alone, and tefluthrin at its highest rate. Data from these 18 trials also indicate that corn treated with RTI545 in combination with an insecticide resulted in less root damage to corn in corn rootworm infested soil than the industry standard of tefluthrin at its maximum rate or bifenthrin at maximum rate or when RTI545 was applied alone as a treatment. When there was heavy corn rootworm pressure, the reduction in damage ratings was similar to the treatments under typical rootworm pressure, but the percentage yield increase was better. Overall, the data from these trials indicate that RTI545 combined with bifenthrin can enhance corn yield and decrease insect damage to corn roots when compared to untreated areas or areas treated with the industry standard tefluthrin.

Field trials were also conducted with in-furrow treatments of corn with RTI545 in Europe to evaluate effectiveness against wireworm (Agriotes spp.)—Data not shown.

Example 15

Impact of Bacillus thuringiensis RTI545 on Growth and Yield of Peanut Inoculated with Rhizoctonia A field trial was conducted in Georgia to test the efficacy of the biological combination of the invention as a seed treatment of peanut inoculated with Rhizoctonia solani.

Peanut seeds were treated with a dry dust formulation with a final application rate of 200 g/100 kg of seed containing RTI545, resulting in an application of RTI545 at $3.0 \times 10^6$ CFU/g of seed, and simultaneous applied with DYNASTY PD, a United States registered peanut product containing fludioxonil (2%), mefenoxam (0.4%) and azoxystrobin (3.2%) with an application of 195 g/100 kg of seed. Seeds were placed in a jar and shaken until the product was uniformly coated on the seeds.

The trial comprised randomized complete block tests using 6 foot by 30 foot (about 1.8 meters by 9.1 meters) plots. Treated and untreated peanut (Arachis hypogaea, var. GA 06) seeds were planted. Using a cone planter, seeds were planted 1.25 inch deep (3 cm) with row spacing of 36 inches (0.9 m) in sandy loam soil. The plots were inoculated with Rhizoctonia sp. to ensure infestation. The plots and peanut plants were treated under generally accepted agronomic conditions for peanut including conventional tillage and irrigation as needed until they were ready for harvest. The plants were assessed during the growing period for emergence, vigor (on a 1-5 qualitative scale), and then harvested to assess yield. The results are summarized in Table XXI.

TABLE XXI

Results from field trial of RTI545 seed treated peanuts against *Rhizoctonia*

| Rating | Timing DAP | Untreated Seed | Base Chemical | Base Chemical + RTI545 |
|---|---|---|---|---|
| Plant Counts | 8 | 3 | 10 | 12 |
| | 11 | 11 | 27 | 39 |
| | 16 | 15 | 41 | 45 |
| Vigor (1-5) | 8 | 1.8 | 3.0 | 3.3 |
| | 11 | 2.3 | 2.8 | 4.0 |
| | 16 | 1.8 | 2.5 | 3.5 |
| Yield lb/Acre | 135 | 1277 | 3231 | 3733 |
| Kg/Hectare | | 1434 | 3628 | 4191 |

All seed treatments had a higher stand than the untreated control (UTC) at all 3 assessment timings. At all three assessment timings, the treatment including RTI545 provided the best emergence. The untreated seed had the lowest vigor at all 3 assessment timings. The treatment including RTI545 provided stronger vigor than the UTC and the base chemical treatment. All products provided significantly higher yield than the UTC. The treatment including RTI545 outperformed base chemical treatment.

Example 16

Impact of Bacillus thuringiensis RTI 545 Seed Treatment on Lesion Nematode

Soil assays on seed-treated corn to assess activity against lesion nematode (Pratylenchus penetrans) were conducted in a greenhouse. Corn (cv. Viking) seeds were treated with a base seed treatment of fludioxonil (1.1 ml/SU) and metalaxyl-M (1.1 ml/SU) (all seeds). Some seeds were also treated with PONCHO/VOTIVO (clothianidin+B. firmus 1-1582 at 80 ml/SU), RTI545 at $5\times10^5$ CFU/seed, RTI545 at $1\times10^6$ CFU/seed or a mixture of either RTI545 ($5\times10^6$ CFU/seed)+Bacillus subtilis strain CH201 ($2.5\times10^6$ CFU/seed)+Bacillus licheniformis strain CH200 ($2.5\times10^6$ CFU/seed) or RTI545 ($5\times10^6$ CFU/seed)+Bacillus velezensis strain RTI301 ($5\times10^5$ CFU/seed)+Bacillus licheniformis strain CH200 ($2.5\times10^6$ CFU/seed).

In one type of assay, the treated seeds were planted in cone-shaped containers in 90 ml of soil (80.4% sand, 14.8% silt, 4.8% clay, organic matter 1.1%, pH 6.9). After planting the seeds, the soil was inoculated on the same day with 4000 nematodes (mixed stages: J2-adults) per seed in 200 μl of carrier (2% methyl cellulose). A control used seeds with the base seed treatment in non-inoculated soil. The test plantings were top watered using a mist sprinkler. The test was evaluated at 2 (data not shown) and 7 days after emergence for total root length using WinRhizo™ software. Root length data and nematode % reduction data were transformed using the arcsine square root transformation prior to ANOVA analysis using an ANOVA Fisher test at $\alpha=0.1$.

TABLE XXII

The effect of RTI545 seed treatment in corn on the total root length of seedlings grown under lesion nematode pressure.

| Treatment | % Root length Increase vs inoculated control |
|---|---|
| Base seed treatment, inoculated | 0 |
| Base seed treatment, non-inoculated | 18 |
| Base seed treatment + PONCHO/VOTIVO | 19 |
| Base seed treatment + RTI545 ($5\times10^5$ CFU/seed) | 30 |
| Base seed treatment + RTI545 ($1\times10^6$ CFU/seed) | 34 |

Inoculation of corn seedlings with lesion nematodes numerically reduced total root length. The total root length of seedlings treated with PONCHO/VOTIVO (commercial standard) was greater than the non-treated inoculated seedlings and similar to non-treated non-inoculated seedlings. The total root length of RTI545-treated seedlings was significantly increased when compared with non-treated inoculated seedling (30-34%) and was statistically similar but numerically greater than the total root length of seedlings treated with PONCHO/VOTIVO.

Similar tests using 2000 nematodes/seed for inoculation were carried out in 130 ml of soil and measured nematode numbers per root and fresh top weight of the plants at 8 weeks after nematode inoculation. The results are presented in Table XXIII. Lesion nematode infestation resulted in severe reduction of the fresh top weight (FTW) of corn plants. The FTW of inoculated control plants was reduced by 50% when compared with non-inoculated plants. The high rate of RTI545 provided statistically greater FTW compared to standards PONCHO/VOTIVO and to inoculated nematode control. These results indicate that RTI545 seed treatment increases plant tolerance to nematode infestation by sustaining plant growth in the presence of nematode pests. In addition, similar positive effects on plant growth/FTW were observed where RTI545 was used at the lower rate in combination with other strains: RTI545 ($1\times10^6$ CFU/seed)+Bacillus subtilis strain CH201 ($2.5\times10^6$ CFU/seed)+Bacillus licheniformis strain CH200 ($2.5\times10^6$ CFU/seed), or RTI545 ($1\times10^5$ CFU/seed)+RTI301 ($5\times10^5$ CFU/seed)+Bacillus licheniformis strain CH200 ($2.5\times10^6$ CFU/seed). Moreover, RTI545 seed treatment at a high rate ($1.0\times10^6$ CFU/seed) provided very good control of lesion nematodes (50% reduction of nematode numbers in the roots). PONCHO/VOTIVO did not reduce nematode numbers in roots.

TABLE XXIII

The effect of RTI545 seed treatment in corn on fresh top weight and nematode counts in roots after inoculation with lesion nematode.

| Treatment | % Reduction in Penetration | Fresh Top Weight (g) |
|---|---|---|
| Base seed treatment, inoculated | — | 6.5 |
| Base seed treatment, non-inoculated | 0 | 12.8 |
| Base seed treatment + PONCHO/VOTIVO | No control | 8.5 |
| Base seed treatment + RTI545 ($5\times10^5$ CFU/seed) | 8 | 11.6 |
| Base seed treatment + RTI545 ($1\times10^6$ CFU/seed) | 49 | 13.3 |
| Base seed treatment + RTI545 ($5\times10^5$ CFU/seed) + CH200($2.5\times10^6$ CFU/seed) + CH201 ($2.5\times10^6$ CFU/seed) | 12 | 13.2 |
| Base seed treatment + RTI545 ($5\times10^5$ CFU/seed) + RTI301 ($5\times10^5$ CFU/seed) + CH200 ($2.5\times10^6$ CFU/seed) | 6 | 12.1 |

Similar tests wherein RTI545 was applied as a soil drench at the rate of $2.5\times10^{11}$ CFU/ha provided 71% reduction in lesion nematode numbers per root compared to 95% for abamectin. In soil drench tests applied to pots in the greenhouse with soil infested with lesion nematode eggs and adults (2000 individuals/pot) RTI545 at the rate of $2.5\times10^{13}$ CFU/ha provided 80% reduction in nematode numbers per root compared to 86% reduction by cadusafos.

Example 17

Impact of Bacillus thuringiensis RTI 545 on Soybean Cyst Nematode in Soil Drench Assays The activity of RTI545 against soybean cyst nematode (Heterodera glycines) was investigated in soil drench assays in a greenhouse. Individual soybean (cv. AG4730) seeds were planted in 120 ml soil (80.4% sand, 14.8% silt, 4.8% clay, organic matter 1.1, pH 6.9) in cone-shaped containers and watered with individual bottom watering. The containers were inoculated with nematode eggs at a rate of 4000 eggs in 1 mL of 2% methyl cellulose per container 21 days after planting. Soil drench (in 10 ml volume per 100 ml soil)

applications of RTI545 and AGRI-MEK 0.15 EC (a.i. 2% abamectin) and VENERATE XC (94.46% heat-killed Burkholderia spp. strain A396 cells and spent fermentation media) were applied at 7 and 21 days after planting. The rates tested were RTI545 washed spores at $2.5\times10^{12}$ CFU/ha, $2.5\times10^{13}$ CFU/ha and $2.5\times10^{14}$ CFU/ha; abamectin at 1 ppm (0.01 mg a.i./plant) and 10 ppm (0.1 mg a.i./plant) corresponding to seed treatment label rate; and VENERATE XC at 5% v/v (500 mg/plant), corresponding to 4.5× the in-furrow rate. The tests were evaluated at day 70 (7 weeks after inoculation). Evaluations were carried out by extraction of cysts from roots and soil and counting the total number of cysts under a stereomicroscope.

TABLE XXIV

Number of cysts of soybean cyst nematode extracted from roots and soil.

| Treatment | Number of cysts extracted | % Reduction of cysts |
|---|---|---|
| Untreated, non-inoculated | 0 | — |
| Untreated, inoculated | 147 | na |
| RTI545 ($2.5 \times 10^{12}$ CFU/ha) | 50 | 66 |
| RTI545 ($2.5 \times 10^{13}$ CFU/ha) | 93 | 37 |
| RTI545 ($2.5 \times 10^{14}$ CFU/ha) | 66 | 55 |
| Abamectin (0.01 ppm) | 31 | 79 |
| Abamectin (0.1 ppm) | 7 | 96 |
| VENERATE XC (500 mg/plant) | 43 | 71 |

The data show that RTI545 reduced nematode cyst numbers up to 66%. There was no clear dose response between the rates tested and activity. The activity of RTI545 was not statistically different from the biological standard VENERATE XC. Chemical standard abamectin had the highest activity. The rate of 0.01 mg/plant provided 79% reduction and 0.1 mg/plant provided 96% reduction.

Example 18

Suspension Concentrate Formulations Comprising Bacillus thuringiensis RTI545

Representative suspension concentrates comprising Bacillus thuringiensis RTI545 are summarized in Table XXV. They were prepared by mixing spores of RTI545 with the other components in a suitable mixing vessel or homogenizer.

TABLE XXV

Suspension Concentrate Formulations

| Component | Function | Example 18A | Example 18B |
|---|---|---|---|
| | | % (w/w) | |
| RTI545 $3 \times 10^{11}$ cfu/g | Active ingredient | 5.25 | 9.59 |
| Ammonium sulfate | Antifreeze | 9.5 | |
| Glycerol (86.5%) | Antifreeze | | 48 |
| Attapulgite (20-35% aq. suspension) | Thickener | 9.0 | |
| Alkyl polyglycosides, mixture | Dispersant | 8.0 | |
| Anionic Phosphate ester surfactants, mixture | Dispersant | 7.0 | |
| Aq. Dispersion of ethylene vinyl acetate copolymer | Dispersant | | 0.89 |
| silicone emulsion | antifoam | 0.3 | |
| Potassium sorbate | Preservative | 0.1 | 0.2 |
| Water | Diluent | 59.54 | 38.82 |

Example 19

Suspension Concentrate Formulations Comprising Bacillus thuringiensis RTI545 and Bifenthrin Representative suspension concentrates comprising Bacillus thuringiensis RTI545 and bifenthrin insecticide are summarized in Tables XXVI and XXVII. They were prepared by mixing spores of RTI545 with the other components in a suitable mixing vessel or homogenizer. Example 19C is a foamable composition that can be applied as a foam to seeds or in-furrow at time of planting. The foamable composition 19C can be optionally diluted with water and mixed with a pressurized gas such as air in a foaming chamber comprising a foaming medium such as a plurality of glass beads to prepare a foam.

TABLE XXVI

SC formulations of RTI545 and bifenthin

| Component | Function | Example 19A | Example 19B | Example 19C |
|---|---|---|---|---|
| | | % (w/w) | | |
| Technical B fenthr n | Active ingredient (99%) | 15.81 | | |
| | Active ingredient (98.2%) | | 15.92 | 15.96 |
| RTI545 $3 \times 10^{11}$ cfu/g | Active ingredient | 3.62 | 5.25 | 5.0 |
| Ammonium sulfate | Antifreeze | 10.75 | 9.5 | |
| Glycerin | Antifreeze | 12.7 | | |
| | Thickener | 2.15 | | |
| Attapulgite | Thickener, 20-35% aq. suspension | | 9.0 | |
| Xanthan gum | Thickener, 2% suspension | | | 12 |
| Alkyl polyglycosides, mixture | Dispersing agent | 6.00 | 8.0 | 1.25 |
| Anionic Phosphate ester surfactants, mixture | Dispersing agent | 1.57 | 7.0 | 1.25 |

TABLE XXVI-continued

SC formulations of RTI545 and bifenthin

| Component | Function | Example 19A | 19B | 19C |
|---|---|---|---|---|
| | | % (w/w) | | |
| Sodium decyl sulphate 35-40% in water | Foaming agent | | | 20 |
| silicone emulsion | Antifoam | 0.1 | 0.3 | |
| 1,2-benzisothiazolin-3-one | Preservative, 20% alkaline solution | 0.15 | | |
| | Preservative, 20% aqueous solution | | | 0.1 |
| Kathon ® CG-ICP | Preservative | | | 0.1 |
| sodium salt o-phenylphenate | Preservative | | | 0.1 |
| Potassium sorbate | Preservative | | 0.1 | |
| Sodium benzoate | Preservative | | 0.1 | |
| Acetic acid | Diluent | 0 | 1.21 | 0 |
| Water | Diluent | 59.85 | 43.62 | 31.54 |

TABLE XXVII

| Component | Function | Example 19D | 19E |
|---|---|---|---|
| | | % (w/w) | |
| Technical Bifenthrin | Active ingredient (99%) | 17.4 | 16.6 |
| RTI545 $3 \times 10^{11}$ cfu/g | Active ingredient | 5.0 | 10 |
| Ammonium sulfate | Antifreeze | 11.2 | 10.6 |
| Alkyl polyglycosides, mixture | Dispersing agent | 12.9 | 12.3 |
| Anionic Phosphate ester surfactants, mixture | Dispersing agent | 1.3 | 1.2 |
| silicone emulsion | Antifoam | 0.3 | 0.3 |
| Potassium sorbate | Preservative | 0.1 | 0.1 |
| Sodium benzoate | Preservative | 0.1 | 0.1 |
| Citric acid | Diluent | 0.8 | 0.7 |
| $H_3PO_4$ | Diluent | 0.4 | 0.5 |
| Water | Diluent | 50.4 | 47.5 |

Spore stability during storage at elevated temperatures was very good, as shown below in Table XXVIII, in which formulation 18D was stored at 54° C. for two weeks, with little change in the concentration of RTI545 Ssores.

TABLE XXVIII

Spore stability during storage
Spore stability

| Initial | 2 weeks storage at 54° C. |
|---|---|
| $1.36 \times 10^{10}$ cfu | $1.30 \times 10^{10}$ cfu |

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

SEQUENCE LISTING

```
<160> NUMBER OF SEQ ID NOS: 2

<210> SEQ ID NO 1
<211> LENGTH: 1544
<212> TYPE: DNA
<213> ORGANISM: Bacillus thuringiensis

<400> SEQUENCE: 1

agaaaggagg tgatccagcc gcaccttccg atacggctac cttgttacga cttcacccca      60

atcatctgtc ccaccttagg cggctggctc caaaaaggtt accccaccga cttcgggtgt     120

tacaaactct cgtggtgtga cgggcggtgt gtacaaggcc cgggaacgta ttcaccgcgg     180

catgctgatc cgcgattact agcgattcca gcttcatgta ggcgagttgc agcctacaat     240

ccgaactgag aacggtttta tgagattagc tccacctcgc ggtcttgcag ctctttgtac     300

cgtccattgt agcacgtgtg tagcccaggt cataaggggc atgatgattt gacgtcatcc     360
```

```
ccaccttcct ccggtttgtc accggcagtc accttagagt gcccaactta atgatggcaa    420
ctaagatcaa gggttgcgct cgttgcggga cttaacccaa catctcacga cacgagctga    480
cgacaaccat gcaccacctg tcactctgct cccgaaggag aagccctatc tctagggttt    540
tcagaggatg tcaagacctg gtaaggttct tcgcgttgct tcgaattaaa ccacatgctc    600
caccgcttgt gcgggccccc gtcaattcct ttgagtttca gccttgcggc cgtactcccc    660
aggcggagtg cttaatgcgt taacttcagc actaaagggc ggaaaccctc taacacttag    720
cactcatcgt ttacggcgtg gactaccagg gtatctaatc ctgtttgctc cccacgcttt    780
cgcgcctcag tgtcagttac agaccagaaa gtcgccttcg ccactggtgt tcctccatat    840
ctctacgcat ttcaccgcta cacatggaat tccactttcc tcttctgcac tcaagtctcc    900
cagtttccaa tgaccctcca cggttgagcc gtgggctttc acatcagact taagaaacca    960
cctgcgcgcg ctttacgccc aataattccg gataacgctt gccacctacg tattaccgcg   1020
gctgctggca cgtagttagc cgtggctttc tggttaggta ccgtcaaggt gccagcttat   1080
tcaactagca cttgttcttc cctaacaaca gagttttacg acccgaaagc cttcatcact   1140
cacgcggcgt tgctccgtca gactttcgtc cattgcggaa gattccctac tgctgcctcc   1200
cgtaggagtc tgggccgtgt ctcagtccca gtgtggccga tcaccctctc aggtcggcta   1260
cgcatcgttg ccttggtgag ccgttacctc accaactagc taatgcgacg cgggtccatc   1320
cataagtgac agccgaagcc gcctttcaat ttcgaaccat gcagttcaaa atgttatccg   1380
gtattagccc cggtttcccg gagttatccc agtcttatgg gcaggttacc cacgtgttac   1440
tcacccgtcc gccgctaact tcttgagagc aagctctcaa tccattcgct cgacttgcat   1500
gtattaggca cgccgccagc gttcatcctg agccaggatc aaac                    1544
```

<210> SEQ ID NO 2
<211> LENGTH: 3534
<212> TYPE: DNA
<213> ORGANISM: Bacillus thuringiensis

<400> SEQUENCE: 2

```
ttgacaggtc aactagttca atacggacgc caccgccaac gaagaagtta tgcccgtatt     60
agtgaagtat tagagttacc aaatcttatc gaaattcaaa cctcttctta tcagtggttt    120
cttgatgagg gtttgcgaga aatgttccaa gacatttctc cgattgaaga ctttacggga    180
aatctatcgc ttgaatttat cgactacagc ttaggtgaac ctaaatactc tgtagacgaa    240
tgcaaagagc gtgatgtgac gtatgcagca ccacttcgtg taaaagtgcg tctaatcaac    300
aaggaaactg gtgaagtaaa agaacaagat gtgttcatgg gagatttccc actcatgaca    360
gagactggaa cattcgtaat taacggtgca gaacgtgtta tcgtttccca gttagttcgc    420
tctccaagcg tatactatag tggcaaagtg gataaaaacg gaaaacgtgg ttttactgct    480
actgtaattc caaaccgcgg agcttggtta gagtatgaga cagatgctaa ggatgttgta    540
tatgtgcgta ttgaccgtac gcgtaaactt cctgtaactg ttttgttacg cgcattaggg    600
tttggctctg atcaagaaat caccgagctt ttaggtgata acgaatactt aagcaacaca    660
ttagaaaaag acaacacaga tagtacagaa aaagcattgc ttgaaattta tgagcgtcta    720
cgtcctggtg aaccaccaac agtagaaaat gctaagagct tacttgtgtc tcgtttcttc    780
gatccaaagc gctacgattt agcaaatgta ggtcgctata agatcaacaa gaagttacac    840
attaaaaaca gattgtttaa tcaacgttta gctgaaacat tagtggatcc agaaactggt    900
gaaattttag cggcagaagg aacaatctta gatcgtcgta cacttgatcg cattttacct    960
```

```
tacttagaga aaaacattgg attcaaaaca gcgaaaccaa tgggtggagt ggtagaaggc   1020
gatgttgagc tgcaatctat taagatttat gctcctgagt cggaaggcga acgtgtaatt   1080
aatgtaattg gtaatgcaaa tattactcgt gatgtgaaac acatcacacc aggtgatatc   1140
cttgcttcta tcagttactt cttcaaccta ctatacaaag taggggatac agatgatatt   1200
gaccatttag gaaaccgtcg tctgcgttct gttggagaac tattacaaaa tcaattccgt   1260
atcggtcttt ctcgtatgga acgtgttgtt cgtgagagaa tgtcgatcca agatacaaat   1320
gcaattacac cacaggcgct aattaatatt cgtcctgtta ttgcatctat taaagagttc   1380
ttcggaagtt ctcagttatc tcagttcatg gaccaaacaa atccattagc agagttaact   1440
cacaaacgaa gactatctgc attaggacct ggtggtttaa cgcgtgagcg cgcaggcttt   1500
gaagtacgtg acgttcatta ctcccactac ggtcgtatgt gtccgattga aacaccagag   1560
ggaccaaaca tcggtttgat taactcatta tcttcgttcg cgaaagtaaa tgagtttggt   1620
ttcattgaaa caccatatcg tcgtgttgac ccagaaactg gtcttgtaac agggcatgtt   1680
gattatttaa cagcagatga agaagataac tatgttgtag cccaagcgaa tatgaaatta   1740
tctgatgaag gtgaattcct aagtgaagat atcgtagctc gtttccgtgg tgaaaacatt   1800
gtcacaaata gagaacgcat cgactacatg gatgtatctc caaaacaagt agtgtcggca   1860
gcgacagctt gtattccgtt cttagaaaac gatgactcta accgcgcact tatgggagcg   1920
aacatgcaac gtcaggcggt tccgttaatg aatccggaat ctccgattgt aggtacaggt   1980
atggagtacg tatcagcaaa agactcaggt gctgcagtaa tctgtaaaca tcctggtgtt   2040
gttgagcgcg tagaagcacg tgaagtttgg gtacgtcgct atgtagaagt tgacggtcaa   2100
acagtaaaag gcgacttaga tcgctacaaa atgcaaaaat tcattcgttc taaccaagga   2160
acttgttaca accaacgtcc aatcgtaagt gttggaaatg aagttgtaaa aggtgaaatc   2220
cttgcggatg gtccttctat ggaattaggt gaactagcac ttggacgtaa cgtgcttgtt   2280
ggcttcatga cttgggacgg ttataactac gaggatgcga tcatcatgag tgagcgcctt   2340
gtaaaagatg atgtgtacac ttctattcat attgaagaat atgaatcaga agctcgtgat   2400
acgaagcttg gaccagaaga aattacacgt gacattccaa atgttgggga agacgcatta   2460
cgtaaccttg acgagcgcgg tatcattcgc gttggtgctg aagtaaaaga tggagattta   2520
cttgttggta aagtaacacc taaaggtgta acagaattaa cagctgaaga acgtctatta   2580
catgctatct ttggagaaaa agcgcgtgaa gtacgtgata catcactacg tgtaccacac   2640
ggtggtggcg gtattatctt agacgtaaaa gtattcaacc gtgaagatgg cgatgaattg   2700
ccaccaggcg tgaatcaact tgtacgtgca tatatcgttc aaaaacgtaa aatttctgaa   2760
ggtgacaaga tggccggacg tcacggtaac aaaggtgtta tttctcgtat tttaccagaa   2820
gaagatatgc cttacttacc agacggtacg ccaatcgata tcatgttaaa cccattaggg   2880
gtaccatctc gtatgaatat cggtcaggta ttagagcttc atcttggtat ggcagcaaga   2940
tacctgggca ttcacattgc aacaccagta ttcgatggtg ctcgtgagga agatgtttgg   3000
ggcacaattg aagaagctgg tatggcaaat gacgcgaaaa caatcctgta tgacggacgt   3060
actggtgaac cattcgataa ccgcgtatct gttggtgtca tgtatatgat caaacttgcg   3120
cacatggttg acgataaact tcatgctcgt tctactggac catactcact tgtaacgcag   3180
caacctcttg gaggtaaagc tcagttcggt ggacagcgtt tcggtgagat ggaggtttgg   3240
gcacttgaag cttacggtgc tgcttatact cttcaagaaa tcttaacagt gaagtctgat   3300
gatgttgttg gacgtgttaa gacttatgaa gcaattgtta aaggcgaaaa tgttccagaa   3360
```

-continued

```
ccaggcgttc ctgaatcatt caaagtattg attaaagagc tgcaaagttt aggtatggac   3420

gttaaaatga tgtctagcga cgatacagaa attgaaatgc gtgatacaga agatgacgat   3480

gatcatcaat cagcagataa attgaatgtc gaagttgaga caactaagga ataa         3534
```

That which is claimed:

1. A composition comprising a biologically pure culture of Bacillus thuringiensis RTI545 deposited as ATCC No. PTA-122161, and an agriculturally acceptable adjuvant, which improves the stability of the Bacillus thuringiensis RTI545;

for application to a plant for one or both of benefiting plant growth or conferring protection against a plant pest in a susceptible plant.

2. The composition of claim 1, wherein the biologically pure culture of Bacillus thuringiensis RTI545 is in the form of spores or vegetative cells.

3. The composition of claim 1, wherein the adjuvant comprises a planting matrix, a carrier, a binder, a surfactant, a dispersant, or a yeast extract.

4. The composition of claim 1, further comprising an insecticide, a fungicide, nematicide, bacteriocide, biostimulant, herbicide, plant extract, microbial extract, plant growth regulator, fertilizer or combinations thereof present in an amount suitable to benefit plant growth and/or to confer protection against a pathogenic infection in a susceptible plant.

5. The composition of claim 1, wherein the composition further comprises a chemical insecticide.

6. The composition of claim 5 wherein the chemical insecticide comprises chlorantraniliprole, chlorethoxyfos, chlorpyrifos-e, cyantraniliprole, cyclaniliprole, cypermethrin, dichloropropene, flupyradifurone, gamma-cyhalothrin, profenofos, tebupirimfos, tefluthrin, kappa-bifenthrin, kappa-tefluthrin, carbofuran, carbosulfan, oxamyl, thiodicarb, chlorpyrifos, chlorpyrifos-e, chlorpyrifos-methyl, diazinon, phorate, terbufos, fipronil, acetamiprid, clothianidin, imidacloprid, thiacloprid, thiamethoxam, abamectin, flonicamid, flubendiamide, bifenthrin, lambda-cyhalothrin, cypermethrin, zeta-cypermethrin, deltamethrin, pyridaben or any mixtures thereof.

7. The composition of claim 6, wherein the chemical insecticide comprises bifenthrin.

8. The composition of claim 1, wherein the composition further comprises a chemical fungicide.

9. The composition of claim 8 wherein the chemical fungicide comprises thiabendazole, fluxapyroxad, penflufen, sedaxane, bitertanol, cyproconazole, difenoconazole, fluquinconazole, flutriafol, ipconazole, myclobutanil, prothioconazole, triadimefon, triadimenol, tebuconazole, triticonazole, prochloraz, imazalil, benomyl, carbencladzim, hymexazole, azoxystrobin, fluoxastrobin, pyraclostrobin, trifloxystrobin, carboxin, flutolanil, metalaxyl, mefenoxam, penthiopyrad, fluopyram, silthiofam, fluazinam, pyrimethanil, fludioxonil, iprodione, tricyclazole, captan, dammet, mancozeb, metam, thiram, guazatine, tolclofos-methyl, pencycuron, thiophanate-methyl, fenpicoxamide, mefentrifluconazole, fluindapyr, or any mixtures thereof.

10. The composition of claim 1, wherein the composition further comprises a chemical nematicide.

11. The composition of claim 10, wherein the chemical nematicide comprises benomyl, fenamiphos, cadusafos, ethoprophos, fosthiazate, chloropicrin, dammet, fluensulfone, oxamyl, 1,3-dichloropropene (telone), metam sodium, metam potassium, metam salt, methyl bromide, allyl isothiocyanate, fluazaindolizine, tioxazafen, fluopyram, or any mixtures thereof.

12. The composition of claim 1, wherein the composition is in a formulation compatible with a liquid fertilizer or crop nutrition product.

13. The composition of claim 12, wherein the composition further comprises a hydrated aluminum-magnesium silicate and at least one dispersant.

14. The composition of claim 12 or 13, comprising a bifenthrin insecticide wherein the bifenthrin is present at a concentration ranging from 0.1 g/ml to 0.2 g/ml.

15. A method for one or both of benefiting growth of a plant or conferring protection against a plant pest in a susceptible plant, the method comprising delivering a composition comprising a biologically pure culture of Bacillus thuringiensis RTI545 deposited as ATCC No. PTA-122161, to the plant, plant part, seed of the plant, roots of the plant, soil or growth medium surrounding the plant, or soil or growth medium before planting the plant or sowing seed of the plant, in an amount suitable to benefit the plant growth and/or to confer protection against the plant pest in the susceptible plant.

16. A method for one or both of benefiting growth of a plant or conferring protection against a plant pest in a susceptible plant, the method comprising: planting a seed of the plant, wherein the seed has been coated with a composition comprising a biologically pure culture of Bacillus thuringiensis RTI545 deposited as ATCC PTA-122161, wherein growth of the plant from the seed is benefited and/or protected against the plant pest is conferred.

17. The method of claim 15 or 16, wherein the plant comprises corn, soybean, potato, cotton, tomato, pepper, cucurbit, sugarcane, peanut or wheat.

18. The method of claim 15 or 16, wherein the plant pest comprises an insect selected from the group consisting of Lygus spp., Coleoptera, Diabrotica spp., Melanotus spp., Phyllophaga spp., Limonius spp., Agriotes spp., Lepidoptera, Peridroma spp., Euxoa spp., Agrotis spp., Diptera, Hylemya spp., Tetanops sp. Hemiptera, Pemphigus sp., Aphis sp., Agonoderus sp., Feltia spp., or combinations thereof.

19. The method of claim 18, wherein the plant pest comprises a plant bug, rootworm, wireworm, soil-dwelling maggot, or white grub complex.

20. The method of claim 15 or 16, wherein the plant pest comprises a plant pathogenic nematode selected from the group consisting of Rotlyenchulus spp., Xiphinema spp., Hoplolaimus spp., Paratylenchus spp., Criconemoides spp., Meloidogyne spp., Hemicycliophora spp., Helicotylenchus spp., Trichodorus spp., Heterodera spp., Belonolaimus spp., Tylenchorhynchus spp., Globodera spp. or combinations thereof.

21. The method of claim 20 wherein the nematode comprises a Meloidogyne spp nematode, Pratylenchus spp. nematode, or Globodera spp. nematode or Heterodera spp. nematode.

22. The method of claim 15 or 16, wherein the plant pest comprises a plant fungal pathogen or a plant bacterial pathogen selected from the group consisting of Alternaria ssp., Aspergillus spp., Botrytis spp, Cercospora spp., Fusarium spp., Phytophthora spp., Rhizoctonia spp., Magnaporthe spp., Pythium spp., Monilinia spp., Colletotrichum spp., Sclerotinia spp., and Erwinia spp.

23. The method of claim 22 wherein the plant fungal pathogen comprises Rhizoctonia spp.

24. The method of claim 15 or 16, further comprising delivering a liquid fertilizer or crop nutrition product to the seed of the plant.

25. A plant seed coated with a composition comprising spores of a biologically pure culture of Bacillus thuringiensis RTI545 deposited as ATCC No. PTA-122161, present in an amount suitable to benefit plant growth and/or to confer protection against a plant pest in a susceptible plant.

26. The plant seed of claim 25, wherein the seed comprises the seed of corn, soybean, potato, cotton, tomato, pepper, cucurbit, sugarcane, peanut or wheat.

* * * * *